US011679126B2

(12) United States Patent
Melero-Martin et al.

(10) Patent No.: US 11,679,126 B2
(45) Date of Patent: Jun. 20, 2023

(54) METHODS TO ENHANCE MICROVASCULAR ENGRAFTMENT OF BIOENGINEERED AND PRIMARY TISSUES

(71) Applicant: Children's Medical Center Corporation, Boston, MA (US)

(72) Inventors: Juan M. Melero-Martin, Bedford, MA (US); Ruei-Zeng Lin, Brookline, MA (US)

(73) Assignee: Chldren's Medical Center Corporation, Boston, MA (US)

( * ) Notice: Subject to any disclaimer, the term of this patent is extended or adjusted under 35 U.S.C. 154(b) by 806 days.

(21) Appl. No.: 16/461,885

(22) PCT Filed: Nov. 17, 2017

(86) PCT No.: PCT/US2017/062396
§ 371 (c)(1),
(2) Date: May 17, 2019

(87) PCT Pub. No.: WO2018/094267
PCT Pub. Date: May 24, 2018

(65) Prior Publication Data
US 2019/0275080 A1    Sep. 12, 2019

Related U.S. Application Data

(60) Provisional application No. 62/506,391, filed on May 15, 2017, provisional application No. 62/423,540, filed on Nov. 17, 2016.

(51) Int. Cl.
| | |
|---|---|
| *A61K 35/44* | (2015.01) |
| *C12N 5/00* | (2006.01) |
| *A61K 35/15* | (2015.01) |
| *A61K 38/02* | (2006.01) |
| *A61K 38/16* | (2006.01) |
| *C12N 5/0787* | (2010.01) |
| *C12N 15/00* | (2006.01) |
| *A61K 38/19* | (2006.01) |
| *A61K 38/00* | (2006.01) |
| *A61K 35/39* | (2015.01) |

(52) U.S. Cl.
CPC .............. *A61K 35/15* (2013.01); *A61K 35/39* (2013.01); *A61K 35/44* (2013.01); *A61K 38/005* (2013.01); *A61K 38/02* (2013.01); *A61K 38/16* (2013.01); *A61K 38/19* (2013.01); *C12N 5/0018* (2013.01); *C12N 5/0642* (2013.01); *C12N 15/00* (2013.01); *C12N 2533/54* (2013.01); *C12N 2533/56* (2013.01)

(58) Field of Classification Search
CPC ...... A61K 35/39; A61K 35/44; C12N 5/0018; C12N 2533/56
See application file for complete search history.

(56) References Cited

U.S. PATENT DOCUMENTS

| | | | |
|---|---|---|---|
| 2008/0181893 A1 | 7/2008 | Lobov et al. | |
| 2011/0213127 A1 | 9/2011 | Gill et al. | |
| 2013/0236429 A1* | 9/2013 | Melero-Martin | ...... A61K 35/28 424/93.7 |

OTHER PUBLICATIONS

Li and Mooney, Designing hydrogels for controlled drug delivery. Nature Review Materials, vol. 1, No. 12 (online Oct. 18, 2016) doi: 10.1038/natrevmats.2016.71. (Year: 2016).*
Ahsan et al., "Bioengineered tissues: the science, the technology, and the industry," Orthodontics & craniofacial research, Aug. 2005, 8(3):134-140.
Atala, "Bioengineered tissues for urogenital repair in children" Pediatric research, May 2008, 63(5):569-575.
Ausprunk et al., "Vascularization of normal and neoplastic tissues grafted to the chick chorioallantois. Role of host and preexisting graft blood vessels," The American journal of pathology, Jun. 1975, 79(3):597-610.
Baranski et al., "Geometric control of vascular networks to enhance engineered tissue integration and function," Proceedings of the National Academy of Sciences, May 7, 2013, 110(19):7586-7591.
Bekes et al., "Tumor-recruited neutrophils and neutrophil TIMP-free MMP-9 regulate coordinately the levels of tumor angiogenesis and efficiency of malignant cell intravasation," The American journal of pathology, Sep. 1, 2011, 179(3):1455-1470.
Benelli et al., "Neutrophils as a key cellular target for angiostatin: implications for regulation of angiogenesis and inflammation," The FASEB Journal, Feb. 2002, 16(2):267-269.
Chen et al., "Functional human vascular network generated in photocrosslinkable gelatin methacrylate hydrogels," Advanced functional materials, May 23, 2012, 22(10):2027-2039.
Chen et al., "Rapid anastomosis of endothelial progenitor cell-derived vessels with host vasculature is promoted by a high density of cotransplanted fibroblasts," Tissue Engineering Part A, Feb. 1, 2010, 16(2):585-594.
Christoffersson et al., "VEGF—A recruits a proangiogenic MMP-9-delivering neutrophil subset that induces angiogenesis in transplanted hypoxic tissue," Blood, The Journal of the American Society of Hematology, Nov. 29, 2012, 120(23):4653-4662.
Cuartero et al., "N2 neutrophils, novel players in brain inflammation after stroke: modulation by the PPARγ agonist rosiglitazone," Stroke, Dec. 2013, 44(12):3498-3508.
De Palma et al., "Targeting exogenous genes to tumor angiogenesis by transplantation of genetically modified hematopoietic stem cells," Nature medicine, Jun. 2003, 9(6):789-795.
De Palma et al., "Tie2 identifies a hematopoietic lineage of proangiogenic monocytes required for tumor vessel formation and a mesenchymal population of pericyte progenitors," Cancer cell, Sep. 1, 2005, 8(3):211-226.
Fantin et al., "Tissue macrophages act as cellular chaperones for vascular anastomosis downstream of VEGF-mediated endothelial tip cell induction," Blood, The Journal of the American Society of Hematology, Aug. 5, 2010, 116(5):829-840.
Fridlender et al., "Transcriptomic analysis comparing tumor-associated neutrophils with granulocytic myeloid-derived suppressor cells and normal neutrophils," PloS one, 2012, 7(2):1-13.

(Continued)

*Primary Examiner* — Kara D Johnson
(74) *Attorney, Agent, or Firm* — Fish & Richardson P.C.

(57) ABSTRACT

Methods of tissue grafting, and more particularly methods for enhancing tissue graft revascularization, e.g., host engagement of pre-existing graft blood vessels.

17 Claims, 38 Drawing Sheets

Specification includes a Sequence Listing.

(56) References Cited

OTHER PUBLICATIONS

Fridlender et al., "Tumor-associated neutrophils: friend or foe?," Carcinogenesis, May 1, 2012, 33(5):949-955.

Giannoudis et al., "Bone substitutes: an update," Injury, Nov. 1, 2005, 36(3):S20-S27.

Griffith et al., "Tissue engineering—current challenges and expanding opportunities," Science, Feb. 8, 2002, 295(5557):1009-1014.

Grunewald et al., "VEGF-induced adult neovascularization: recruitment, retention, and role of accessory cells," Cell, Jan. 13, 2006, 124(1):175-189.

Hu et al., "Endothelial cell-derived angiopoietin-2 controls liver regeneration as a spatiotemporal rheostat," Science, Jan. 24, 2014, 343(6169):416-419.

Jain et al., "Engineering vascularized tissue," Nature biotechnology, Jul. 2005, 23(7):821-823.

Jia et al., "The endogenous zinc finger transcription factor, ZNF24, modulates the angiogenic potential of human microvascular endothelial cells," The FASEB Journal, Apr. 2015, 29(4):1371-1382.

Jungebluth et al., "RETRACTED: Verification of cell viability in bioengineered tissues and organs before clinical transplantation," Biomaterials, Feb. 2013, 34:4057-4067.

Kølle et al., "Enrichment of autologous fat grafts with ex-vivo expanded adipose tissue-derived stem cells for graft survival: a randomised placebo-controlled trial," The Lancet, Sep. 28, 2013, 382(9898):1113-1120.

Kusumbe et al., "Coupling of angiogenesis and osteogenesis by a specific vessel subtype in bone," Nature, Mar. 2014, 507(7492):323-828.

Lee et al., "Lung stem cell differentiation in mice directed by endothelial cells via a BMP4-NFATc1-thrombospondin-1 axis," Cell, Jan. 30, 2014, 156(3):440-455.

Lin et al., "Human endothelial colony-forming cells serve as trophic mediators for mesenchymal stem cell engraftment via paracrine signaling," Proceedings of the National Academy of Sciences, Jul. 15, 2014, 111(28):10137-10142.

Lin et al., "Transdermal regulation of vascular network bioengineering using a photopolymerizable methacrylated gelatin hydrogel," Biomaterials, Sep. 1, 2013, 34(28):6785-6796.

Ma et al., "Temporal neutrophil polarization following myocardial infarction," Cardiovascular research, May 1, 2016, 110(1):51-61.

Mantovani, "The yin-yang of tumor-associated neutrophils," Cancer cell, Sep. 8, 2009, 16(3):173-174.

Massena et al., "Identification and characterization of VEGF-A—responsive neutrophils expressing CD49d, VEGFR1, and CXCR4 in mice and humans," Blood, The Journal of the American Society of Hematology, Oct. 22, 2015, 126(17):2016-2026.

Melero-Martin et al., "Engineering robust and functional vascular networks in vivo with human adult and cord blood-derived progenitor cells," Circulation research, Jul. 18, 2008, 103(2):194-202.

Melero-Martin et al., "Host myeloid cells are necessary for creating bioengineered human vascular networks in vivo," Tissue engineering Part A, Aug. 1, 2010, 16(8):2457-2466.

Melero-Martin et al., "In vivo vasculogenic potential of human blood-derived endothelial progenitor cells," Blood, The Journal of the American Society of Hematology, June 1, 2007, 109(11):4761-4768.

Mohr et al., "Coronary artery bypass graft surgery versus percutaneous coronary intervention in patients with three-vessel disease and left main coronary disease: 5-year follow-up of the randomised, clinical SYNTAX trial," The lancet, Feb. 23, 2013, 381(9867):629-638.

Moisidis et al., "A prospective, blinded, randomized, controlled clinical trial of topical negative pressure use in skin grafting," Plastic and reconstructive surgery, Sep. 15, 2004, 114(4):917-922.

Murdoch et al., "Mechanisms regulating the recruitment of macrophages into hypoxic areas of tumors and other ischemic tissues," Blood, Oct. 15, 2004, 104(8):2224-2234.

Murdoch et al., "The role of myeloid cells in the promotion of tumour angiogenesis," Nature reviews cancer, Aug. 2008, 8(8):618-631.

Nahrendorf et al., "The healing myocardium sequentially mobilizes two monocyte subsets with divergent and complementary functions," The Journal of experimental medicine, Nov. 26, 2007, 204(12):3037-3047.

Nolan et al., "Molecular signatures of tissue-specific microvascular endothelial cell heterogeneity in organ maintenance and regeneration," Developmental cell, Jul. 29, 2013, 26(2):204-219.

Novosel et al., "Vascularization is the key challenge in tissue engineering," Advanced drug delivery reviews, Apr. 30, 2011, 63(4-5):300-311.

Nozawa et al., "Infiltrating neutrophils mediate the initial angiogenic switch in a mouse model of multistage carcinogenesis," Proceedings of the National Academy of Sciences, Aug. 15, 2006, 103(33):12493-12498.

PCT International Preliminary Report on Patentability in International Application. No. PCT/US2017/062396, dated May 21, 2019, 9 pages.

PCT International Search Report and Written Opinion in International Application. No. PCT/US2017/062396, dated Apr. 26, 2018, 13 pages.

Piccard et al., "On the dual roles and polarized phenotypes of neutrophils in tumor development and progression," Critical reviews in oncology/hematology, Jun. 1, 2012, 82(3):296-309.

Riemenschneider et al., "Inosculation and perfusion of pre-vascularized tissue patches containing aligned human microvessels after myocardial infarction," Biomaterials, Aug. 1, 2016, 97:51-61.

Roca et al., "Regulation of vascular morphogenesis by Notch signaling," Genes & development, Oct. 15, 2007, 21(20):2511-2524.

Rogers et al., "Autogenous bone graft: basic science and clinical implications," Journal of Craniofacial Surgery, Jan. 1, 2012, 23(1):323-327.

Rouwkema et al., "Vascularization in tissue engineering," Trends in biotechnology. Aug. 1, 2008, 26(8):434-441.

Sagiv et al., "Phenotypic diversity and plasticity in circulating neutrophil subpopulations in cancer," Cell reports, Feb. 3, 2015, 10(4):562-573.

Schechner et al., "In vivo formation of complex microvessels lined by human endothelial cells in an immunodeficient mouse," Proceedings of the National Academy of Sciences, Aug. 1, 2000, 97(16):9191-9196.

Serruys et al., "Percutaneous coronary intervention versus coronary-artery bypass grafting for severe coronary artery disease," New England Journal of Medicine, Mar. 5, 2009, 360(10):961-972.

Shapiro et al., "Clinical pancreatic islet transplantation," Nature Reviews Endocrinology, May 2017, 13(5):268-277.

Shojaei et al., "Role of myeloid cells in tumor angiogenesis and growth," Trends in cell biology, Aug. 1, 2008, 18(8):372-378.

Traktuev et al., "Robust functional vascular network formation in vivo by cooperation of adipose progenitor and endothelial cells," Circulation research, Jun. 19, 2009, 104(12):1410-1420.

U.S. Appl. No. 14/131,163, Simons et al., Stimulation of Arterial Collateral Growth and Lymphogenesis, filed Jul. 6, 2012, 53 pages.

Wang et al., "Ephrin-B2 controls VEGF-induced angiogenesis and lymphangiogenesis," Nature, May 2010, 465(7297):483-486.

White et al., "Identification of a potent, selective non-peptide CXCR2 antagonist that inhibits interleukin-8-induced neutrophil migration," Journal of Biological Chemistry, Apr. 24, 1998, 273(17):10095-10098.

Wolford et al., "Considerations in nerve repair," In Baylor University Medical Center Proceedings, Apr. 1, 2003, 16(2):152-156.

Zhou et al., "Interrogating translational efficiency and lineage-specific transcriptomes using ribosome affinity purification," Proceedings of the National Academy of Sciences, Sep. 17, 2013, 110(38):15395-15400.

Fridlender et al., "Polarization of tumor-associated neutrophil phenotype by TGF-β:"N1" versus "N2" TAN," Cancer cell, Sep. 8, 2009, 16(3):183-94.

(56) References Cited

OTHER PUBLICATIONS

Lin et al., "Host non-inflammatory neutrophils mediate the engraftment of bioengineered vascular networks," Nature biomedical engineering, Jun. 13, 2017, 1(6), 27 pages.

Shen et al., Endothelial cells stimulate self-renewal and expand neurogenesis of neural stem cells, Science, May 28, 2004, 304(5675):1338-40.

* cited by examiner

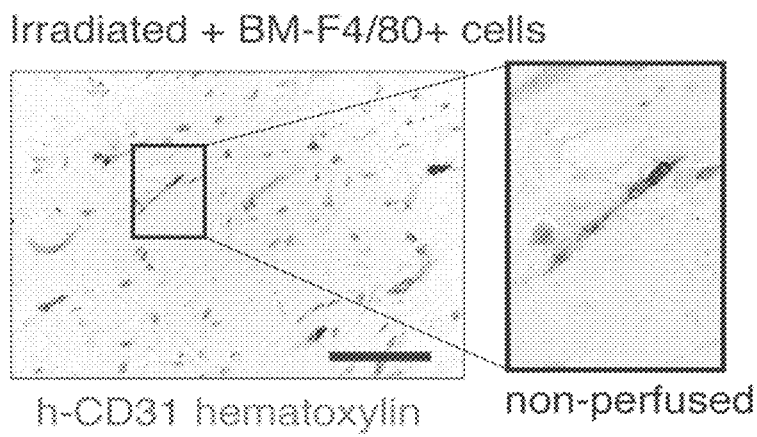
FIG. 9F
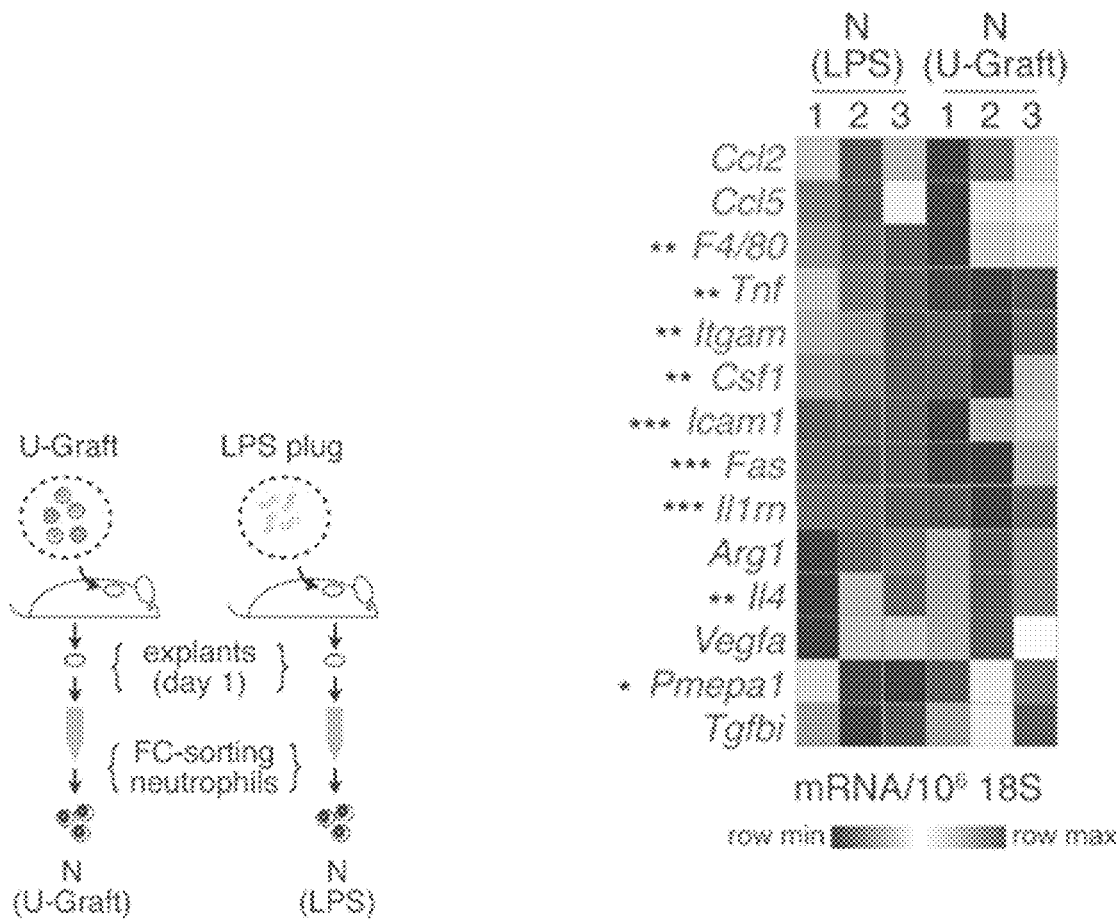
FIG. 10A
FIG. 10B

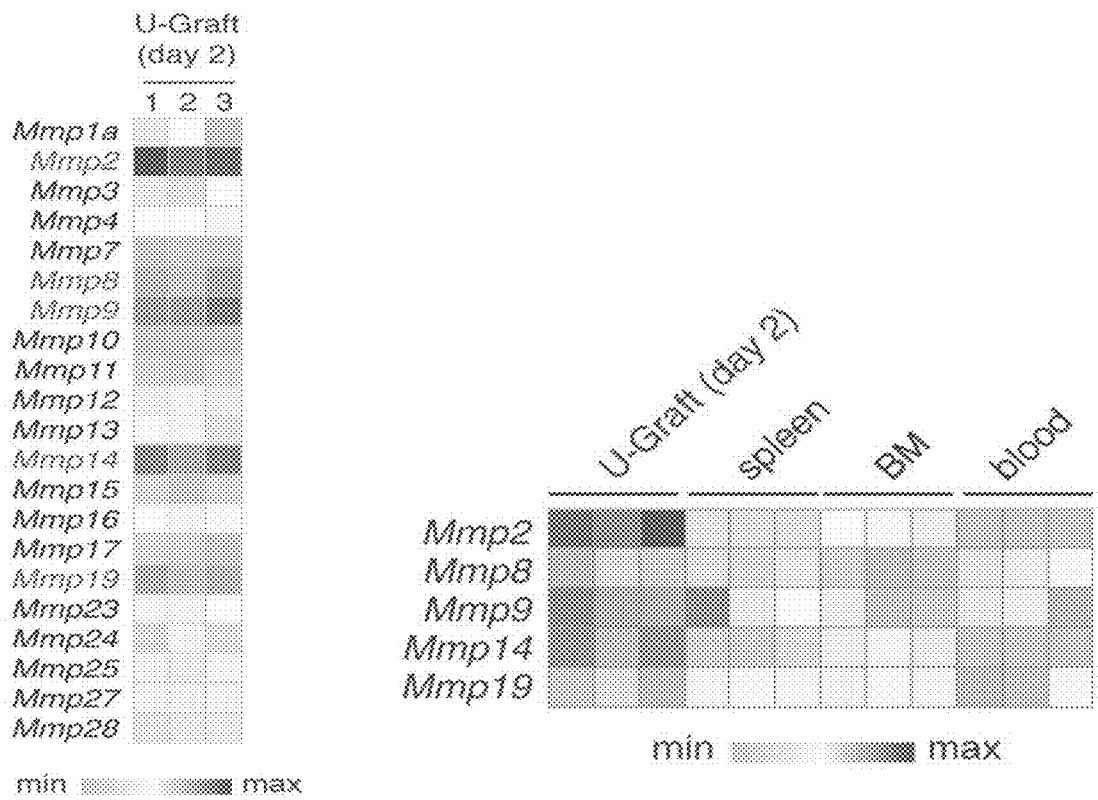
FIG. 11A
FIG. 11B
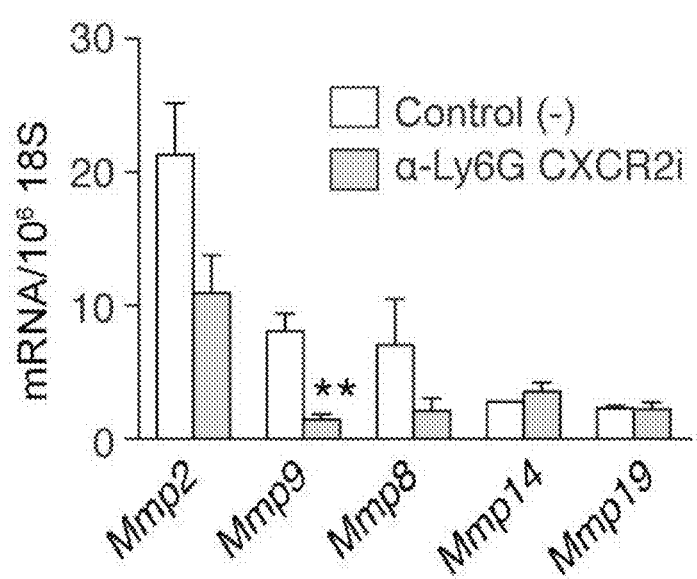
FIG. 11C

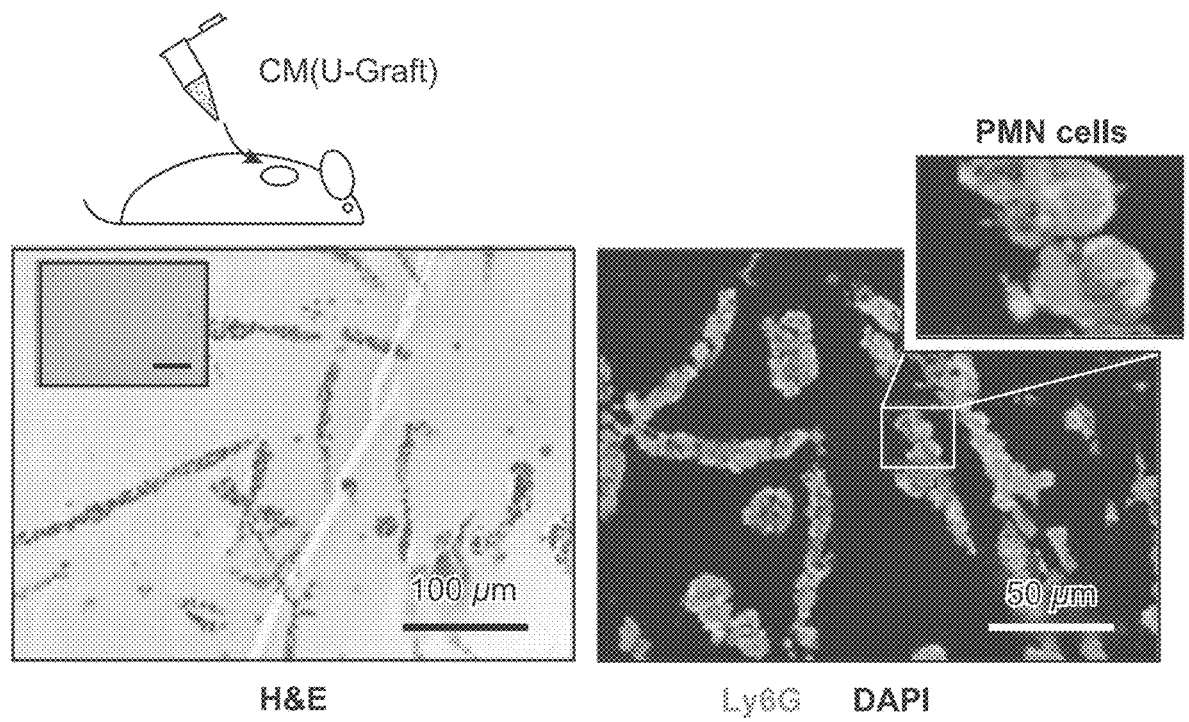
FIG. 12B
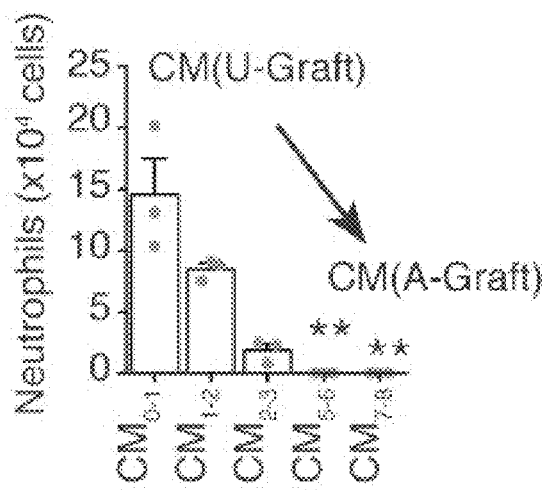
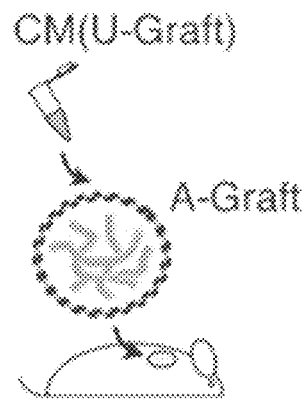
FIG. 12C  FIG. 12D

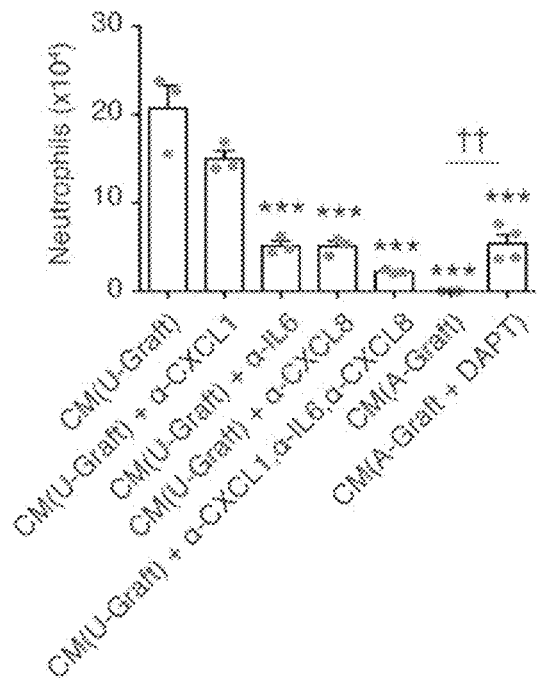
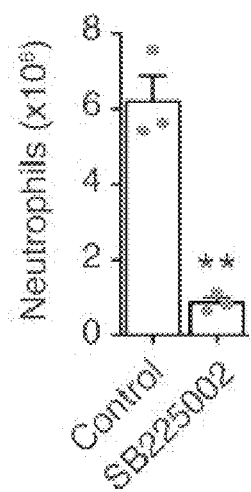
FIG. 14D
FIG. 14E
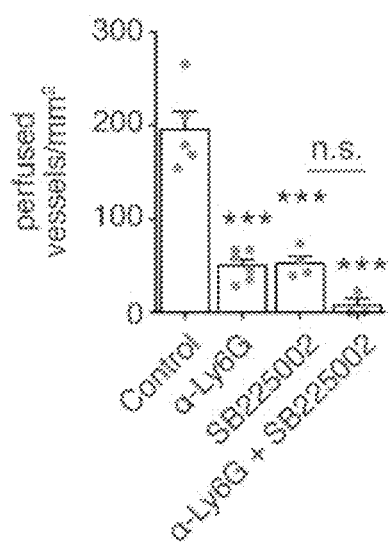
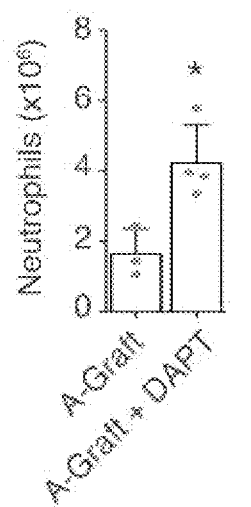
FIG. 14F
FIG. 14G

▷ β-cells
▶ Perfused vessels

SEQUENCE LISTING

<160> NUMBER OF SEQ ID NOS: 90

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcttctgggc ctgctgttc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacaccactc cctgctgctt                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccgatgggt tgtaccttgt                                                   20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgggatcag cttgaaagg                                                    19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgctgccctt cttcgacat                                                    19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggcacccagc agaagttgtt                                                   20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgattctcc tggctgtga                                                  19

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccagctggag gaagttaaca tca                                             23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccacagtctg gcagttggaa                                                 20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcatctccc tggtatgtct tgc                                             23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagtccaagt ccacatcact gaa                                             23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaaagaccg attaaccatg tca                                             23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gctgagccac tacaagctgt ca                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cggtgtggtc tatgccatca                                                 20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
aacaacccat ttgatggacc taac                                            24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tgggagcatg gagatggata c                                               21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggtcttccgg tcctgctgt                                                  19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tcccagacag gccctgttc                                                  19

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
attggcttcg caaggagaga                                                      20

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgaaaacag caattgagaa agctt                                                25

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagacgtggg tcgattcca                                                       19

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttccaggaat tgagccacaa g                                                    21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggacgctggg agaagacaga                                                      20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccacactat cccaggagca ta                                                   22

<210> SEQ ID NO 25
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatgccatta ccagtctccg a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccttccgag tatgggagag t                                              21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tacactgaga agctgggctg gta                                            23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcagtatttc aatgtggagg tttg                                           24

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctccatcat gcaaccgtac t                                              21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactgacctt agccgctacc cta                                            23

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaacgtccc agtgacctca                                                    20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggatcccagt cactggtgtg t                                                  21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cctagatggc cgaatcatcc t                                                  21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatggtcctc tgggagtcct t                                                  21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agcctctggg acgctcagt                                                     19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggtccacc agtttgaatg                                                    20

<210> SEQ ID NO 37
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
gctgcctctg ctctcctcag t                                              21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atgagcatag gattccgaga gtg                                            23

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcagcgagtg catgaacga                                                 19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
accagcccaa ctccaagct                                                 19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctgcccttac aggaacagaa gag                                            23

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggcagaaaac aacctgaacc tt                                             22

<210> SEQ ID NO 43
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
cacctggccc aggagtttc                                                  19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcctaacggc ctgcctagt                                                  19

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgtctcaaag attaagccat gca                                             23

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtgaatgagt agcagcaggt gagt                                            24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgctgctggt gtagaaatac tcctt                                           25

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtgggtgagg agcacgtagt c                                               21

<210> SEQ ID NO 49
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 49
tggaaggtca cactgaattc tctta                                              25

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttctgacacc tccttggcaa t                                                  21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcctcccagc tccaggtata t                                                  21

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cacggctcaa gggttccat                                                     19

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctggacaggc agctgactca                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcatccaccc aaatgacaca                                                    20

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic

```
                                  primer

<400> SEQUENCE: 55
gtgcatgtag gtattgtggt tctga                                              25

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tggctcagta ctacgagtaa tc                                                 22

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggctttctgg attaaggact gttc                                               24

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttccgaggac agtccatcgt                                                    20

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccagctcatc tcctcgttct tg                                                 22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgttggtcca cgtctcatca ag                                                 22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 61
aagtgagaat ctcccccaac ac                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atcatcatcc cttgcactgt ca                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcctcgaagt tactgccgtc ta                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgaaggcat gacctagagt gt                                              22

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgttgatgtc tgcttctccc tgta                                            24

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tcgcggcaag tcttcagagt                                                 20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 67
gaactgtgat gatcctcgga aga                                              23

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gccggacttg ctcccttac                                                   19

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtgggtcaaa gacagctgca t                                                21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gagctcagcc tcaacctgct                                                  20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcatgtccct cccggatgt                                                   19

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gtgtgacctg ctcccacact t                                                21

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agcgcagcac tgacattctg                                           20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acgcaccctg tcctcatagg                                           20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gagggtcggt ctggcactc                                            19

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtggtgcact gcagagacca                                           20

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgatcaggga cgccacatc                                            19

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caagctgtcg ttcctggaac a                                         21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
ggctatccat gtttcatctt cgt                                              23

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgtctgctct gggagttgtg                                                  20

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccgcagaggg ttgtattggt t                                                21

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcattgggag acagtaagtg gaa                                              23

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaggagtcca ggccttcca                                                   19

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ttgatctggg tcatgcagtt g                                                21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggctttgctg tgcttcaggt a                                                21
```

```
<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tctcctaagt gatgctcaaa cacat                                              25

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggcaagtctc ctcattgaat cc                                                 22

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agtacacagc cttgttgcca tgt                                                23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gggtgaactg ctggtattct cat                                                23

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcgaccaaag gaaccataac tg                                                 22
```

METHODS TO ENHANCE MICROVASCULAR ENGRAFTMENT OF BIOENGINEERED AND PRIMARY TISSUES

CLAIM OF PRIORITY

This application is a § 371 U.S. National Phase Application of International Patent Application No. PCT/US2017/062396, filed on Nov. 17, 2017, which claims the benefit of U.S. Provisional Application Ser. No. 62/423,540, filed Nov. 17, 2016, and U.S. Provisional Application Ser. No. 62/506,391, filed May 15, 2017. The entire contents of the forgoing are hereby incorporated by reference.

FEDERALLY SPONSORED RESEARCH OR DEVELOPMENT

This invention was made with government support under Grant Number AI123883 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 10, 2017, is named 37314-0054WO1_SL.txt and is 20,648 bytes in size.

TECHNICAL FIELD

Described herein are methods for tissue grafting, and more particularly methods for enhancing tissue graft revascularization, e.g., host engagement of pre-existing graft blood vessels.

BACKGROUND

Tissue engineering holds great promise in regenerative medicine as a solution to the increasing demand for donor organs and tissues[1]. In this context, bioengineering functional vascular networks is central[2,3]. The last decade has seen remarkable progress in our collective effort to bioengineer such networks by self-assembly of vascular cells within suitable biomaterials[4-9]. However, efforts remain mostly empirical due in large part to the inability of bioengineered microvessels to connect to the host circulatory system upon implantation. This challenge is similar to that of primary tissues during surgical grafting[10-14] Indeed clinical experience with primary tissues has repeatedly shown that inadequate revascularization remains a common outcome, leading to various degrees of graft resorption and failure[15,16]. Therefore, the search for new approaches to advance graft revascularization continues to be a pressing priority in regenerative medicine.

SUMMARY

The present invention is based, at least in part, on the discovery that engagement of host neutrophils, in particular non-inflammatory phenotype (type "N2") neutrophils, enhances tissue graft revascularization by secreted factors, such as chemokine (C-X-C motif) ligand 1 (CXCL1), chemokine (C-X-C motif) ligand 8 (CXCL8), and interleukin 6 (IL6). Re-vascularization of the tissue graft can also be achieved by inhibiting Notch signaling in the vasculature which leads to reactivation of the expression of several cytokines (most significantly CXCL1, CXCL8, and IL6). These results suggest a novel mechanism by which the pro-vascularization potential of neutrophils provides enhanced engraftment of bioengineered and primary tissues that could benefit millions of grafting procedures that rely on adequate revascularization.

Thus, provided herein are methods of preventing, inhibiting or reducing inadequate revascularization, or inefficient engraftment, in an implanted tissue graft, the method comprising: contacting a tissue graft with a Notch inhibitor, unassembled vascular cells, conditioned medium from unassembled vascular cells, ex vivo stimulated-neutrophils, or any combination thereof, for 0 to 48 hours.

In some embodiments, contacting the tissue graft is prior to tissue graft implantation, at the same time as tissue graft implantation, following tissue graft implantation, or any combination thereof.

In some embodiments, the Notch inhibitor is a γ-secretase inhibitor.

In some embodiments, the Notch inhibitor is a small molecule, an antisense molecule, a small interfering RNA, or a small hairpin RNA which is specific for a nucleic acid encoding any one of human NOTCH1, NOTCH2, NOTCH3, Notch ligand 4 (DLL4), hairy and enhancer of split 1 (HES1), hes family bHLH transcription factor 5 (HES5), hes related family bHLH transcription factor with YRPW motif 1 (HEY1), or hes related family bHLH transcription factor with YRPW motif 2 (HEY2).

In some embodiments, the Notch inhibitor is an antibody or antigen binding portion thereof that is specific for and inhibits the activity of a human NOTCH1, NOTCH2, NOTCH3, Notch ligand 4 (DLL4), hairy and enhancer of split 1 (HES1), hes family bHLH transcription factor 5 (HES5), hes related family bHLH transcription factor with YRPW motif 1 (REY1), or hes related family bHLH transcription factor with YRPW motif 2 (HEY2) polypeptide.

In some embodiments, the unassembled vascular cells comprise a plurality of endothelial cells (EC) and mesenchymal stem cells (MSC), preferably wherein the plurality of EC and MSC are in a ratio of EC:MSC of about 1 to 10. In some embodiments, the ratio of EC:MSC is about 1:1.

In some embodiments, the unassembled vascular cells comprise a plurality of EC and MSC, preferably wherein the plurality of EC and MSC are in a ratio of EC:MSC of about 10 to 1 (e.g., about 9 to 1, about 8 to 1, about 7 to 1, about 6 to 1, about 5 to 1, about 4 to 1, about 3 to 1 or about 2 to 1). In some embodiments, the conditioned medium is collected daily over about 1 to 10 days.

In some embodiments, the conditioned medium comprises an increased concentration of cytokines with non-inflammatory neutrophil chemoattractant activity.

In some embodiments, the conditioned medium comprises chemokine (C-X-C motif) ligand 1 (CXCL1), chemokine (C-X-C motif) ligand 8 (CXCL8), or interleukin 6 (IL6), or any combination thereof.

In some embodiments, the unassembled vascular cells are embedded in a hydrogel or cultured on top of hydrogel-coated cell culturing plates.

In some embodiments, the hydrogel is a collagen gel, a fibrin gel, a gelatin-based hydrogel, or any combination thereof.

In some embodiments, the hydrogel further comprises fibronectin or another cross-linking protein.

In some embodiments, the hydrogel controls release of factors secreted by the unassembled vascular cells.

In some embodiments, the tissue graft is a pancreatic islet tissue graft. In some embodiments, the tissue graft is a bioengineered graft or a primary tissue graft.

As used herein, the terms "native tissue" and "primary tissue" are used interchangeably, and mean tissues obtained from a living subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 9A-F. Adoptive transfer of F4/80+ cells. Bone marrow cells were obtained by flashing the femur of nude mice. Neutrophils were then purified using a murine neutrophil selection kit (Miltenyi Biotec). A. Donor mF4/80+ cells were isolated from bone marrow by magnetic-activated cell sorting (MACS) using magnetic beads coated with anti-mF4/80 antibodies. Flow cytometry panels depict the proportion of mF4/80+ cells (mCD45+/mF4/80+ cells) (B) before (~18%) and (C) after (~97%) purification. D. Schematic with BM-F4/80+ cell adoptive transfer strategy. U-Graft implanted into irradiated mice and BM-F4/80+ cells simultaneously transferred from non-irradiated donors. (E) H&E and (F) immunohistochemical (hCD31+ cells) staining of U-Grafts explanted at day 7 from irradiated mice with BM-F4/80+ cell transfer.

FIGS. 10A-J. Alternatively polarized neutrophils mediate U-Graft vascularization. A. Schematic with neutrophils (N) isolated from either explanted U-Grafts or from lipopolysaccharide (LPS)-containing plugs. B. Heat map of gene expression levels (by qPCR) in neutrophils from U-Grafts and LPS plugs. Primers were mouse specific (Table 2). mRNA data are row-relative and normalized to ribosomal 18S rRNA. n=3 mice per group. * P<0.001,  P<0.01, * P<0.05 between U-Graft and LPS groups. C. Representative Ly6G+(red) neutrophils from U-Grafts and LPS plugs after exposure to gfp-E. coli (green). Phagocytosis of gfp-E. coli was visualized under a fluorescent microscope and quantified by flow cytometry. Bars represent normalized mean green fluorescence ±s.d. measured in gated Ly6G+neutrophils; n=3 mice per group.  P<0.01 between U-Graft and LPS groups. D. Macroscopic views of U-Grafts explanted at day 7 from: (i) non-irradiated mice, (ii) irradiated mice, (iii) irradiated mice+transfer of BM-LysM-Cre-neutrophils, and (iv) irradiate mice+transfer of BM-tgfbr2$^{-/-}$-neutrophils. E. H&E staining of U-Grafts explanted at day 7 from irradiated mice with transfer of either BM-LysM-Cre or BM-tgfbr2$^{-/-}$ neutrophils. Perfused vessels marked by arrowheads. F. Immunohistochemical (h-CD31$^+$ cells) staining of U-Grafts explanted at day 7 from irradiated mice with transfer of either BM-LysM-Cre or BM-tgfbr2$^{-/-}$ neutrophils. Perfused vessels marked by arrowheads. G. Microvessel density at day 7. Bars represent mean±s.d.; n=4 mice per group. * P<0.001, ** P<0.01 compared to non-irradiated control group. †P<0.05 and ††P<0.01 between indicated groups. (H-J) U-Grafts were implanted in mice treated with SB432542. Mice receiving saline injections served as controls. (H) H&E staining of explanted U-Grafts at day 7. (I) Immunofluorescent staining revealed the presence of human vessels (UEA-1+lumen) and perivascular coverage (α-SMA+ cells) in the control group; and non-perfused human endothelial cord structures in SB432542-treated grafts. (J) Microvessel density quantified at day 7. Bars represent mean±s.d.; n=4 mice per group. * P<0.05. Scale bars: 100 μm (e, f, h, i).

FIGS. 11A-H. Proteolytic activity of graft neutrophils. A. Heat map of metalloproteinases (MMPs) mRNA expression levels (by qPCR) in U-Grafts at day 2 B. Heat map of selected MMPs in U-Grafts and other control tissues. C. Expression of selected MMPs in U-Grafts explanted from control (−) and neutrophil-depleted (α-Ly6G/CXCR2i) mice at day 2. Primers were mouse specific (Table 2). mRNA data were normalized to ribosomal 18S rRNA. Bars represent mean±s.d.; n=3 mice per group.  P<0.01. D. Gelatinases (MMP2, MMP9) activity measured by zymography in media conditioned by U-Grafts explanted at day 2 from (i) control, (ii) neutrophil (N)-depleted, and monocyte (M)-depleted mice. E. Imaging of explanted U-Grafts using a protease activatable fluorescent MMP-Sense probe. Active MMPs (green) visualized at day 2 in conjunction with infiltrated Ly6G+(red) neutrophils. Nuclei stained by DAPI. F. H&E staining of U-Grafts at day 2. Network of channels populated by polymorphonuclear cells (arrowheads). G. Immunofluorescent staining of human h-vimentin+ cells (green), Ly6G+ neutrophils (red) and collagen (magenta) in U-Grafts at day 2. Channels revealed by absence of collagen. Nuclei stained by DAPI. H. Immunofluorescent staining of human h-vimentin+ cells (green) and Ly6G+ neutrophils (red) in U-Grafts explanted at day 2 from control and neutrophil (N)-depleted mice. Nuclei stained by DAPI. Degree of human cell spreading measured as inverse circularity by image analysis. Data from >140 cells per graft, represented as box and whiskers (10-90 percentile); n=3 grafts per group. * P<0.001. Scale bars: 100 μm (E left, F, G, H), 50 μm (E right).

FIGS. 14A-K. Notch inhibition promotes A-Graft revascularization. (A) mRNA gene expression (by qPCR) of NOTCH1 and selected downstream mediators of Notch signaling pathway (HEY1, HEY2, HES1, HES5). In vitro: data from ECFCs retrieved from U-Grafts and A-Grafts and normalized to ribosomal 18S rRNA. In vivo: data from total mRNA isolated from U-Grafts 30 min (day 0) and 7 days after implantation. Data normalized to human β-actin (ACTV). Bars represent mean±s.d.; n=3 grafts per group. *** P<0.001, * P<0.05. (B) Expression of CXCL1, CXCL8, and IL6 in ECFCs retrieved from U-Grafts and A-Grafts and normalized to ribosomal 18S rRNA. C. Human cytokine protein array analysis of conditioned media (CM) from U-Grafts, A-Grafts, and A-Grafts+DAPT (γ-secretase inhibitor; 24 h exposure). Selected cytokines marked with boxes. Quantification of cytokine levels were carried out by densitometry. D. Blocking neutrophil recruitment by neutralizing antibodies in subcutaneous plug assays. Neutralizing antibodies against IL6, CXCL8, and CXCL1 were added to CM(U-Grafts) prior to implantation. The number of neutrophils recruited into the plugs were measured by flow cytometry at day 2. Bars represent mean±s.d.; n=3-4 mice per group. * P<0.001 compared to CM(U-Grafts). (E, F) Effect of CXCR2 antagonist (SB225002) on neutrophil recruitment and U-Graft vascularization. U-Grafts implanted in untreated mice served as control. (E) Neutrophil recruitment into U-Graft at day 2 measured by flow cytometry. (F) Density of perfused microvessels at day 7. Bars represent mean±s.d.; n=3-6 mice per group. * P<0.001, ** P<0.01 compared to Control. (G) Neutrophil recruitment at day 2 in A-Grafts and A-Grafts+DAPT. Bars represent mean±s.d.; n=3-4 mice per group. * P<0.05. H. Macroscopic views of U-Grafts, A-Grafts, and A-Grafts+DAPT, explanted at day 7. (I) H&E and (J) immunohistochemical (h-CD31+ cells) staining of A-Grafts and A-Grafts+DAPT explanted at day 7. Perfused vessels identified as luminal structures containing RBCs (arrowheads). K. Microvessel density at day 7. Bars represent mean±s.d.; n=4 mice per group. *** P<0.001, * P<0.05 between indicated groups. Scale bars: 50 µm.

DETAILED DESCRIPTION

Figure 1A:
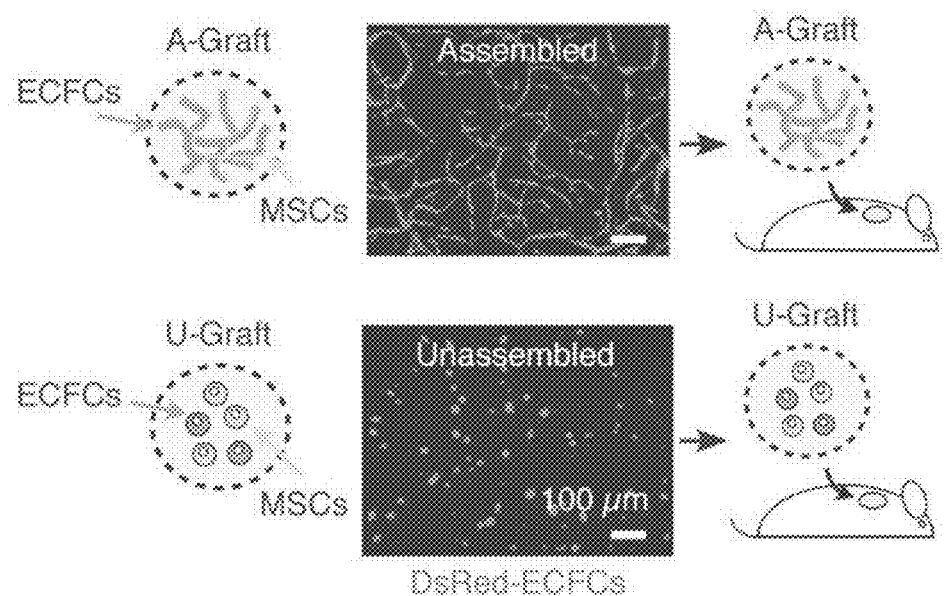
FIGS. 1A-H. Engraftment of bioengineered microvascular networks. A. Schematic of microvascular graft models. Grafts were prepared in vitro by combining human endothelial colony-forming cells (ECFCs) with MSCs in hydrogels and then surgically implanted into nude mice. Assembled vascular grafts (A-grafts) were created over 7 days in vitro, whereas unassembled grafts (U-grafts) contained a suspension of cells. B. H&E staining of A-Grafts and U-Grafts explanted after 7 days in vivo. Insets are macroscopic views of the explants. Perfused vessels were identified as luminal structures containing RBC (arrowheads). C. Immunohistochemical staining of h-CD31+ cells at day 7. Human h-CD31+ vascular structures were identified as either perfused (lumens containing RBC) or non-perfused (cord structures). D. Density of perfused human blood vessels at day 7. Bars represent mean±s.d.; n=4 mice per group. * $P<0.001$ between A-Grafts and U-Grafts. E. Time-course cytometric quantification of myeloid cell subpopulations in U-Grafts. F Cytometric quantification of neutrophils (N) and macrophages (MΦ) in U-Grafts and A-Grafts at day 2 post-implantation. Bars represent mean±s.d.; n=3 grafts per group.  $P<0.01$, * $P<0.05$ between A-Grafts and U-Grafts. Immunofluorescent staining of G, H. Ly6G+ neutrophils and (h) F4/80+ macrophages in U-Grafts and A-Grafts at day 2 post-implantation. Human cells visualized as h-vimentin+ cells. Nuclei stained by DAPI. Scale bars: 100 μm (B, C) and 50 μm (A, G, H)

The last decade has seen remarkable progress in vascular network bioengineering. However, bioengineered microvessels largely fail to form anastomoses with host vasculatures. As demonstrated herein, implants containing assembled human vascular networks (A-Grafts) failed to engraft due to their inability to engage non-inflammatory host neutrophils upon implantation into mice. In contrast, unassembled vascular cells (U-Grafts) readily engaged alternatively polarized neutrophils, which in turn served as mediators of vascular assembly and anastomosis. Indeed, depletion of host neutrophils entirely abrogated vascularization in U-Grafts, whereas an adoptive transfer of neutrophils fully restored vascularization in myeloid-depleted mice. Neutrophil engagement was regulated by secreted factors and was progressively silenced as the vasculature matured. Of note, exogenous addition of factors from U-Grafts reengaged neutrophils and enhanced revascularization in A-Grafts, a process that was recapitulated by blocking Notch signaling. Without wishing to be bound by theory, the present results provide evidence that harnessing the pro-vascularization potential of neutrophils is a successful strategy to improve engraftment of bioengineered tissues.

As shown herein, the present inventors sought to identify cellular mechanisms governing engraftment of bioengineered vascular networks. To this end, microvasculatures at two contrasting states of maturation were examined. On one hand, grafts were bioengineered containing fully-assembled vascular networks embedded in 3-dimensional hydrogel constructs (referred to as assembled grafts or A-grafts). These vascular networks mimicked the indolent state of mature microvessels and thus largely failed to spontaneously connect with the host circulation upon implantation. On the other hand, grafts were bioengineered by simply combining an unassembled suspension of vascular cells embedded in a hydrogel (referred to as unassembled grafts or U-Grafts), a configuration previously shown to effectively produce perfused networks of microvessels following implantation[17,18]. Without wishing to be bound by theory, by comparing these two distinct graft models, the inefficient engraftment of A-grafts was shown to be likely due to the inherent inability of their mature microvasculature to engage non-inflammatory host neutrophils, which in U-Grafts served as apparently indispensable mediators of vascularization.

The present inventors sought to determine the cellular mechanisms impairing engraftment of bioengineered mammalian, and particularly human, vascular networks. We showed that the inefficient formation of anastomoses in assembled microvessels (A-Grafts) is due to an inherent inability of mature vessels to engage a subset of alternatively polarized (non-inflammatory) host neutrophils at the implantation site. This was in contrast to grafts comprising a non-assembled suspension of vascular cells (U-Grafts), which rapidly engage neutrophils to mediate proper vascularization. Depletion of host neutrophils entirely abrogated vasculogenesis in U-Grafts, whereas an adoptive transfer of neutrophils restored vascularization in myeloid-depleted mice. The dependency on host neutrophils was complete and corroborated in both syngeneic (murine grafts implanted into mouse) and xenograft (human in mouse) models.

Neutrophil recruitment and activation were controlled by factors secreted from the transplanted vascular cells, a process initially upregulated in unassembled U-Grafts but progressively silenced as the vasculature matured. This mechanism of progressive neutrophil disengagement could explain the inactive nature of assembled microvasculatures—both bioengineered and primary—with regards to their capacity to engraft and connect with host vessels.

Emerging evidence indicate that neutrophils can comprise two distinct subpopulations with different polarized phenotypes: 1) a canonical pro-inflammatory phenotype (referred to as "N1"); and 2) an alternative anti-inflammatory, pro-remodeling, phenotype ("N2")[20,35,36] resembling the well-established "M1-M2" macrophage paradigm. N2 polarization has been substantiated in a variety of tumor models, and it involves TGFβ-mediated activation (TGFβ inhibition produces a shift to N1, and in turn acquisition of antitumor activity), followed by downregulation of pro-inflammatory genes and expression of both anti-inflammatory factors and proangiogenic mediators[20,21,37] Recently, the contribution of alternatively polarized N2 neutrophils has also been described in non-neoplastic events, including brain stroke[38] and myocardial infarction[39]. However, their participation in tissue grafting was not previously described. As shown herein, graft neutrophils displayed a phenotype that was consistent with the notion of an alternative N2 polarization in several respects including low expression of canonical pro-inflammatory genes, high expression of anti-inflammatory and pro-remodeling genes, low phagocytic activity, and TGFβR2-mediated activation. We also found that adoptive transfer of neutrophils from bone marrow restored vascularization in myeloid-depleted mice to a better extent than blood neutrophils, which is consistent with published evidence of immature non-inflammatory neutrophils (equivalent to "N2" neutrophils) being more abundant in the bone marrow than in circulation[21].

The present experiments focused on the role of neutrophils; however, the grafts also contained host macrophages and monocytes. The presence of macrophages was expected in light of their role as cellular chaperones for vascular anastomosis during angiogenesis[40]. Furthermore, macrophage-neutrophil interdependency during angiogenesis is well established[41-43]. In the present studies, the role of neutrophils in graft vascularization did not preclude participation of host macrophages, which were also abundant at the onset of perfusion. However, in the absence of neutrophils, macrophage involvement in vascularization was insufficient. With regard to host monocytes, the results were equally conclusive: depletion of circulating monocytes had no appreciable effect on graft vascularization and adoptive transfer of BM-derived F4/80+ cells could not restore normal vascularization activity in myeloid-depleted mice. Lastly, our results with α-Ly6G (neutrophil depletion)+ SB225002 (CXCR2 inhibitor) revealed that this combination reduced vascularization in U-Grafts more than either of the treatments separately. Nevertheless, the additional reduction in microvessel density with the combination treatment might indicate participation of an additional type of host CXCR2+ cells in vascularization, suggesting that neutrophils are likely not solely responsible for the vascularization of the grafts.

Prior to the present study, the mechanisms regulating engraftment of bioengineered microvessels remained essentially unexplored. Nevertheless, some recent studies did report positive integration between engineered and host vessels. Baranski and colleagues bioengineered vascular networks by the assembly of human ECs (HUVECs) and murine embryonic perivascular cells (10T1/2 cell line), and demonstrated perfusion with host blood upon implantation into the intraperitoneum of nude mice[44]. More recently, Riemenschneider et. al. constructed patches containing self-assembled microvessels formed by co-entrapment of ECFCs and human fetal brain pericytes in fibrin gel. These patches were sutured onto the epicardial surface of the hearts of athymic rats following permanent ligation of the left anterior descending artery; ~25% of the bioengineered vessels were found perfused[45]. Thus, the poor engraftment seen with our bioengineered vessels might seem inconsistent with these previous reports. However, it is important to note that the sources of perivascular cells in the aforementioned studies were embryonic and fetal tissues, respectively. Considering that xenograft studies have shown that embryonic (but not adult) vasculature can form spontaneous connections with the host[46], it is conceivable that the sole presence of fetal cells could facilitate the formation of anastomoses. In any case, bioengineering tissues with non-autologous fetal cells poses additional challenges related to immune tolerance and thus may have reduced translational potential. Further studies are warranted to elucidate if host neutrophils also mediate vascular anastomoses in bioengineered vessels that use embryonic/fetal cells.

Harnessing the pro-vascularization potential of neutrophils provides the basis for a new strategy to engraft bioengineered and primary tissues that could benefit millions of grafting procedures that rely on adequate revascularization. Clinical and preclinical studies have repeatedly shown that perfused vessels in primary adult grafts are almost exclusively originated by infiltration of host vessels. However, this process of revascularization poses two main constraints on the grafts: (1) inadequate blood supply to the center, which leads to necrosis and resorption; and (2) irreversible loss of graft endogenous vasculature. The latter is important because mounting evidence indicates that most tissues have highly specialized endothelium that regulates homeostatic and regenerative processes in a tissue-specific manner[47-51]. Thus, loss of endogenous vessels could contribute to long-term malfunctioning of the grafts. Enabling a robust integration of the graft microvasculature would eliminate the aforementioned constraints and thus could have pronounced clinical significance. In light of the present disclosure, new strategies focus on harnessing non-inflammatory neutrophils by exposing grafts to specific exogenous vascular factors and/or blocking Notch signaling, which would reactivate endogenous mechanisms in mature vessels.

Tissue Transplantation

As described herein, "tissue grafting" or "surgical grafting" refers to any tissue that is moved to a new anatomical site, and that in some embodiments is not an intact organ or does not include an anastomosable vessel. In some embodiments, the tissue may be pancreatic islets, adipose tissue, bone, e.g., iliac crest corticocancellous bone, nerves, or blood vessels. In some embodiments, the tissue is not a vascularized tissue that can be anastomosed. In some embodiments, the graft is allogeneic, i.e., a graft of tissue between genetically non-identical individuals of the same species. In some embodiments, the graft is autologous, i.e., a graft of tissue taken from the recipient subject's own body. In some embodiments, the graft is bioengineered. Methods for constructing bioengineered grafts are well known in the art. See e.g., Ahsan, T. and Nerem, R M. Orthod Craniofac Res 2005, 8(3): 134-140; Atala, A. Pediatric Research 2008, 63: 569-575; and Jungebluth, P. et al. Biomaterials 2013, 34(16): 4057-4067.

Methods of Treatment

Described herein are methods that can include manipulating the NOTCH pathway for preventing, inhibiting or reducing inadequate revascularization, or inefficient engraftment, in an implanted tissue graft. In general, the present methods can be performed in any animal subject, e.g., a mammalian subject, e.g., a human or non-human mammal.

The methods described herein include methods for the treatment or prophylaxis (reduction of risk of developing) of graft resorption and failure, as a result of inadequate revascularization. Also described herein are methods of preventing, inhibiting or reducing inadequate revascularization, or inefficient engraftment, in an implanted tissue graft. In some embodiments, the method of preventing, inhibiting or reducing inadequate revascularization comprises contacting a tissue graft with a Notch inhibitor. In some embodiments, the method of preventing, inhibiting or reducing inadequate revascularization comprises contacting a tissue graft with unassembled vascular cells. In some embodiments, the method of preventing, inhibiting or reducing adequate revascularization comprises contacting a tissue graft with conditioned medium from unassembled vascular cells. In some embodiments, the method of preventing, inhibiting or reducing inadequate revascularization comprises not contacting a tissue graft with an inhibitor of the TGF-β type I receptor (e.g., SB432542).

Ex Vivo-Stimulated Neutrophils

In some embodiments, the methods of preventing, inhibiting or reducing adequate revascularization comprise contacting a tissue graft with ex vivo-stimulated neutrophils. In some embodiments, the neutrophils have been first harvested from a donor (e.g., from bone marrow and/or blood; autologous or allogeneic donor), then pretreated ex vivo to become non-inflammatory "N2" neutrophils prior to being applied to the graft. N2 neutrophils are characterized by high levels of expression of arginase, CCL2 and CCL5 chemokines, and by the ability to inhibit effector T-cells, see, e.g., Fridlander et al., Cancer Cell. 2009 Sep. 8; 16(3):183-94; Eruslanov et al., J Clin Invest. 2014; 124(12):5466-5480; Perobelli et al., Braz J Med Biol Res. 2015 August; 48(8): 665-675. Ex vivo-stimulation of neutrophils can be performed by methods that include incubating bone marrow- or blood-derived neutrophils with either 1) conditioned medium from unassembled vascular cells (U-grafts) for 0-48 hours; and/or 2) 1-100 ng/mL of recombinant TGFβ-1, -2, and -3 for 0-48 hours. Donor neutrophils can be isolated from either bone marrow aspirates or peripheral blood by methods routinely used in the art, such as by using a neutrophil isolation kit (Miltenyi Biotec). Recombinant TGFβ-1, -2, and -3-stimulated neutrophils can be prepared according to the method outlined below. Briefly, 1-100 ng/mL of recombinant TGFβ-1, -2, and -3 is used to stimulate about $10^7$ neutrophils. Finally, $10^7$ stimulated-neutrophils can be used to treat (by simple contact, e.g., for at least one minute up to and beyond 24 hours, e.g., long enough to encourage the development of the N2 phenotype) a single tissue graft of approximately 200 μL of volume.

Unassembled Vascular Cells

As used herein, "unassembled vascular cells" refers to a population of cells comprising a plurality of endothelial cells (EC) and mesenchymal stem cells (MSC). In some embodiments, the plurality of EC and MSC are in a ratio of EC:MSC that is about 1 to 100; e.g., about 1 to 95, about 1 to 90, about 1 to 85, about 1 to 80, about 1 to 75, about 1 to 70, about 1 to 65, about 1 to 60, about 1 to 55, about 1 to 50, about 1 to 45, about 1 to 40, about 1 to 35, about 1 to 30, about 1 to 25, about 1 to 20, about 1 to 15, about 1 to 10, about 1 to 5, about 1 to 4, about 1 to 3, about 1 to 2, or about 1 to 1.

The unassembled vascular cells provided herein can include at least $1 \times 10^1$, at least $1 \times 10^2$, at least $1 \times 10^3$, at least $1 \times 10^4$, at least $1 \times 10^5$, at least $1 \times 10^6$ cells, at least $1 \times 10^7$ cells, or at least $1 \times 10^8$ cells.

Secreted Factors

As described herein, subcutaneous plugs containing conditioned medium from unassembled vascular cells, collected daily over 8 days in vitro (or until the unassembled vascular cells differentiated into assembled cells), not only engaged host neutrophils, but also robustly recruited neutrophils in nude mice. This neutrophil recruitment was mediated by secreted factors, such as chemokine (C-X-C motif) ligand 1 (CXCL1), chemokine (C-X-C motif) ligand 8 (CXCL8), and interleukin 6 (IL6). Indeed, the collected conditioned medium comprised an increased concentration of cytokines with non-inflammatory neutrophil chemoattractant activity, e.g., CXCL1, CXCL8, and IL6. Thus, the methods described herein can include incubation of a tissue graft with a therapeutically effective amount of secreted factors to prevent, inhibit or reduce inadequate revascularization, or inefficient engraftment, in an implanted tissue graft. In some embodiments, these secreted factors engage and recruit anti-inflammatory, pro-remodeling, type "N2", neutrophils. In some embodiments, these secreted factors include one or more of CXCL1, CXCL8, and IL6, or any combination thereof. In some embodiments, these secreted factors are obtained from cells recombinantly expressing these secreted factors. In some embodiments, these secreted factors were enriched for in the conditioned medium collected from unassembled vascular cells, as described herein.

In some embodiments, the method of preventing, inhibiting or reducing inadequate revascularization comprises contacting a tissue graft with conditioned medium from unassembled vascular cells for 0 to 48 hours. The conditioned medium from unassembled vascular cells can be contacted with a tissue graft, e.g., for 0 to 24 hours.

Methods also provided herein include collecting conditioned medium from cultured unassembled vascular cells, e.g., daily, over about 1 to 10 days, e.g., about 2 to 8 days. In some embodiments, the conditioned medium from unassembled vascular cells is collected daily over about 8 days. In some embodiments, the collected conditioned medium is pooled and concentrated before contacting with a tissue graft. For example, $4 \times 10^5$ unassembled vascular cells are used to condition 500 μL of medium. Next, the 500 μL of conditioned medium is concentrated to 50 μL (10×). Then, the 50 μL of concentrated conditioned medium is used to stimulate $10^7$ neutrophils. Finally, $10^7$ stimulated-neutrophils are used to treat (by simple contact) a single tissue graft of approximately 200 μL of volume.

Notch Signaling Pathway Inhibitors

The methods described herein include incubation of a tissue graft with a therapeutically effective amount of a Notch signaling pathway inhibitor to prevent, inhibit or reduce inadequate revascularization, or inefficient engraftment, in an implanted tissue graft. The inhibitors that are useful in the present methods include those that act directly on the Notch signaling pathway, such as small molecule inhibitors (e.g., DAPT), antibody inhibitors of Notch activity, and stapled peptides (e.g., SAHM1 (Moellering, et al. Nature 2009; 462: 182-188; and Walenksy, et al. Science 2004; 305: 1466-1470)). In some embodiments, the Notch signaling pathway inhibitor is a decoy Notch-1 Fc peptide, or inducible genetic ablation of Notch. In some embodiments the inhibitor is a γ-secretase inhibitor (GSI) (Orian-Rousseau, etl al. Eur J Cancer 2010; 46: 1271-1277; and Lewis, et al. Bioorg Med Chem Lett 2005; 15:373-378). Examples of γ-secretase inhibitors include, but are not limited to: N—[N-(3,5-Difluorophenylacetyl-L-alanyl)]-S-phenylglycine t-Butyl ester (DAPT), compound E ((s,s)-2-(3,5-Difluorophenyl)-acetylamino]-N-(1-methyl-2-oxo-5-phenyl-2,3-dihydro-1H-benzo[e][1,4]diazepin-3-yl)-propionamide, diazepine-type structures (e.g., dibenzazepine), JLK6 (7-amino-4-chloro-3-methoxyisocoumarin), or compound 18 ([11-endo]-N-(5,6,7,8,9,10-hexahydro-6,9-methano benzo[9][8]annulen-11-yl)-thiophene-2-sulfonamide) (Fan, et al. Cancer Res. 2006; 66: 7445-7452. In some embodiments, the inhibitor is an alpha-secretase inhibitor (ASI) (Brou, et al. Mol Cell. 2000; 5:207-216; and Hartmann, et al. Hum Mol Genet. 2002; 11: 2615-2624). In some embodiment, the inhibitor is an antibody blocking Notch, its ligands, or receptor signaling, such as antibodies to Notch-3 and anti-negative regulatory region (NRR). (Li, et al. J Biol Chem 2008; 283(12): 8046-54; and Wu, et al. Nature 2010; 464: 1052-1057). In some embodiments, the inhibitor comprises the delivery of a gene or pseudogene encoding a Notch-inhibiting protein or peptide (Maillard, et al. Blood 2004; 104: 1696-1702). In some embodiments, the inhibitor is an agent that up-regulates the expression of endogenous Notch-inhibiting genes, e.g., Numb/Numb-like or FBXW-7 genes (Tsunematsu, et al. J Biol. Chem 2004; 279: 9417-423).

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the Notch target nucleic acid and modulate its function. In some embodiments, the Notch inhibitor is a small molecule, an antisense molecule, an antibody or antigen-binding fragment thereof, a small interfering RNA, or a small hairpin RNA that is specific for and reduces activity and/or levels of human NOTCH1, NOTCH2, NOTCH3, Notch ligand 4 (DLL4), hairy and enhancer of split 1 (HES1), hes family bHLH transcription factor 5 (HES5), hes related family bHLH transcription factor with YRPW motif 1 (REY1), or hes related family bHLH transcription factor with YRPW motif 2 (HEY2) (see Table 3).

TABLE 3

Exemplary sequences of NOTCH related genes

| | GenBank Accession No. (mRNA) | GenBank Accession No. (protein) |
|---|---|---|
| NOTCH 1 | No. NM_017617.4 | NP_060087.3 |
| NOTCH 2 | NM_001200001.1 | NP_001186930.1 |
| NOTCH 3 | NM_000435.2 | NP_000426.2 |
| DLL4 | NM_019074.3 | NP_061947.1 |
| HES1 | NM_005524.3 | NP_005515.1 |
| HES5 | NM_001010926.3 | NP_001010926.1 |
| HEY1 | NM_001040708.1 | NP_001035798.1 |
| HEY2 | NM_012259.2 | NP_036391.1 |

In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the Ablim3 sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30 60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity (i.e., they do not bind to other transcripts sufficiently to produce any significant undesirable off-target effects), to give the desired effect.

siRNA/shRNA

In some embodiments, the nucleic acid sequence that is complementary to an Ablim3 RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIES 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 rnM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH$,~$N(CH_3)$~O~$CH_2$ (known as a methylene(methylimino) or MMI backbone], $CH_2$—O—N ($CH_3$)—$CH_2$, $CH_2$—$N(CH_3)$—$N(CH_3)$—$CH_2$ and O—N ($CH_3$)—$CH_2$—$CH_2$ backbones, wherein the native phosphodiester backbone is represented as O— P— O— $CH_1$); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$OCH$_3$, OCH$_3$—O (CH$_2$)$_n$ CH$_3$, O(CH$_2$)$_n$ NH$_2$ or O(CH$_2$)$_n$CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH3), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34: e60 (2006); McTigue et al., Biochemistry 43:5388-405 (2004); and Levin et al., Nuc. Acids. Res. 34: e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30 60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-0-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Hydrogel

Described herein are methods that comprise the use of unassembled vascular cells, wherein the unassembled vascular cells can be embedded in a hydrogel or cultured on top of hydrogel-coated cell culturing plates. In some embodiments, the hydrogel is a collagen gel, a fibrin gel, a gelatin-based hydrogel, or any combination thereof. In some embodiments, the hydrogel comprises fibronectin. In other embodiments, the hydrogel is slow-releasing. See, e.g., Li and Mooney, Nature Reviews Materials 1, Article number: 16071 (2016) doi:10.1038/natrevmats.2016.71.

Pharmaceutical Compositions

The Notch inhibitor described herein can be further incorporated into a pharmaceutical composition. Such compositions typically include the Notch inhibitor and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include oral or parenteral, e.g., intravenous, intradermal, subcutaneous, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, e.g., tromethamine; and agents for the adjustment of tonicity such as sodium chloride or dextrose. pH can be adjusted with acids or bases, such as hydrochloric acid or sodium hydroxide.

The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water,

EXAMPLES

The invention is further described in the following examples, which do not limit the scope of the invention described in the claims.
Materials and Methods The following materials and methods were used in the Examples set forth below.
Mice Nu/nu males (Massachusetts General Hospital) were used for implantation unless stated otherwise. Rosa26$^{fsTrap}$ and Cdh5(Pac)-CreERT2+ transgenic mice (Zhou, et al. Proc. Natl. Acad. Sci. USA 110: 15395-15400 (2013); Wang, et al. Nature 465:483-486 (2010)) were interbred and offspring were given two consecutive intragastric injections of 50 µl tamoxifen (2 mg/ml in sunflower seed oil) on postnatal day P1 and P2 to induce Cre recombinase activity. The resulting Rosa26$^{fsTrap}$;Cdh5(Pac)-CreERT2+ mice served as donors and their tissues expressed eGFP-L10a fusion protein in endothelial cells. For myeloid-specific tgfbr2 deletions, LysM-Cre transgenic mice (Jackson Laboratory, JAX004781) were interbred with conditional Tgfbr2$^{lox/lox}$ mutants (JAX012603). The offspring were interbred again and genotyped to select homozygous tgfbr2$^{-/-}$ (LysM-Cre$^{+/+}$ Tgfbr2$^{lox/lox}$) alleles. The myeloid-specific deletions of tgfbr2 were confirmed by PCR. FVB/N-Tg(Tie2-gfp) mice (Jackson Laboratories, JAX003658) were used for isolation of pancreatic islets. Animal experiments were conducted under a protocol approved by the Institutional Animal Care and Use Committee at Children's Hospital Boston in an AAALAC-approved facility.
Implantation of Primary Murine Grafts 6-weeks-old Rosa26$^{fsTrap}$;Cdh5(Pac)-CreERT2+ transgenic mice served as donors and were perfused with PBS before being euthanized. Myocardium, liver and kidney were harvested and trimmed into 3×3×3 mm³ grafts. Tissue grafts were then surgically implanted into subcutaneous space on the back of nude mice with 50-µL of collagen-fibrin gel (3 mg/mL of bovine collagen, 30 ug/mL of human fibronectin, 25 mM HEPES, 10% 10×DMEM, 10% FBS, and 3 mg/mL of fibrinogen, pH neutral; mixed with 10 µL of 10 U/mL thrombin immediately before implantation). After 7 days in vivo, fluorescein isothiocyanate (FITC)-conjugated Griffonia Simplicifolia Lectin I (GSL I) isolectin B4 in saline (Iso-B4; 50 µg/100 µL/mouse) was infused intravenously 10 min before euthanasia. Grafts were explanted and subjected to histological analyses. Anti-FITC and anti-GFP antibodies were used to stain perfused and donor vessels, respectively.
Implantation of Primary Human Myocardial Grafts Discarded normal human right ventricular myocardial tissues were obtained during clinically-indicated procedures in accordance with an Institutional Review Board-approved protocol. Myocardial tissues were immediately transported to the laboratory in cold sterile saline, trimmed into 3×3×3 mm³ cubes, and surgically implanted (subcutaneously) into nude mice. 50-µL of collagen-fibrin gel was added around myocardial grafts to improve integration with host tissues. 7 days after implantation, FITC-conjugated Ulex Europaeus Agglutinin-I in saline (UEA-I; 50 µg/100 µL/mouse) was infused intravenously 10 min before euthanasia. Grafts were explanted and subjected to histological analyses. Perfused human vessels were stained by biotinylated-anti UEA-I antibody and streptavidin-TexasRed.
Isolation and Culture of Human MSCs and ECFCs Human MSCs were isolated from the mononuclear cell fraction of bone marrow aspirates as previously described (Melero-Martin, et al. Circ. Res. 103:194-202 (2008)). MSCs were cultured on uncoated plates using MSC-medium: MSCGM (Lonza) supplemented with 10% MSC-qualified FBS (Hyclone), 1× glutamine-penicillin-streptomycin (GPS; Invitrogen). All experiments were carried out with MSCs between passages 6-10. Human ECFCs were isolated from umbilical cord blood samples in accordance with an Institutional Review Board-approved protocol as previously described (Melero-Martin, et al. Blood 109: 4761-4768 (2007)). ECFCs were cultured on 1% gelatin-coated plates using ECFC-medium: EGM-2 (except for hydrocortisone; Lonza) supplemented with 20% FBS, 1×GPS. All experiments were carried out with ECFCs between passages 6-8. DsRed-labeled ECFCs were generated by retroviral infection with a pLVX-DsRed vector and selected with puromycin (2 µg/mL) (Chen, et al. Adv. Funct. Mater. 22: 2027-2039 (2012)).
Fabrication and Implantation of Bioengineered Grafts Photopolymerizable methacrylated gelatin (GelMA) hydrogel was synthesized as previously described (Chen, et al. Adv. Funct. Mater. 22: 2027-2039 (2012)). GelMA prepolymer solution was prepared in PBS at 80° C. (5 w/v % final) with photoinitiator Irgacure 2959 (0.5 w/v %; CIBA Chemicals), and then allowed to cool down to 37° C. in a water bath. ECFCs and MSCs (4×10⁵ total; 1:1 ratio) were suspended in 200 µL of GelMA solution and the mixture was polymerized by exposure to 7.5 mW/cm² UV light for 15 s at 37° C. Polymerized cell-laden constructs were referred to as unassembled grafts or U-Grafts. Alternatively, on indicated experiments, U-Grafts were constructed with ice-cold Phenol Red-free Matrigel (BD Bioscience). Assembled grafts or A-Grafts were constructed by culturing U-Grafts in vitro for 7 days using EGM2 with κ% FBS. A-Grafts contained easily observable, fully-assembled vascular networks. Both, U-Grafts and A-Grafts were subcutaneously implanted into back of 6-week-old male athymic nu/nu mice for engraftment studies. On specified experiments, DsRed-labeled ECFCs were used to visualize the formation of assembled vascular networks in A-Grafts. For Notch signaling inhibition studies, A-Grafts were treated with the γ-secretase inhibitor DATP (10 µM in EGM2 with 5% FBS) for 24 h prior to implantation; A-Grafts cultured for 8 days in EGM2 with 5% FBS served as a control. To evaluate host myeloid cell recruitment, grafts were explanted two days after implantation and subjected to flow cytometric and histological analyses. To assess vascularization, grafts were explanted 7 days after implantation and were subjected to histological analysis. On indicated experiments, FITC-conjugated UEA-I (50 µg/100 µL per mouse) was injected intravenously 10 min before euthanasia to label perfused human vessels.
Isolation and Culture of Murine MSCs and ECs Subcutaneous white fat pads were excised from euthanized C57BL/6 mice, minced, and digested (1 mg/mL collagenase A, 2.5 U/mL dispase, 126 µM calcium chloride, and 80 µM magnesium sulfate in DMEM containing 1% FBS) for 1 hr at 37° C. The stromal vascular fractions (SVFs) were obtained after removal of mature adipocytes by centrifugation (450 g for 10 min) and the lysis of erythrocytes with ammonium chloride solution. The SVFs were incubated with a FITC-conjugated anti-mouse CD45 antibody, followed by anti-FITC magnetic microbeads (Miltenyi Biotec), and passed through magnetic columns (Miltenyi Biotec).

The mCD45− cell fraction was then incubated with a PE-conjugated anti-mPDGFR-β or anti-mCD31 antibodies, followed by anti-PE magnetic microbeads, and passed through magnetic columns. The purified mCD45-/mPDGFR-β+ murine MSCs (mMSCs) were cultured on uncoated tissue culture dishes using MSC-medium. The purified mCD45-/mCD31+ECs (mECs) were cultured on fibronectin-coated tissue culture dishes using ECFC-medium. mECs were then transduced with lentivirus (pLenti-CMV-GFP; Addgene) to express GFP under CMV promoter (referred to as GFP-mECs). All experiments were carried out with mMSCs at passage 3 and GFP-mECs at passage 12.

Syngeneic Murine Model of Graft Vascularization

C57BL/6-derived mMSCs and GFP-mECs were implanted in collagen-fibrin gel ($2\times10^6$ total; 3:2 ratio; 200 µL) subcutaneously into host C57BL/6 males as U-Grafts in a syngeneic murine model. To evaluate host myeloid cell recruitment, grafts were explanted two days after implantation and subjected to flow cytometric analyses. To assess vascularization, grafts were explanted 7 days after implantation and were subjected to histological analysis. Immunofluorescent staining of GFP indicated the grafting of donor GFP-mECs.

Histology and Immunohistochemistry

Explanted grafts were fixed overnight in 10% buffered formalin, embedded in paraffin and sectioned (7-µm-thick). Hematoxylin and eosin (H&E)-stained sections were examined for the presence of erythrocyte-filled blood vessels. For immunostaining, sections were deparaffinized and antigen retrieval was carried out with tris-EDTA buffer (10 mM Tris-Base, 2 mM EDTA, 0.05% Tween-20, pH 9.0) or citric buffer (10 mM sodium citrate, 0.05% Tween 20, pH 6.0). Sections were then blocked for 30 min in 5-10% blocking serum and incubated with primary antibodies overnight at 4° C. Horseradish peroxidase-conjugated mouse secondary antibody (1:200; Vector Laboratories) and 3,3'-diaminobenzidine (DAB) were used for detection of hCD31, followed by hematoxylin counterstaining and Permount mounting. Fluorescent staining was performed using fluorescently-conjugated secondary antibodies (1:200) followed by DAPI counterstaining (Vector Laboratories). Primary and secondary antibodies are detailed in Table 1.

TABLE 1

Antibodies used herein

| Antibody | Vendor | Clone | Dilution * |
| --- | --- | --- | --- |
| Biotinylated goat anti-UEA1 | Vector Laboratories | BA-0064 | 1:200 (IHF) |
| Texas Red Streptavidin | Vector Laboratories |  | 1:200 (IHF) |
| Unconjugated rat anti-mouse Ly-6G | Bio X Cell | 1A8 | 200 and 100 µg/mouse (D) 1:50 (IHF) |
| Unconjugated rat anti-mouse F4/80 | Bio X Cell | CI:A3-1 | 400 and 200 µg/mouse (D) 1:50 (IHF) |
| PE-Cy5-conjugated rat anti-mouse CD45 | BD Pharmingen | 30-F11 | 1:100 (FC) |
| PE-conjugated rat anti-mouse F4/80 | AbD Serotec | CI:A3-1 | 1:10 (FC) |
| FITC-conjugated rat anti-mouse Ly6G | eBioscience | 1A8 | 1:100 (FC) |
| FITC-conjugated rat anti-mouse CD45 | BD Pharmingen | 30-F11 | 1:100 (MACS) |
| PE-conjugated rat anti-mouse CD31 | BioLegend | MEC13.3 | 1:10 (MACS) |
| PE-conjugated rat anti-mouse PDGFR-β | BioLegend | APB5 | 1:10 (MACS) |
| PE-conjugated rat anti-mouse CD19 | eBioscience | 1D3 | 1:100 (FC) |
| FITC-conjugated rat anti-mouse CD3e | eBioscience | 145-2C11 | 1:100 (FC) |
| Mouse anti-human CD31 | DakoCytomation | JC70A | 1:50 (IHC) |
| Mouse anti-human Vimentin | Abcam | V9 | 1:200 (IHF) |
| Rabbit anti-αSMA | Abcam | Ab5694 | 1:200 (IHF) |
| Rabbit anti-mouse F4/80 | Acris | BM8 | 1:100 (IHF) |
| Rabbit anti-collagen IV | Abcam | Ab6586 | 1:100 (IHF) |
| Goat anti-Fluorescein | Vector Laboratories | SP-0601 | 1:100 (IHF) |
| Rabbit anti-GFP | Abcam | Ab6556 | 1:2000 (IHF) |
| Peroxidase-conjugated horse anti-mouse IgG | Vector Laboratories | PI-2000 | 1:200 (IHC) |
| FITC-conjugated horse anti-mouse IgG | Vector Laboratories | FI-2000 | 1:200 (IHF) |
| DyLight 550-conjugated Donkey anti-rat IgG | Thermo Fisher | SA5-10027 | 1:200 (IHF) |
| FITC-conjugated goat anti-rabbit IgG | Vector Laboratories | FI-5000 | 1:200 (IHF) |
| Texas Red-conjugated goat anti-rabbit IgG | Vector Laboratories | TI-5000 | 1:200 (IHF) |
| Alexa Fluor 488-conjugated donkey anti-goat IgG | Thermo Fisher | A-11055 | 1:200 (IHF) |
| Guinea pig polyclonal anti-insulin | Abcam | Ab7842 | 1:200 (IHF) |

MACS: Magnetic-activated cell sorting;
FC: flow cytometry;
IF: immunofluorescence cell staining;
IHC: immunohistochemistry staining;
IHF: immuno-histofluorescence staining;
D: depletion Microvessel Density Microvessel density was reported as the average number of erythrocyte-filled vessels (vessels/mm$^2$) in H&E-stained sections from the middle of the implants as previously described (Melero-Martin, et al. Circ. Res. 103:194-202 (2008)). The entire area of each section was analyzed. On specified experiments, human-specific microvessel density was quantified by evaluation of slides immunostained for human-specific CD31 (h-CD31). Perfused microvessel density was measured by injection of FITC-labeled lectins (UEA-1 or Iso-B4) before euthanizing graft-bearing mice, followed by staining of lectin-labeled vessels with anti-UEA-1 or anti-FITC antibodies.

Cell Retrieval and Flow Cytometry

Grafts were removed from euthanized mice and cells were retrieved by enzymatic (1 mg/mL collagenase and 2.5 U/mL dispase) digestion for 1 h at 37° C. Retrieved cells were then prepared into single-cell suspensions. In indicated experiments, retrieved cells were sorted into hCD31+ and hCD31− cells by magnetic-activated cell sorting (MACS) using magnetic beads (DynaBead) coated with anti-human CD31 antibodies. Retrieved cells were also stained for flow cytometry and analyzed using a Guava easyCyte 6HT/2L flow cytometer (Millipore Corporation, Billerica, Mass.) and FlowJo software (Tree Star Inc., Ashland, Oreg.). Antibody labeling was carried out for 20 min on ice followed by 3 washes with PBS supplemented with 1% BSA and 0.2 mM EDTA. Cell staining was followed by fixation with 1% paraformaldehyde. To identify murine myeloid population, cell suspensions were incubated with PerCP-conjugated anti-mouse CD45, PE-conjugated anti-mouse F4/80 and FITC-conjugated anti-mouse Ly6G with concentrations indicated in Table 1. Murine neutrophils were identified as mCD45+/mLy6G+ cells. Murine monocytes and macrophages were identified as mCD45+/mLy6G−/mF4/80$^{dim}$ cells and mCD45+/mLy6G−/mF4/80$^{high}$ cells, respectively. In indicated experiments, retrieved cells were sorted into mCD45+/mLy6G+ (neutrophils) and mCD45+/mLy6G− cells by fluorescence-activated cell sorting (FACS) using a FACSAria II 5-LASER sorter system (BD Bioscience). Sorted cells were analyzed immediately for gene expression by qPCR.

Myeloid Cell Depletion

Figure 2A:
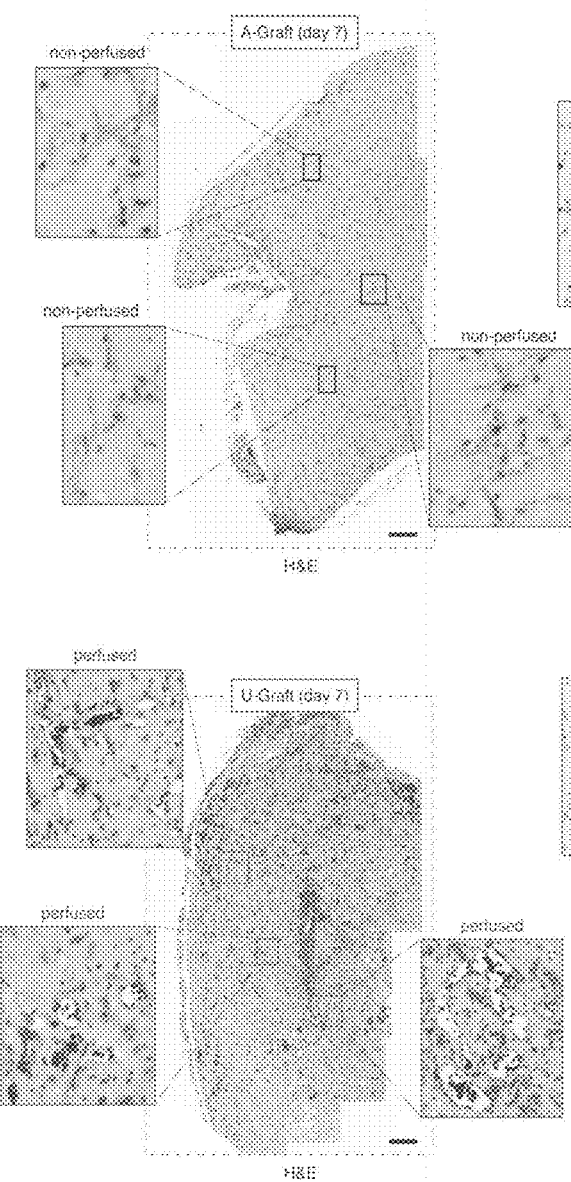
FIGS. 2A-B. Histological analysis of explanted bioengineered grafts. A. H&E staining of A-Grafts and U-Grafts explanted after 7 days in vivo. Perfused vessels were identified as luminal structures containing RBC. B. Immunohistochemical staining of hCD31+ cells at day 7. Human hCD31+ vascular structures were identified as either perfused (lumens containing RBC) or non-perfused (cord structures). Scale bars: 500 μm.

Antibodies and inhibitors were administered intraperitoneally according to the schedule described in FIG. 2A. Rat anti-mouse Ly-6G (clone 1A8; Bio X Cell) antibodies were administered at 200 µg/mouse 2 days before U-grafts implantation, then every other day at 100 µg/mouse. CXCR2 inhibitor SB225002 (Sigma) was administered at 7.5 mg/kg. Rat anti-mouse F4/80 (clone CI:A3-1; Bio X Cell) antibodies were administered at 400 µg/mouse 2 days before U-grafts implantation, then every day at 200 µg/mouse. Daily injection of rat IgG (200 µg/mouse) served as control. Circulating monocyte and neutrophil depletion was confirmed in blood samples by flow cytometry.

Myeloid Adoptive Transfer Model

Circulating myeloid cells were depleted from recipient mice by two 4Gy gamma irradiation sessions at days −4 and 0. Neutrophils or mF4/80+ cells (~10$^7$ cells) from non-irradiated donor mice were adoptively transferred by injection at the implantation sites in recipient mice and at the same time of U-Graft implantation (day 0). Donor neutrophils were isolated from either bone marrow or blood using a murine neutrophil isolation kit (Miltenyi Biotec). Donor mF4/80+ cells were isolated from bone marrow by magnetic-activated cell sorting (MACS) using magnetic beads (Miltenyi Biotec) coated with anti-mF4/80 antibodies.

Generation of Conditioned Media

Samples of conditioned media (CMs) were collected daily from U-Grafts over 8 days in vitro (i.e., until they became A-Grafts). To this end, grafts were cultured in 3-mL tubes with 500 µL of EBM-2, 5% FBS media refreshed every 24 h. Collected CM samples were filtered (0.2 µm) and then concentrated 10-fold (Amicon Ultra centrifugal filters; 3 kDa cut off; Millipore). In indicated experiments, A-Grafts were impregnated with CM from U-Grafts. To this end, A-Grafts were placed on clean kimwipes (2×2 cm$^2$) and then concentrated CM (50 µL) from U-Grafts was added on top of the grafts slowly to allow a replacement of culture medium by capillary force. Impregnated A-Grafts were immediately implanted into recipient mice. A-Grafts impregnated in basal media (basal-M: EBM-2, 5% FBS) served as control.

Neutrophil Recruitment Plug Assay

Concentrated CM (50 µL) was mixed with 200-µL of Matrigel and injected subcutaneously into nu/nu mice. After 2 days, plugs were explanted and infiltrated cells were retrieved by enzymatic digestion and subjected to flow cytometric analysis. Concentrated basal media (basal-M: EBM-2, 5% FBS) served as control. In indicated experiments, neutralizing antibodies against IL6, CXCL1 or CXCL8 (5 µg/antibody/plug) were added to concentrated CM 30 min prior to implantation. Individual neutralizing antibodies and the combination of three were compared.

CXCR2 Antagonist Treatment

CXCR2 antagonist SB225002 (Sigma) was administered at 7.5 mg/kg intraperitoneally 30 mins before U-grafts implantation, and then every day until day 7. Neutrophil recruitment at day 2 and graft vascularization at day 7 were measured as described before. Daily injection of saline served as control. In selected experiments, SB225002 treatment was combined with rat anti-mouse Ly-6G treatment (clone 1A8; administered as described above) to study the combined effect on U-Graft vascularization.

TGF-β Receptor Inhibitor Treatment

U-Grafts were implanted in mice systemically treated with a TGF-β receptor inhibitor (SB432542; 10 mg/kg of animal weight; daily intraperitoneal injection). Mice receiving saline injections served as controls. Grafts were harvested at day 7 to evaluate vascularization.

LPS Plug Assay

Lipopolysaccharides (LPS; 10 µg; from E. coli 0111:B4; Sigma) were mixed with 200-µL Matrigel and was injected subcutaneously into nu/nu mice. After 1 day, plugs were explanted, infiltrated cells were retrieved, and neutrophils were sorted by FACS for analysis.

Phagocytosis Assay

Cells were retrieved from U-Grafts or LPS plugs 24 h after implantation and were then incubated with GFP-expressing E. coli. for 30 min. Cells were washed twice in PBS and free bacteria were removed by centrifugation (300 rpm). Cells were analyzed by flow cytometry and immunofluorescence. Murine neutrophils were identified as mCD45+/mLy6G+ cells and phagocyted E. coli as GFP+ bacteria.

Zymography

Freshly explanted U-Grafts were plated into single wells of a six-well plate in serum-free EBM-2. Cultures were incubated overnight. The next day, the protein concentration of the supernatants was determined, and equal amounts of total protein were subjected to 10% gelatin zymography (Fernandez, et al. J. Biol. Chem 278: 40989-40995 (2003)). After electrophoresis, gels were stained with coomassie brilliant blue for 30 min and then destained for 1 h.

MMP-Sense Live Imaging

Explanted U-Grafts (day 2) were immediately mounted in OCT embedding compound and froze at −80° C. without fixation. Cryosections (100 μm) were carried out by a cryostat at −20° C. After briefly washing in water, sections were incubated with MMP-sense 645 FAST probe (PerkinElmer) at 37° C. for 1 h, according to the manufacturer's instructions. Neutrophils were stained with anti-Ly6G antibodies and nuclei counterstained with DAPI. Images were analyzed with an ApoTome.2 Optical sectioning system (Carl Zeiss).

Human Cytokine Protein Array

The presence of selected cytokines was evaluated in samples of CM with human cytokine protein arrays (R&D Systems Inc.) according to the manufacturer's instructions. Antigen-antibody complexes were visualized using Lumi-GLO substrate (Kirkegaard & Perry Laboratories, Inc.) and chemiluminescent sensitive film (Kodak). Densitometry was performed by image analysis (ImageJ) to estimate the amount of protein present in each sample.

Quantitative RT-PCR

Quantitative RT-PCR (qRT-PCR) was carried out in RNA lysates prepared from either or explanted grafts, cells in culture, or cells retrieved from grafts. Total RNA was isolated with a RNeasy kit (QIAGEN) and cDNA was prepared using reverse transcriptase III (Invitrogen), according to the manufacturer's instructions. Multigene transcriptional profiling, a form of qRT-PCR, was used to determine the number of mRNA copies per cell normalized to ribosomal 18S rRNA abundance, as previously described (Lin, et al. Blood 118: 5420-5428 (2011)). Real-time PCR primer sequences are displayed in Table 2. Heat maps were generated using Gene-E software package from the Broad Institute (www.broadinstitute.org/cancer/software/GENE-E/).

TABLE 2

PCR primers used herein

| Species | Gene | Forward | SEQ ID NO: |
|---|---|---|---|
| mouse | CCL2 | GCTTCTGGGCCTGCTGTTC | SEQ ID NO: 1 |
| mouse | CCL5 | GACACCACTCCCTGCTGCTT | SEQ ID NO: 2 |
| mouse | Tnf | GCCGATGGGTTGTACCTTGT | SEQ ID NO: 3 |
| mouse | Itgam | CCGGGATCAGCTTGAAAGG | SEQ ID NO: 4 |
| mouse | Csf1 | CGCTGCCCTTCTTCGACAT | SEQ ID NO: 5 |
| mouse | Icam1 | GGCACCCAGCAGAAGTTGTT | SEQ ID NO: 6 |
| mouse | Fas | GCGATTCTCCTGGCTGTGA | SEQ ID NO: 7 |
| mouse | IL1rn | CCAGCTGGAGGAAGTTAACATCA | SEQ ID NO: 8 |
| mouse | Arg1 | CCACAGTCTGGCAGTTGGAA | SEQ ID NO: 9 |
| mouse | F4/80 | GTCATCTCCCTGGTATGTCTTGC | SEQ ID NO: 10 |
| mouse | IL4 | GAGTCCAAGTCCACATCACTGAA | SEQ ID NO: 11 |
| mouse | Vegf-A | GGAAAGACCGATTAACCATGTCA | SEQ ID NO: 12 |
| mouse | Pmepa1 | GCTGAGCCACTACAAGCTGTCA | SEQ ID NO: 13 |
| mouse | Tgfbi | CGGTGTGGTCTATGCCATCA | SEQ ID NO: 14 |
| mouse | Mmp1a | AACAACCCATTTGATGGACCTAAC | SEQ ID NO: 15 |
| mouse | Mmp2 | TGGGAGCATGGAGATGGATAC | SEQ ID NO: 16 |
| mouse | Mmp3 | GGTCTTCCGGTCCTGCTGT | SEQ ID NO: 17 |
| mouse | Mmp4 | TCCCAGACAGGCCCTGTTC | SEQ ID NO: 18 |
| mouse | Mmp7 | ATTGGCTTCGCAAGGAGAGA | SEQ ID NO: 19 |
| mouse | Mmp8 | GTGAAAACAGCAATTGAGAAAGCTT | SEQ ID NO: 20 |
| mouse | Mmp9 | CAGACGTGGGTCGATTCCA | SEQ ID NO: 21 |
| mouse | Mmp10 | TTCCAGGAATTGAGCCACAAG | SEQ ID NO: 22 |
| mouse | Mmp11 | GGACGCTGGGAGAAGACAGA | SEQ ID NO: 23 |
| mouse | Mmp12 | GCCACACTATCCCAGGAGCATA | SEQ ID NO: 24 |
| mouse | Mmp13 | GATGCCATTACCAGTCTCCGA | SEQ ID NO: 25 |
| mouse | Mmp14 | GCCTTCCGAGTATGGGAGAGT | SEQ ID NO: 26 |
| mouse | Mmp15 | TACACTGAGAAGCTGGGCTGGTA | SEQ ID NO: 27 |

TABLE 2-continued

PCR primers used herein

| Species | Gene | | SEQ ID NO: |
|---|---|---|---|
| mouse | Mmp16 | GCAGTATTTCAATGTGGAGGTTTG | SEQ ID NO: 28 |
| mouse | Mmp17 | GCTCCATCATGCAACCGTACT | SEQ ID NO: 29 |
| mouse | Mmp19 | AACTGACCTTAGCCGCTACCCTA | SEQ ID NO: 30 |
| mouse | Mmp23 | TGAACGTCCCAGTGACCTCA | SEQ ID NO: 31 |
| mouse | Mmp24 | GGATCCCAGTCACTGGTGTGT | SEQ ID NO: 32 |
| mouse | Mmp25 | CCTAGATGGCCGAATCATCCT | SEQ ID NO: 33 |
| mouse | Mmp27 | GATGGTCCTCTGGGAGTCCTT | SEQ ID NO: 34 |
| mouse | Mmp28 | AGCCTCTGGGACGCTCAGT | SEQ ID NO: 35 |
| human | NOTCH1 | CGGGTCCACCAGTTTGAATG | SEQ ID NO: 36 |
| human | HEY1 | GCTGCCTCTGCTCTCCTCAGT | SEQ ID NO: 37 |
| human | HEY2 | ATGAGCATAGGATTCCGAGAGTG | SEQ ID NO: 38 |
| human | HES1 | TCAGCGAGTGCATGAACGA | SEQ ID NO: 39 |
| human | HES5 | ACCAGCCCAACTCCAAGCT | SEQ ID NO: 40 |
| human | CXCL1 | CTGCCCTTACAGGAACAGAAGAG | SEQ ID NO: 41 |
| human | IL6 | GGCAGAAAACAACCTGAACCTT | SEQ ID NO: 42 |
| human | CD31 | CACCTGGCCCAGGAGTTTC | SEQ ID NO: 43 |
| human | CD90 | GCCTAACGGCCTGCCTAGT | SEQ ID NO: 44 |
| h/m | 18S rRNA | TGTCTCAAAGATTAAGCCATGCA | SEQ ID NO: 45 |
| Species | Gene | Reverse | SEQ ID NO: |
| mouse | CCL2 | GTGAATGAGTAGCAGCAGGTGAGT | SEQ ID NO: 46 |
| mouse | CCL5 | TGCTGCTGGTGTAGAAATACTCCTT | SEQ ID NO: 47 |
| mouse | Tnf | GTGGGTGAGGAGCACGTAGTC | SEQ ID NO: 48 |
| mouse | Itgam | TGGAAGGTCACACTGAATTCTCTTA | SEQ ID NO: 49 |
| mouse | Csf1 | TTCTGACACCTCCTTGGCAAT | SEQ ID NO: 50 |
| mouse | Icam1 | GCCTCCCAGCTCCAGGTATAT | SEQ ID NO: 51 |
| mouse | Fas | CACGGCTCAAGGGTTCCAT | SEQ ID NO: 52 |
| mouse | IL1rn | CTGGACAGGCAGCTGACTCA | SEQ ID NO: 53 |
| mouse | Arg1 | GCATCCACCCAAATGACACA | SEQ ID NO: 54 |
| mouse | F4/80 | GTGCATGTAGGTATTGTGGTTCTGA | SEQ ID NO: 55 |
| mouse | IL4 | TGGCTCAGTACTACGAGTAATC | SEQ ID NO: 56 |
| mouse | Vegf-A | GGCTTTCTGGATTAAGGACTGTTC | SEQ ID NO: 57 |
| mouse | Pmepa1 | TTCCGAGGACAGTCCATCGT | SEQ ID NO: 58 |
| mouse | Tgfbi | CCAGCTCATCTCCTCGTTCTTG | SEQ ID NO: 59 |
| mouse | Mmp1a | TGTTGGTCCACGTCTCATCAAG | SEQ ID NO: 60 |
| mouse | Mmp2 | AAGTGAGAATCTCCCCCAACAC | SEQ ID NO: 61 |
| mouse | Mmp3 | ATCATCATCCCTTGCACTGTCA | SEQ ID NO: 62 |
| mouse | Mmp4 | GCCTCGAAGTTACTGCCGTCTA | SEQ ID NO: 63 |
| mouse | Mmp7 | GCGAAGGCATGACCTAGAGTGT | SEQ ID NO: 64 |
| mouse | Mmp8 | TGTTGATGTCTGCTTCTCCCTGTA | SEQ ID NO: 65 |

TABLE 2-continued

PCR primers used herein

| | | | |
|---|---|---|---|
| mouse | Mmp9 | TCGCGGCAAGTCTTCAGAGT | SEQ ID NO: 66 |
| mouse | Mmp10 | GAACTGTGATGATCCTCGGAAGA | SEQ ID NO: 67 |
| mouse | Mmp11 | GCCGGACTTGCTCCCTTAC | SEQ ID NO: 68 |
| mouse | Mmp12 | GTGGGTCAAAGACAGCTGCAT | SEQ ID NO: 69 |
| mouse | Mmp13 | GAGCTCAGCCTCAACCTGCT | SEQ ID NO: 70 |
| mouse | Mmp14 | TCATGTCCCTCCCGGATGT | SEQ ID NO: 71 |
| mouse | Mmp15 | GTGTGACCTGCTCCCACACTT | SEQ ID NO: 72 |
| mouse | Mmp16 | AGCGCAGCACTGACATTCTG | SEQ ID NO: 73 |
| mouse | Mmp17 | ACGCACCCTGTCCTCATAGG | SEQ ID NO: 74 |
| mouse | Mmp19 | GAGGGTCGGTCTGGCACTC | SEQ ID NO: 75 |
| mouse | Mmp23 | GTGGTGCACTGCAGAGACCA | SEQ ID NO: 76 |
| mouse | Mmp24 | TGATCAGGGACGCCACATC | SEQ ID NO: 77 |
| mouse | Mmp25 | CAAGCTGTCGTTCCTGGAACA | SEQ ID NO: 78 |
| mouse | Mmp27 | GGCTATCCATGTTTCATCTTCGT | SEQ ID NO: 79 |
| human | Mmp28 | CGTCTGCTCTGGGAGTTGTG | SEQ ID NO: 80 |
| human | NOTCH1 | CCGCAGAGGGTTGTATTGGTT | SEQ ID NO: 81 |
| human | HEY1 | GCATTGGGAGACAGTAAGTGGAA | SEQ ID NO: 82 |
| human | HEY2 | GAGGAGTCCAGGCCTTCCA | SEQ ID NO: 83 |
| human | HES1 | TTGATCTGGGTCATGCAGTTG | SEQ ID NO: 84 |
| human | HES5 | GGCTTTGCTGTGCTTCAGGTA | SEQ ID NO: 85 |
| human | CXCL1 | TCTCCTAAGTGATGCTCAAACACAT | SEQ ID NO: 86 |
| human | IL6 | GGCAAGTCTCCTCATTGAATCC | SEQ ID NO: 87 |
| human | CD31 | AGTACACAGCCTTGTTGCCATGT | SEQ ID NO: 88 |
| h/m | CD90 | GGGTGAACTGCTGGTATTCTCAT | SEQ ID NO: 89 |
| mouse | 18S rRNA | GCGACCAAAGGAACCATAACTG | SEQ ID NO: 90 |

Microscopy

Images were taken using an Axio Observer Z1 inverted microscope (Carl Zeiss) and AxioVision Rel. 4.8 software. Fluorescent images were taken with an ApoTome.2 Optical sectioning system (Carl Zeiss) and 20×/0.8 or 40×/1.4 oil objective lens. Non-fluorescent images were taken with an AxioCam MRc5 camera using a 40×/1.4 objective oil lens.

Statistical Analyses

Unless otherwise stated, data were expressed as mean±standard deviation of the mean (s.d.). For comparisons between two groups, means were compared using unpaired two-tailed Student's t-tests. Comparisons between multiple groups were performed by ANOVA followed by Bonferroni's post-test analysis. Samples size, including number of mice per group, was chosen to ensure adequate power and were based on historical data. No exclusion criteria were applied for all analyses. No specific methods of randomization were applied to group/animal allocation. Investigators were not blinded to group allocation. All statistical analyses were performed using GraphPad Prism v.5 software (GraphPad Software Inc.). P<0.05 was considered statistically significant.

Example 1. Inefficient Engraftment of Bioengineered Human Microvessels

Figure 1B:
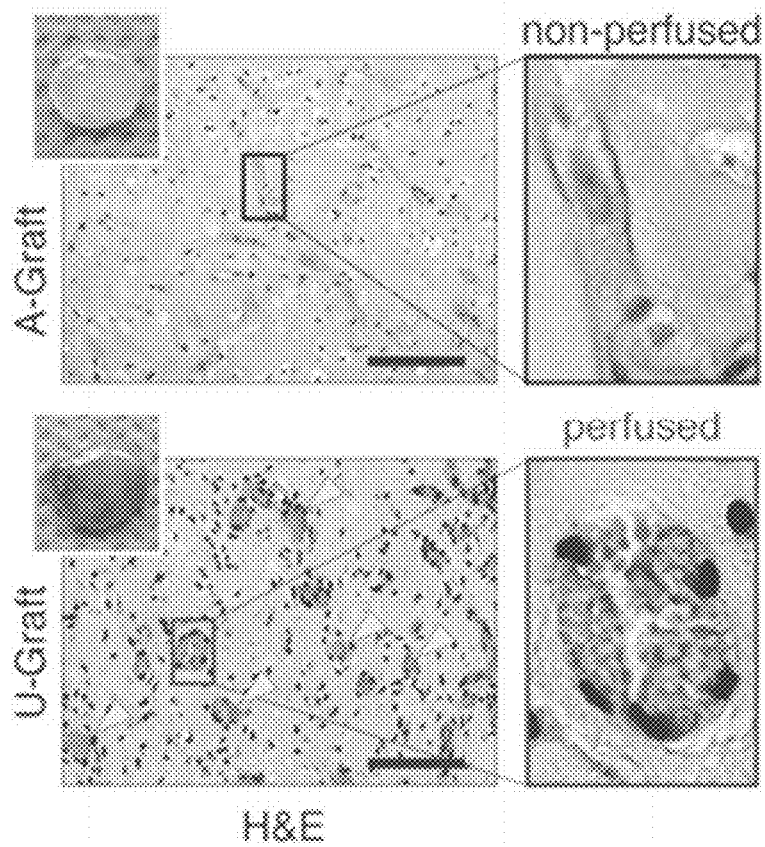
Figure 1C:
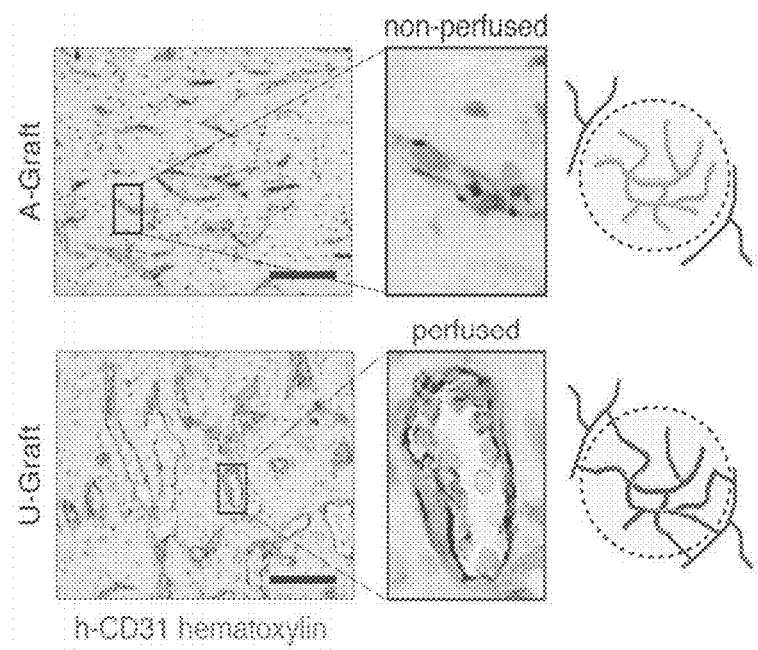
Figure 1D:
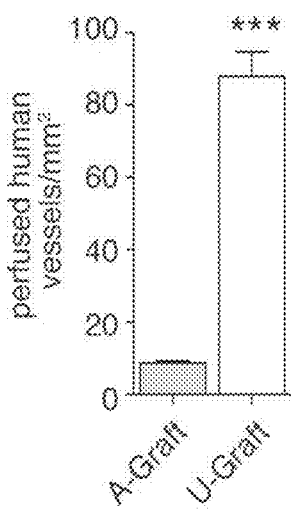
Figure 2B:
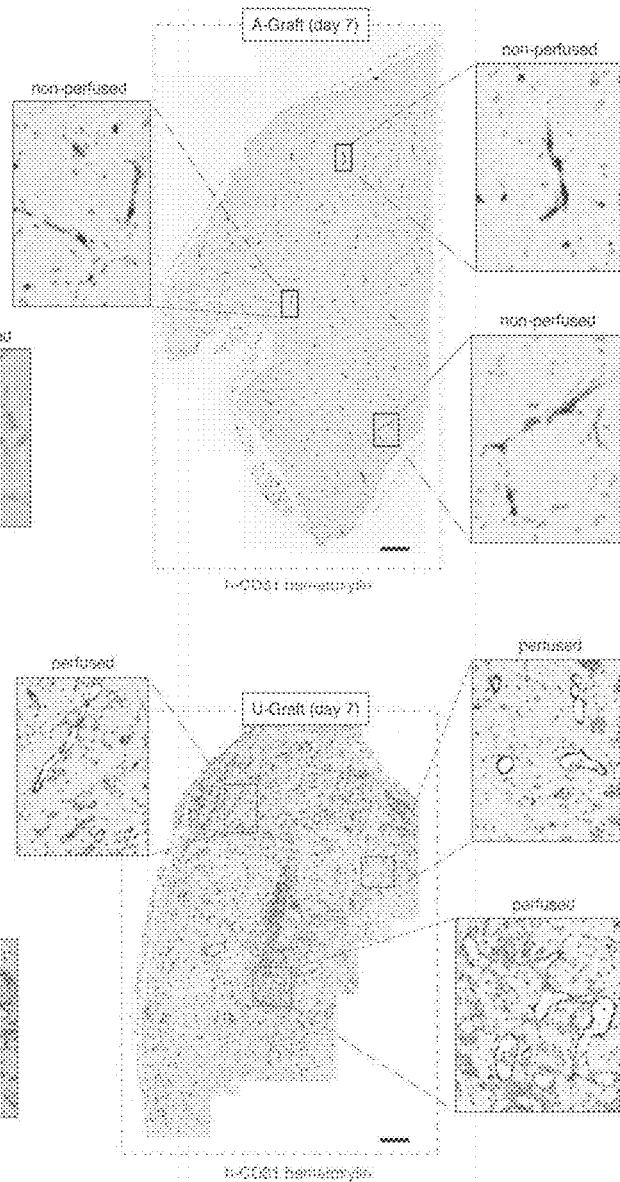
Figure 3A:
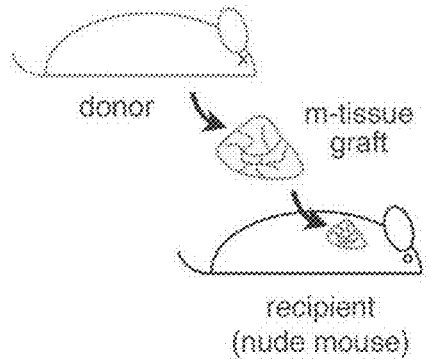
FIGS. 3A-D. Engraftment of primary murine tissues. A. Schematic depicting Rosa26fsTrap;Cdh5(Pac)-CreERT2+ mice as tissue donors and nude mice as recipients. Myocardium (B), kidney (C), and liver (D) were harvested from donor mice and implanted into recipient mice as 3×3×3 mm3 grafts. At day 7, mice were infused with FITC-conjugated Griffonia Simplicifolia Lectin I (GSL I) isolectin B4 (Iso-β4) and grafts were then explanted. Perfused vessels were identified as Iso-B4+ vessels (green; anti-FITC antibody). Donor vessels were identified as GFP+ vessels (red; anti-GFP antibody). primary control tissue were analyzed in Rosa26fsTrap;Cdh5(Pac)-CreERT2+ mice. Bars represent mean±s.d.; n=3. *** $P<0.001$ between primary and engrafted tissues. Scale bars: 50 μm.
Figure 3B:
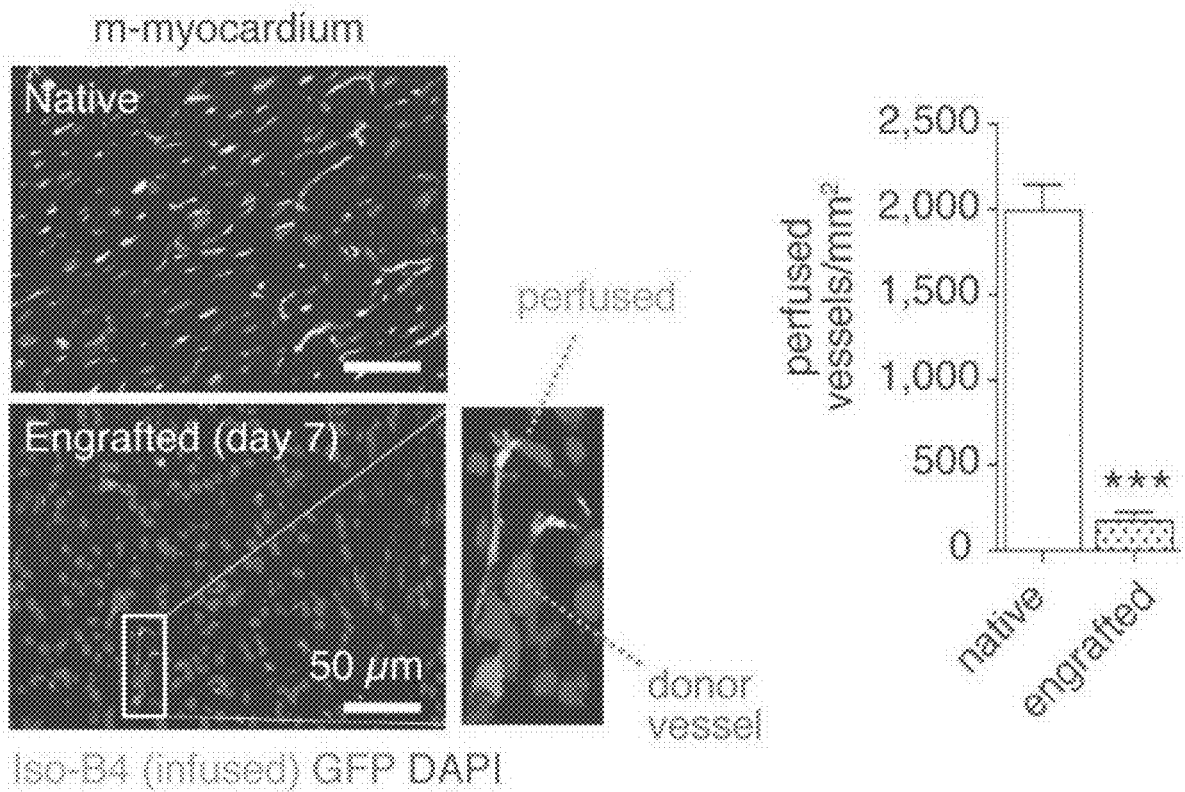
Figure 3C:
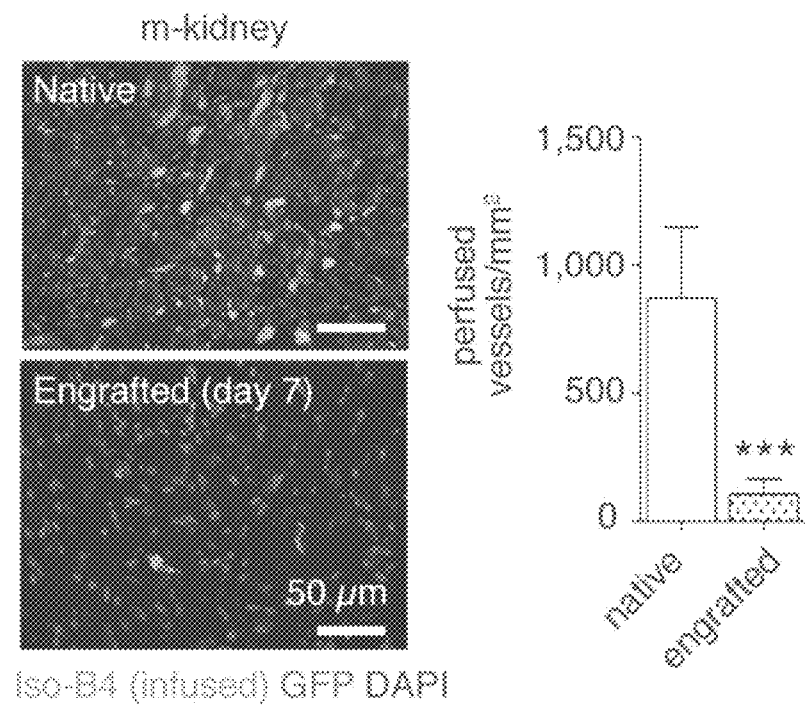
Figure 3D:
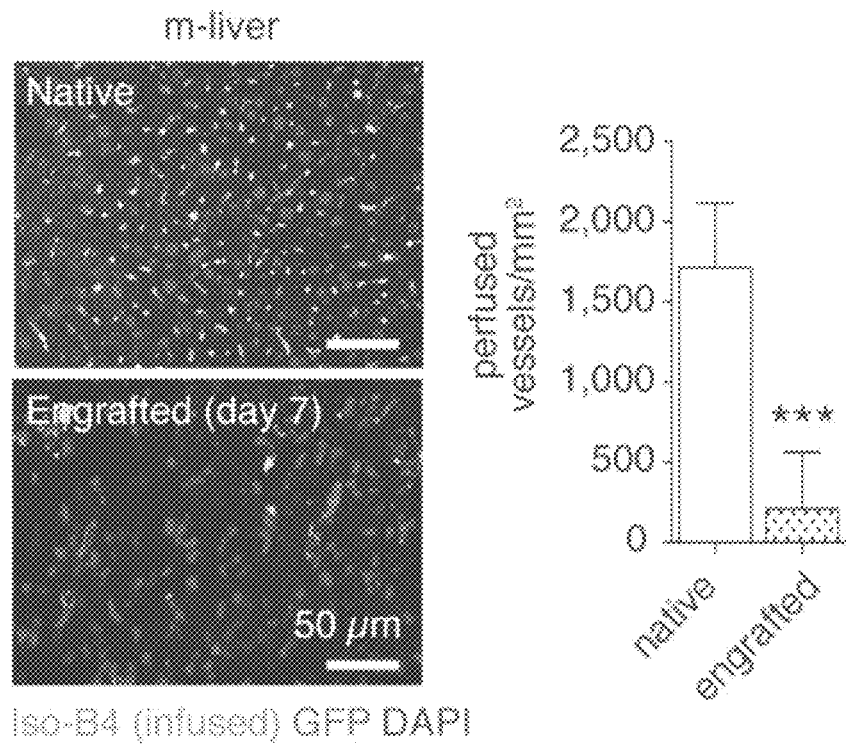
Figure 4A:
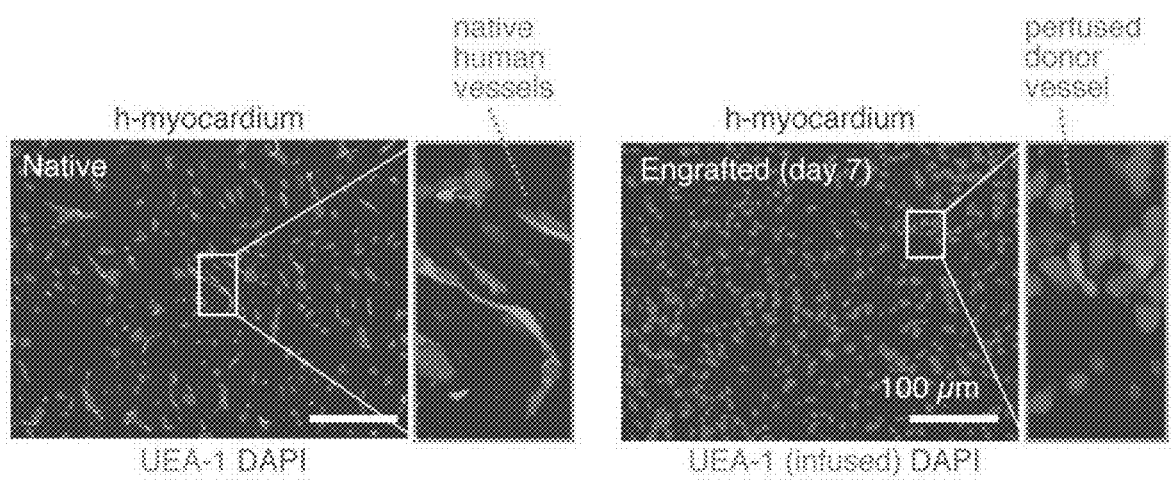
FIGS. 4A-B. Engraftment of primary human myocardial tissue. A. Discarded normal human right ventricular myocardial tissues were trimmed into 3×3×3 mm3 cubes and surgically implanted (subcutaneously) into nude mice. At day 7, mice were infused with FITC-conjugated Ulex Europaeus Agglutinin-I (UEA-I) and grafts were then explanted. Perfused human vessels were identified as UEA-I+vessels (red). Non-implanted primary myocardial tissues served as control. B. Density of perfused human blood vessels. Bars represent mean±s.d.; n=3. *** $P<0.001$ between primary and engrafted tissues. Scale bars: 100 μm.
Figure 4B:
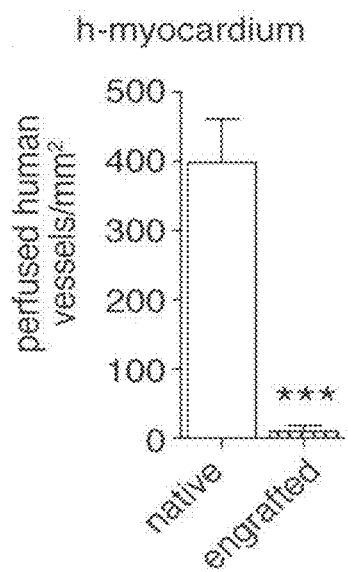
Figure 5A:
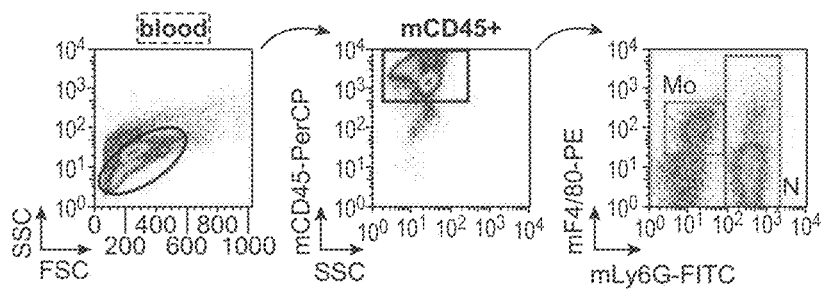
FIGS. 5A-E. Flow cytometry analysis in myeloid cell depleted mice. General scheme for flow cytometry analysis of (A) blood samples and (B) cells retrieved from explanted grafts. For treatments, circulating monocytes were depleted with α-F4/80 antibodies (α-F4/80). Neutrophil were depleted with α-Ly6G antibodies (α-Ly6G). IgG treatment served as control (no myeloid cell depletion). Flow cytometry analysis of blood samples 2 days after treatments, depicting (C) circulating monocytes (Mo) and (D) neutrophils (N). Bars represent mean±s.d.; n=3. * $P<0.001$,  $P<0.01$, * $P<0.05$ compared to IgG group. (E) Flow cytometry analysis of cells retrieved at day 2 from U-Grafts that were implanted in treated mice. N, Mo, and MΦ refer to neutrophils, monocyte, and macrophages, respectively.
Figure 5B:
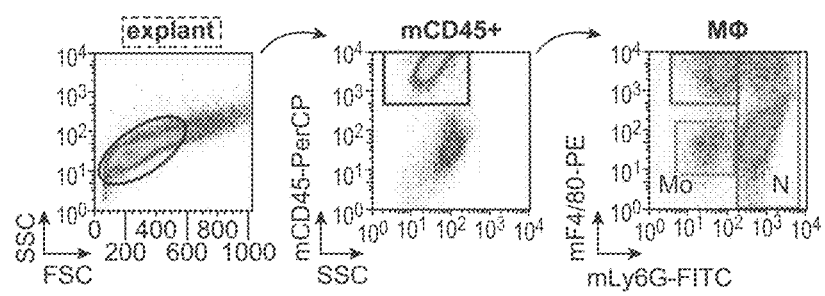
Figure 5C:
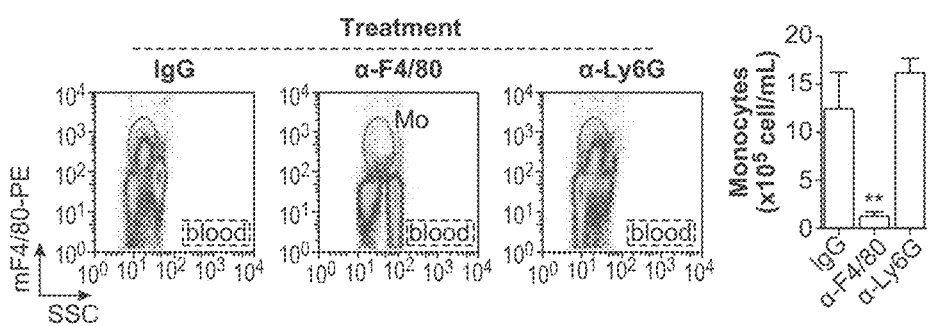
Figure 5D:
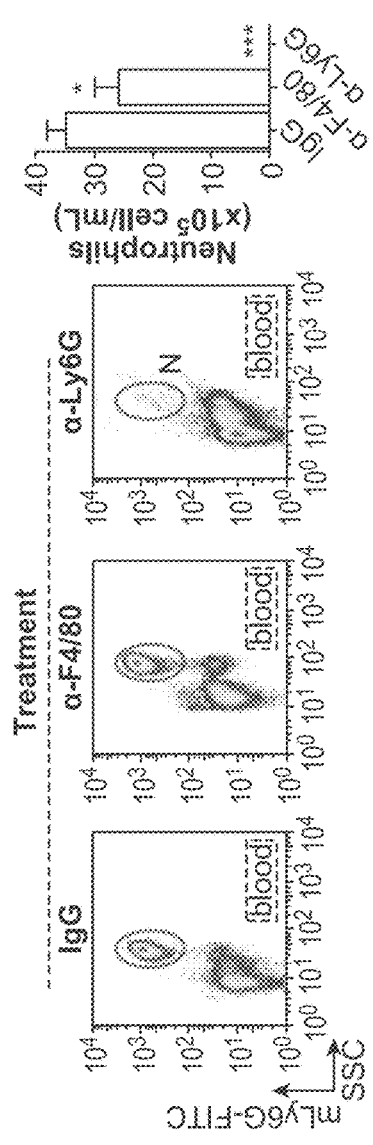
Figure 5E:
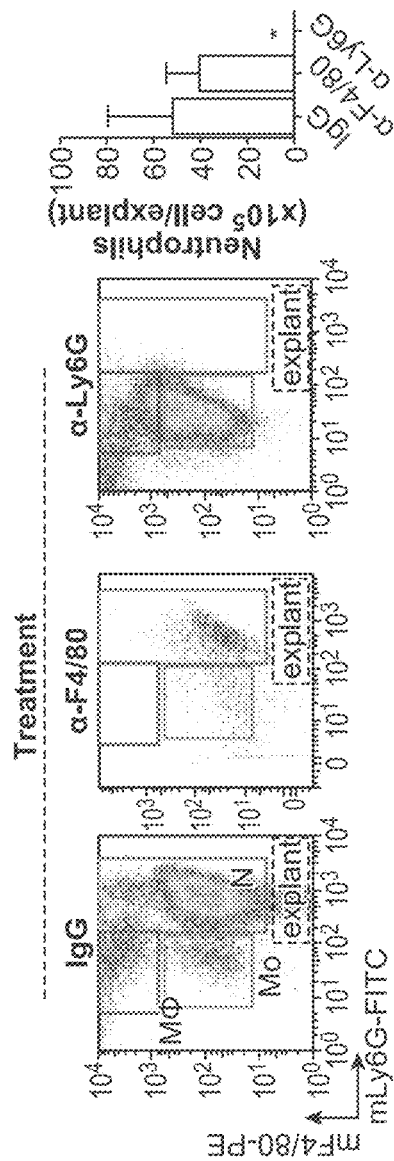

To evaluate engraftment of bioengineered microvessels, we generated grafts containing fully-assembled vascular networks embedded in 3-dimensional constructs (A-grafts). In addition, we prepared grafts that simply contained an unassembled suspension of the same vascular cells (U-Grafts) (FIG. 1A). In both cases, grafts were prepared in vitro by combining human endothelial colony-forming cells (ECFCs) with mesenchymal stem cells (MSCs) (4×10$^5$ cells; 1:1 ratio) in gelatin-based hydrogels (GelMA) that we previously showed to be compatible with vascular morphogenesis [5,18] U-Grafts were suspensions of the cells in the hydrogel at day 0, whereas A-grafts were formed by letting ECFCs to self-assemble into mature networks over 7 days in vitro (FIG. 1A). We studied the engraftment of both types of grafts following subcutaneous implantation into nude mice. After 7 days in vivo, U-Grafts contained an extensive network of perfused microvessels (FIG. 1B). Their lumens expressed h-CD31, confirming the human nature of the endothelium (FIG. 1B), and carried murine erythrocytes, indicating connection with the host circulatory system (FIGS. 1B, C; FIG. 2). In contrast, the number of perfused human vessels in A-Grafts was insignificant (FIG. 1D). Instead, ECFCs remained organized as cellular cords but these cords were rarely perfused (FIGS. 1B, C). This lack of anastomosis formation by pre-assembled vessels in A-Grafts recapitulated the indolent state observed in the microvasculature of transplanted tissues (both murine and human) (FIG. 3,4). Thus, this A-Graft/U-Graft model was deemed suitable to study the mechanisms regulating engraftment of a bioengineered vascular network in the absence of tissue parenchyma.

Example 2. Host Neutrophils are Indispensable for Vascularization

Figure 1E:
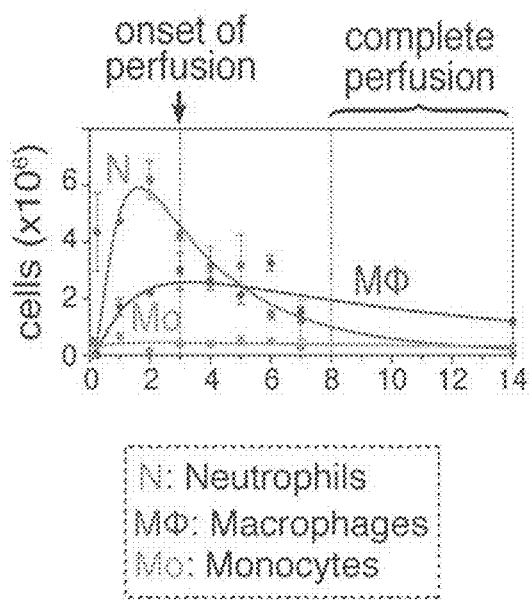
Figure 1F:
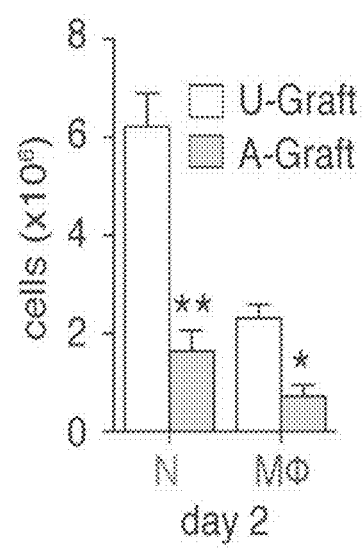
Figure 1G:
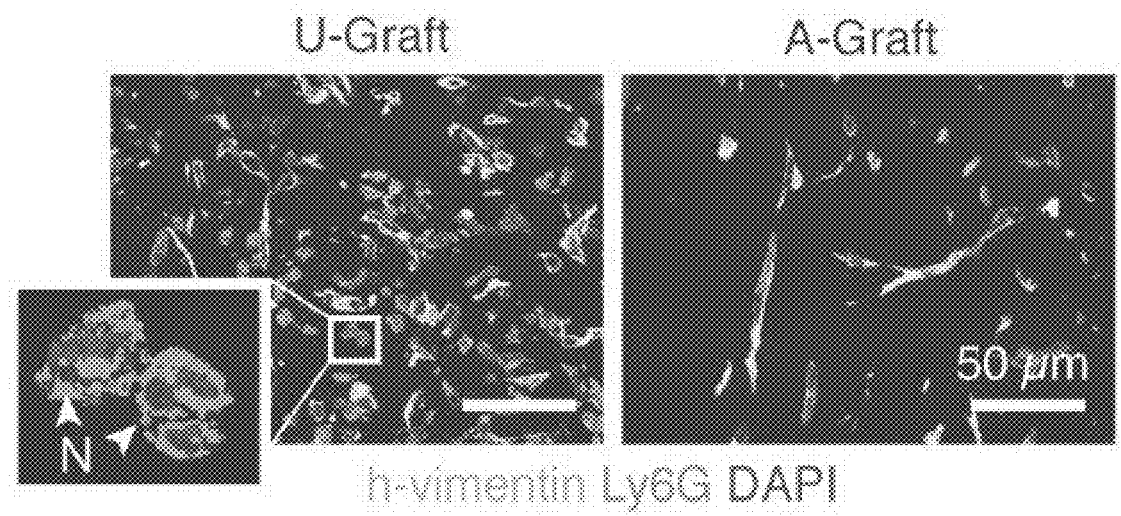
Figure 1H:
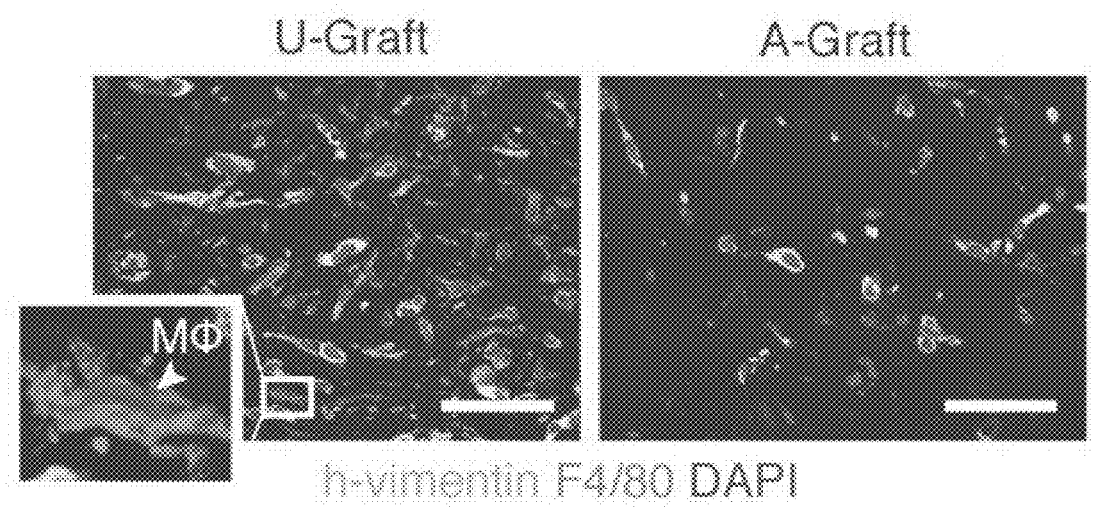

Previously, we recognized that host myeloid cells participate in the vascularization of U-Grafts[19]. In addition, we showed that the hydrogel material used in our grafts is not immunoisolating and that host myeloid cells, including neutrophils, can freely invade our constructs[18]. However, the mechanisms of action and the specific nature of these myeloid subpopulations had yet to be elucidated. Moreover, the role of myeloid cells in the engraftment of A-Grafts was completely unknown. Here, we identified a dynamic presence of three distinct host myeloid subpopulations in U-Grafts: 1) lymphocyte antigen 6 complex, locus G (Ly6G)-/F4/80$^{hi}$ macrophages; 2) Ly6G-/F4/80$^{dim}$ monocytes; and 3) Ly6G+ neutrophils (FIG. 5; FIG. 1E). Neutrophil levels peaked prior to the onset of perfusion (~6×10$^6$ cells/graft at day 2) and then progressively faded as U-Grafts got vascularized, whereas macrophages peaked around day 3 (~3×10$^6$ cells/graft) and then remained moderately constant (FIG. 1E). Of note, there was a spatially uniform lack of both Ly6G+ neutrophils and macrophages throughout A-Grafts, which was in clear contrast to the abundant presence found in U-Grafts (FIGS. 1F-H).

Figure 6A:
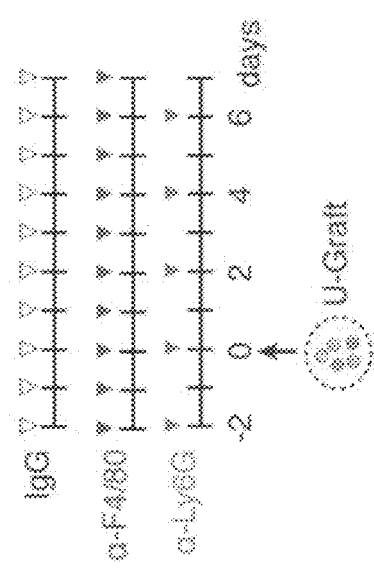
FIGS. 6A-I. Host neutrophils are indispensable for graft vascularization. A. Schematic with myeloid depletion strategies. Circulating monocytes depleted with α-F4/80 antibodies (α-F4/80). Neutrophils depleted with α-Ly6G antibodies (α-Ly6G). U-Graft implanted at day 0. Control (IgG antibodies) and treatments initiated at day −2 and maintained until day 7. B. Flow cytometry analysis of blood samples two days after depletion treatments. Gates for circulating monocytes (Mo) and neutrophils (N) depicted. Bars represent mean±s.d.; n=3-4. *$P<0.001$;  $P<0.01$, *$P<0.05$ compared to IgG group. C. H&E staining of U-Grafts explanted at day 7. Insets are macroscopic views of the explants. Perfused vessels were identified as luminal structures containing RBCs (arrowheads). D. Density of perfused blood vessels at day 7. Bars represent mean±s.d.; n=4 mice per group.  $P<0.01$ compared to IgG group. E. Schematic with neutrophil adoptive transfer strategy. U-Graft implanted into irradiated mice and neutrophils simultaneously transferred from non-irradiated donors. F Macroscopic views of U-Grafts explanted at day 7 from: (i) non-irradiated mice, (ii) irradiated mice, (iii) irradiated mice+transfer of BM-neutrophils, and (iv) irradiate mice+ transfer of BM-F4/80+ cells. (G) H&E and (H) immunohistochemical (h-CD31+ cells) staining of U-Grafts explanted at day 7 from irradiated mice with and without BM-neutrophil transfer. Perfused vessels marked by arrowheads. (I) Microvessel density at day 7. Bars represent mean±s.d.; n=4 mice per group. * $P<0.001$, * $P<0.05$ compared to irradiated group (no transfer). †$P<0.001$ compared to irradiated+BM-neutrophil transfer. § $P<0.05$ compared to irradiated+Blood-neutrophil transfer. Scale bars: 100 μm (C, G, H).
Figure 6B:
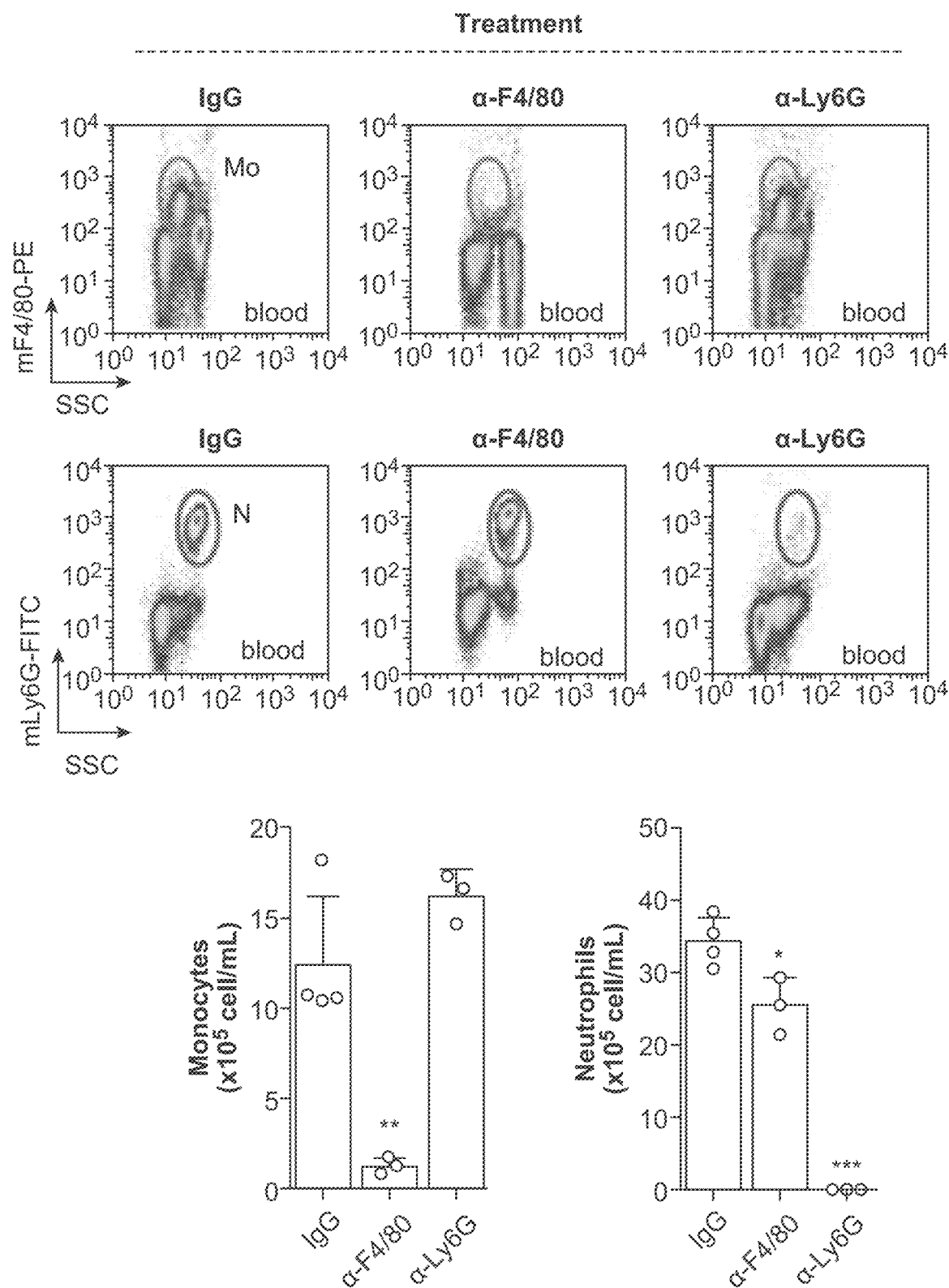
Figure 6C:
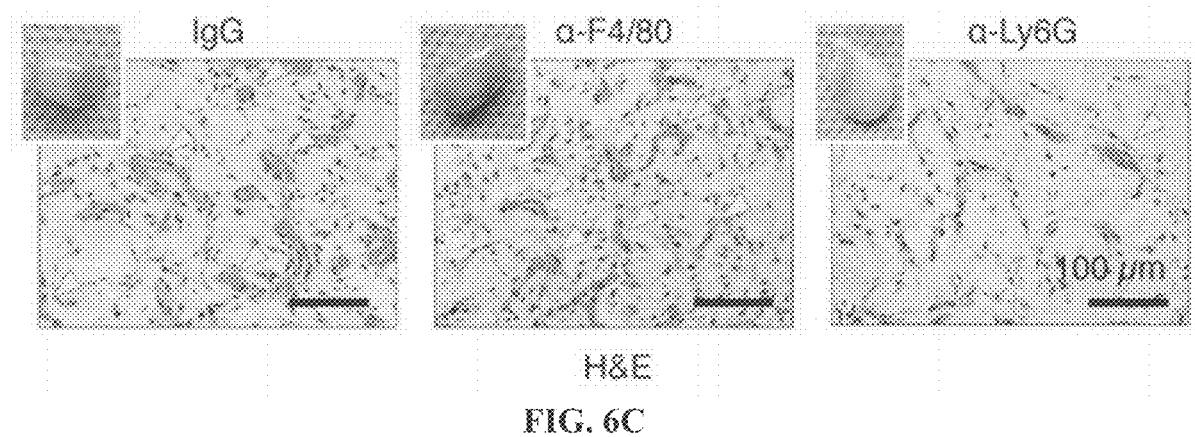
Figure 6D:
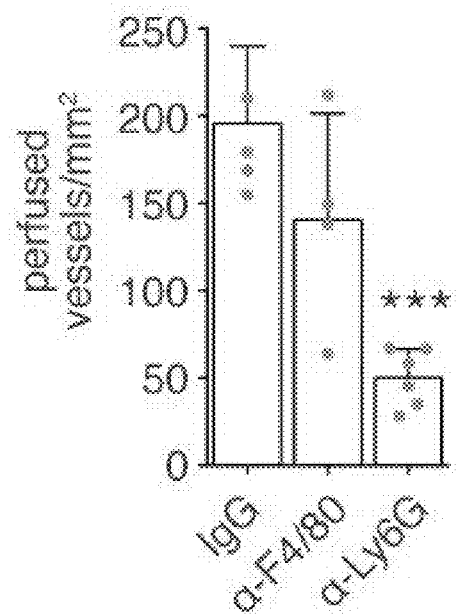

To examine the role myeloid cells in U-Grafts, we devised two separate strategies to deplete either circulating monocytes (α-F4/80 treatment) or neutrophils (α-Ly6G) in recipient mice (FIG. 6A-B; FIG. 5). Depletion of circulating monocytes had no significant effect on vascularization; U-Grafts implanted into α-F4/80-treated mice displayed a microvascular density similar to the control group (140.7±30.3 vessels/mm$^2$ vs. 195.6±19.7 vessels/mm$^2$ in IgG-treated mice) (FIGS. 6C, D). In contrast, depletion of neutrophils was strikingly detrimental on vascularization; U-Grafts implanted into α-Ly6G-treated mice had a reduced presence of perfused vessels at day 7 (FIG. 6C) and microvascular density was significantly lower (50.2±7 vessels/mm$^2$) than in the control group (FIG. 6D).

Figure 6E:
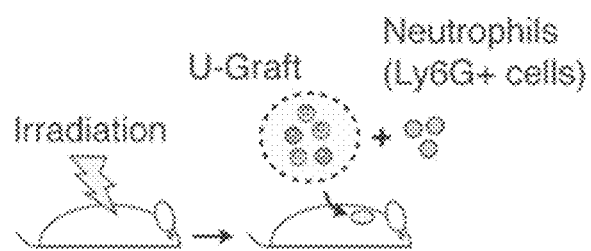
Figure 6F:
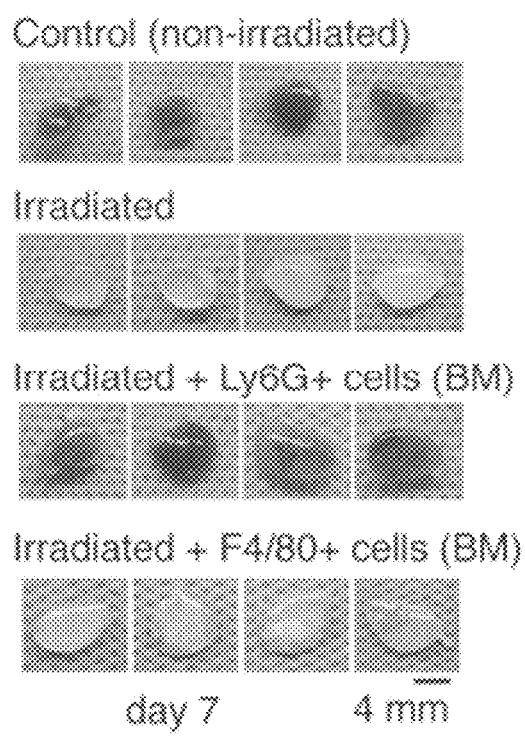
Figure 6G:
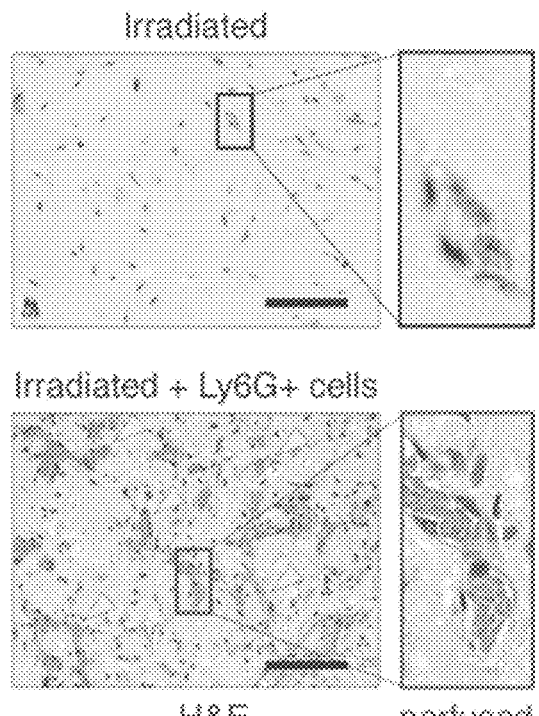
Figure 6H:
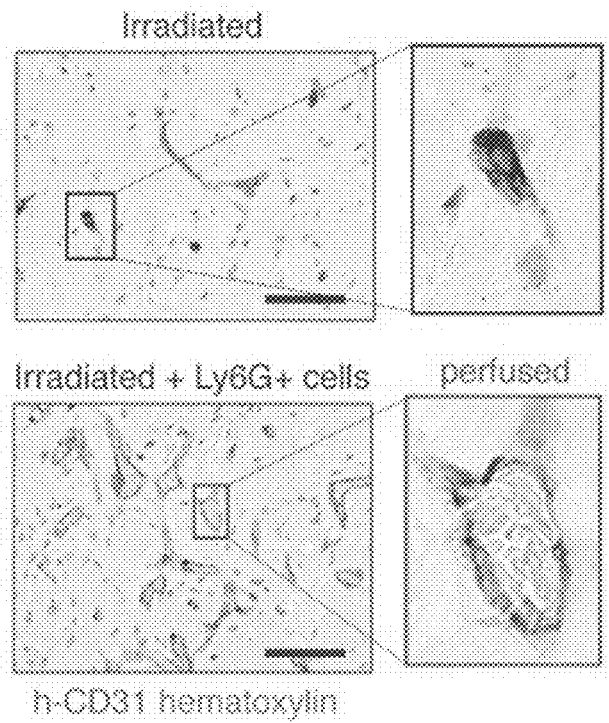
Figure 6I:
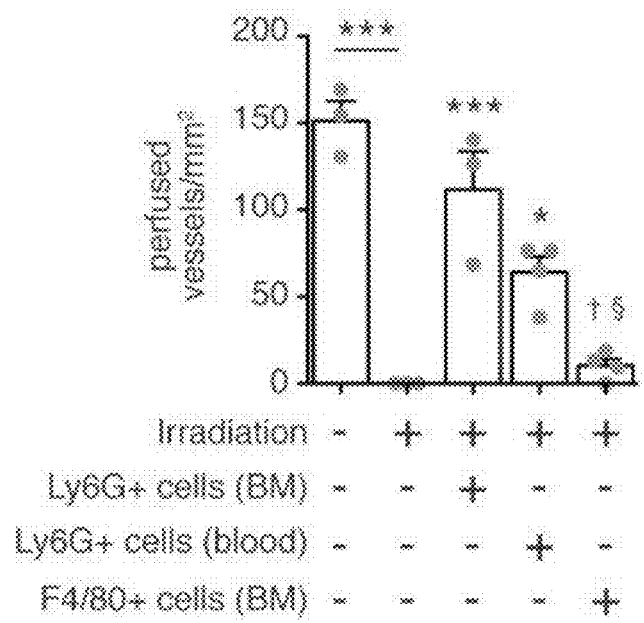
Figure 7A:
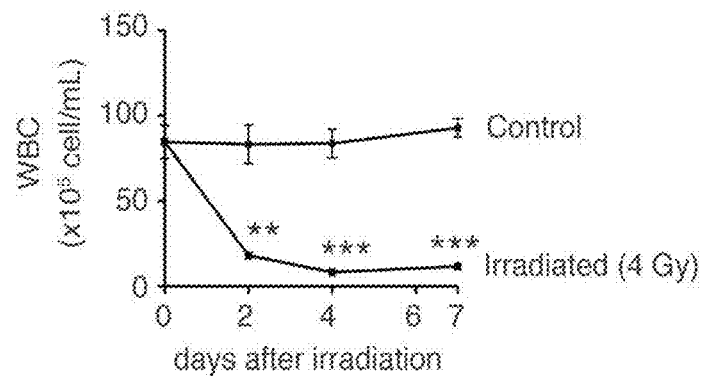
FIGS. 7A-B. Depletion of circulating leukocytes by gamma irradiation. Athymic nu/nu mice were gamma irradiated (4Gy) and blood leukocyte content was monitored by flow cytometry for 7 days. A. Total WBC measured in irradiated and non-irradiated (control) mice. B. Neutrophil count in irradiated and non-irradiated (control) mice. Data represent mean±s.d.; n=4 mice time point. * P<0.001,  P<0.01 compared to control group.
Figure 7B:
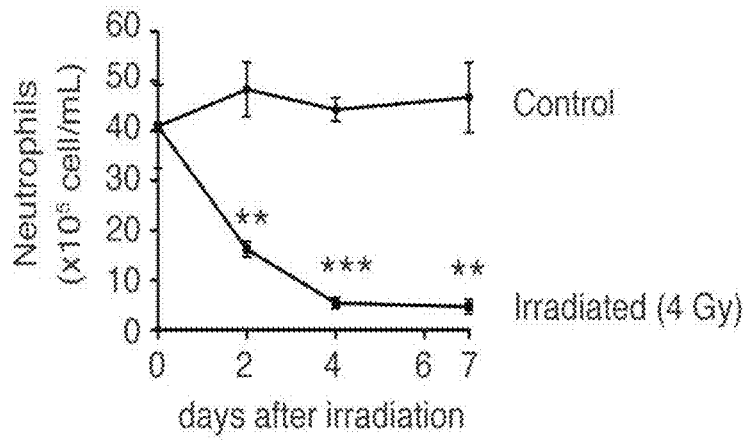
Figure 8:
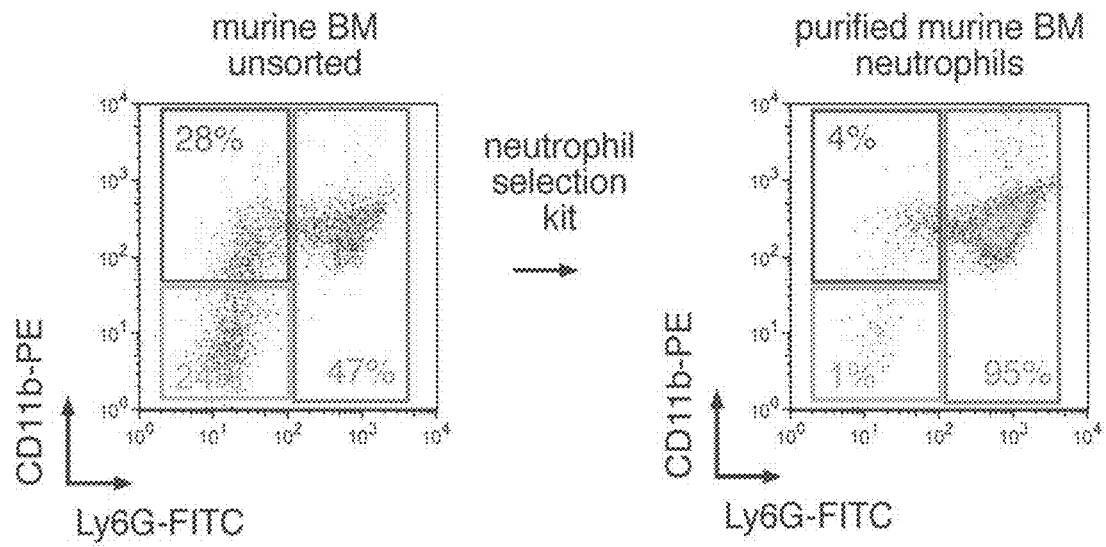
FIG. 8. Isolation and purification of murine bone marrow-derived neutrophils. Bone marrow cells were obtained by flashing the femur of nude mice and analyzed by flow cytometry. Neutrophils were then purified using a murine neutrophil selection kit (Miltenyi Biotec). Flow cytometry panels depict the proportion of neutrophils (CD11b+/Ly6G+ cells) before (~47%) and after (~95%) purification.
Figures 9A, 9B:
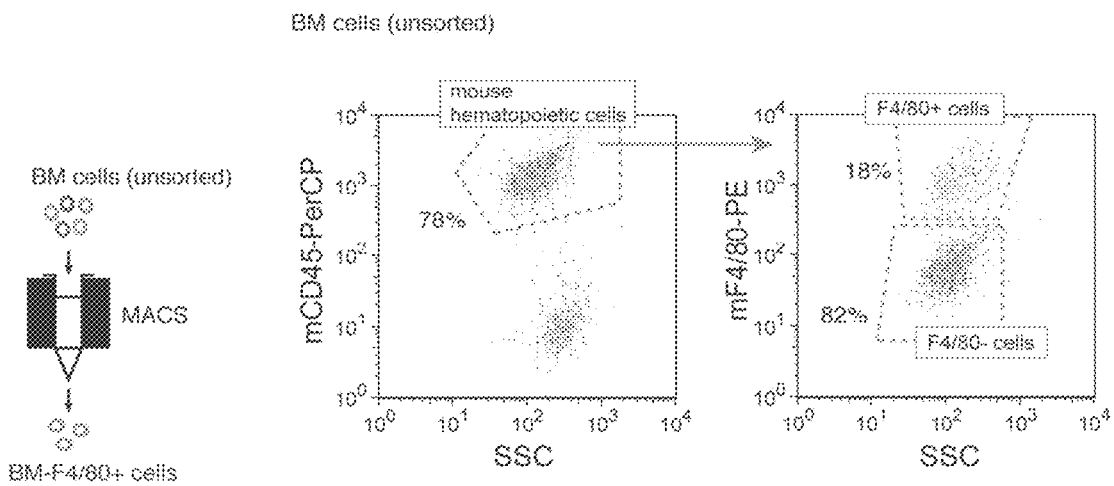
Figure 9C:
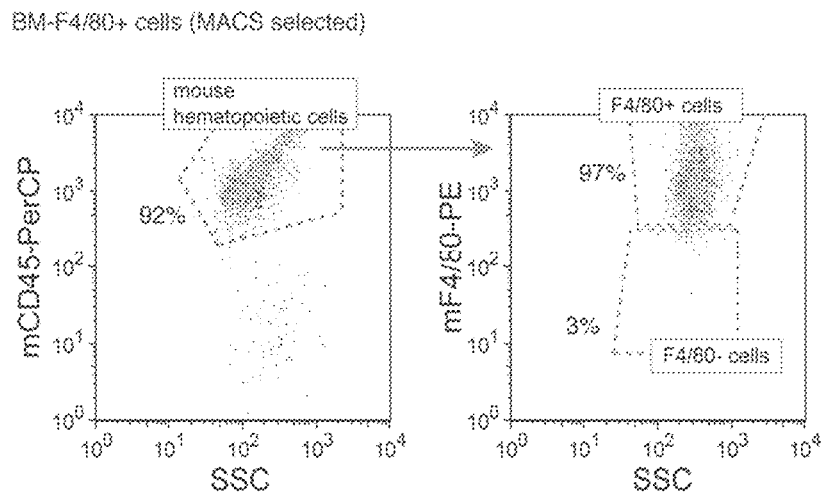
Figure 9D:
Figure 9E:
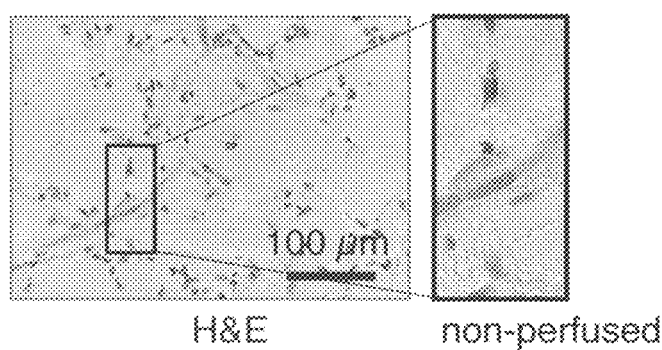

To confirm the pivotal role of neutrophils, we devised an adoptive transfer approach with irradiated mice (radiation effectively depleted >90% circulating myeloid cells for over a week, but it was not lethal; FIG. 7). Briefly, U-Grafts were implanted into irradiated mice with or without a transfer of neutrophils from non-irradiated donor mice (FIG. 6E). Transferred neutrophils were an enriched population of mCD11b$^+$/mLy6G$^+$ cells (~95%; FIG. 8) obtained with a neutrophil selection kit. U-Grafts implanted into irradiated mice completely failed to vascularize; however, an adoptive transfer of bone marrow (BM)-derived mLy6G$^+$ cells fully rescued vascularization, enabling formation of extensive networks of perfused blood vessels (FIGS. 6F-I). Transfer of blood-derived Ly6G$^+$ cells also rescued vascularization, although to a lesser extent (FIG. 6I). Of note, transfer of BM-derived F4/80+ cells (i.e., monocytes/macrophages) failed to rescue vascularization (FIGS. 6F, I; FIG. 9), which underscored the distinctive capability of neutrophils. Collectively, these results confirmed that host mLy6G$^+$ neutrophils are indispensable for vascularization in implanted U-Grafts.

Figure 10D:
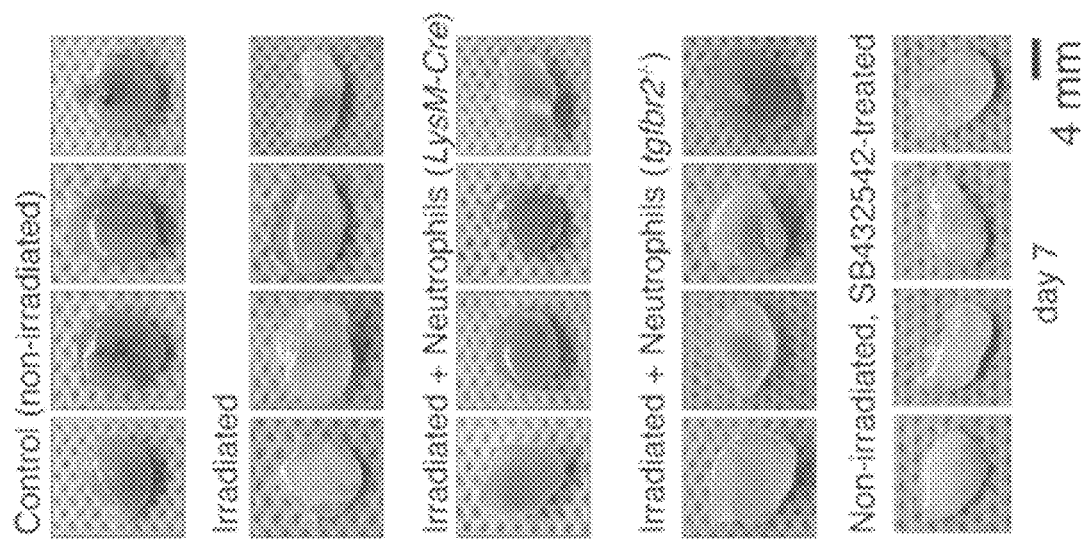
Figure 10C:
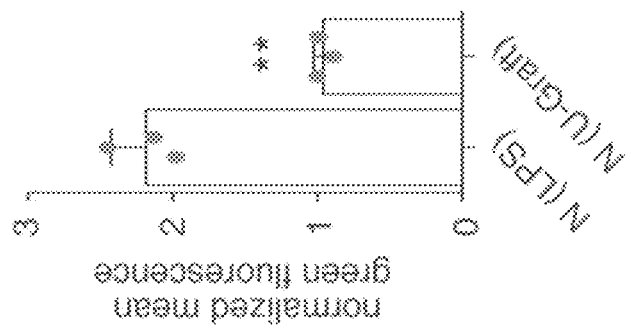
Figure 10C:
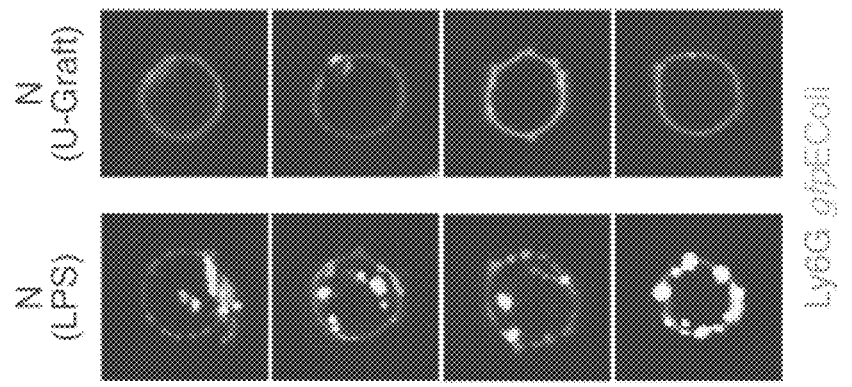
Figure 10E:
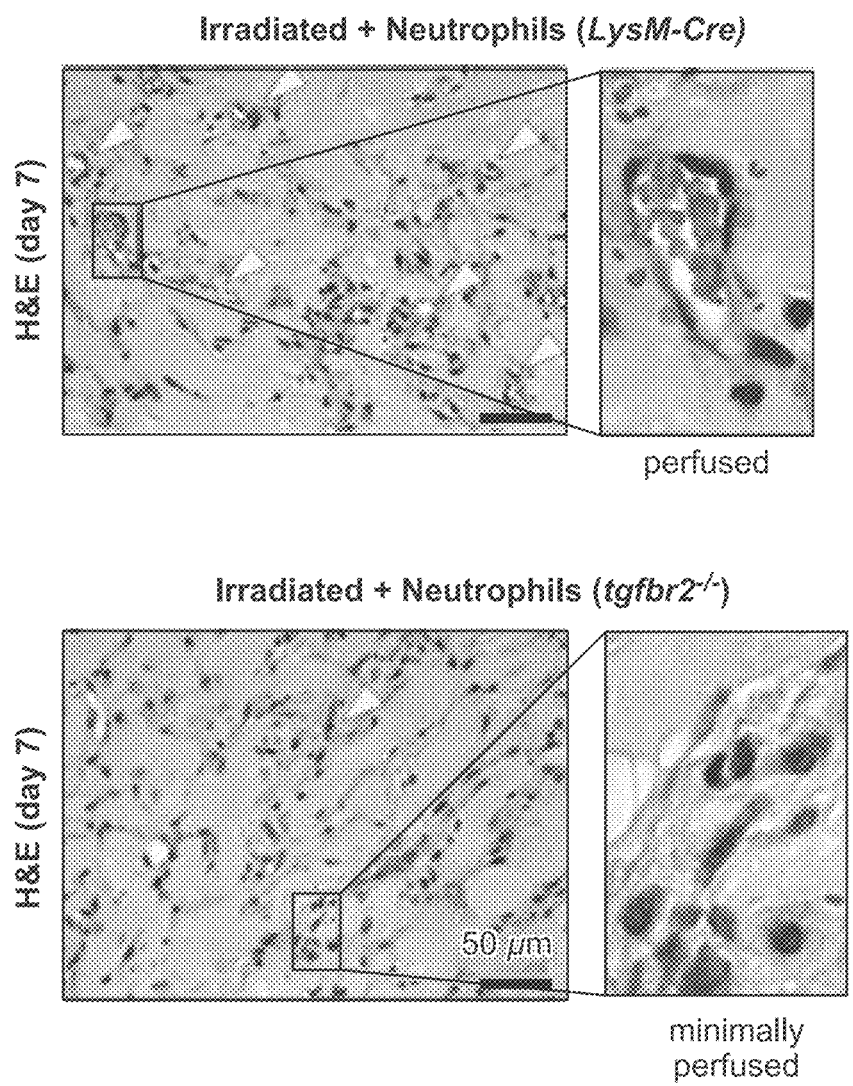
Figure 10F:
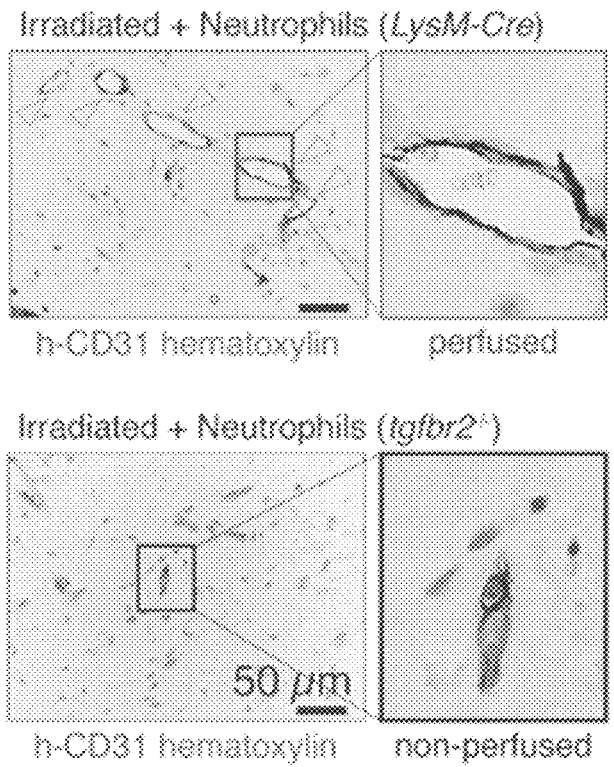
Figure 10G:
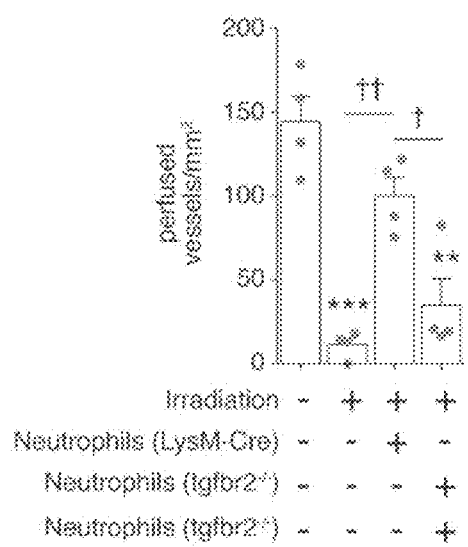
Figure 10H:
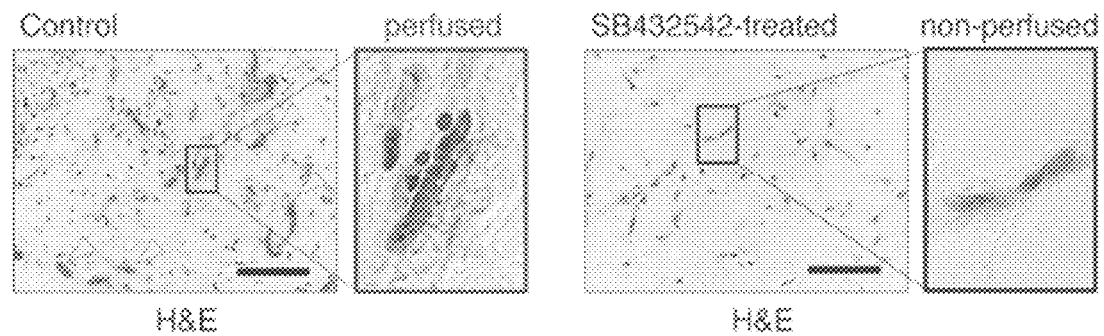
Figure 10I:
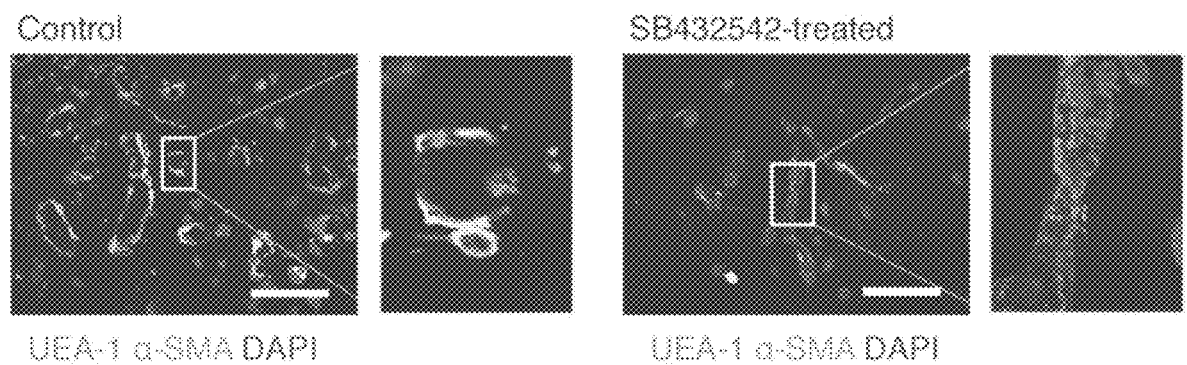
Figure 10J:
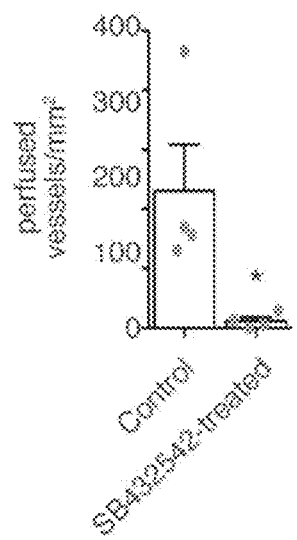
Figure 11D:
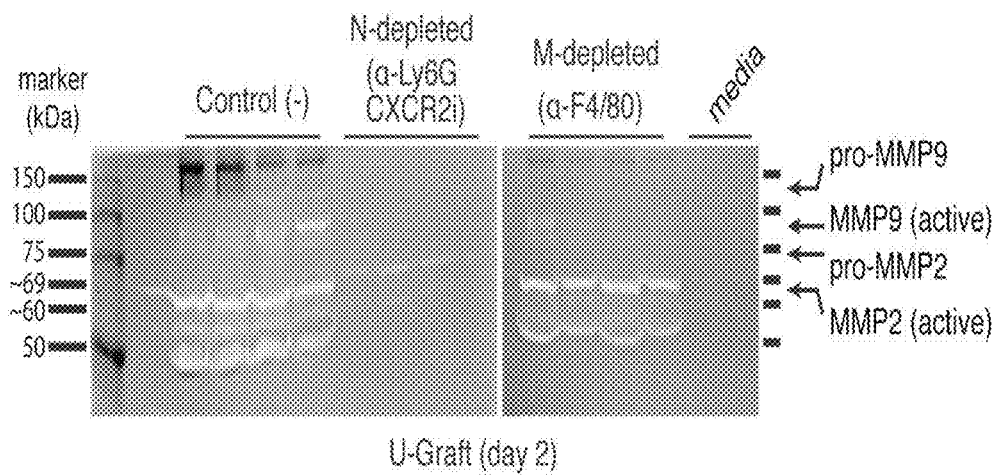
Figure 11E:
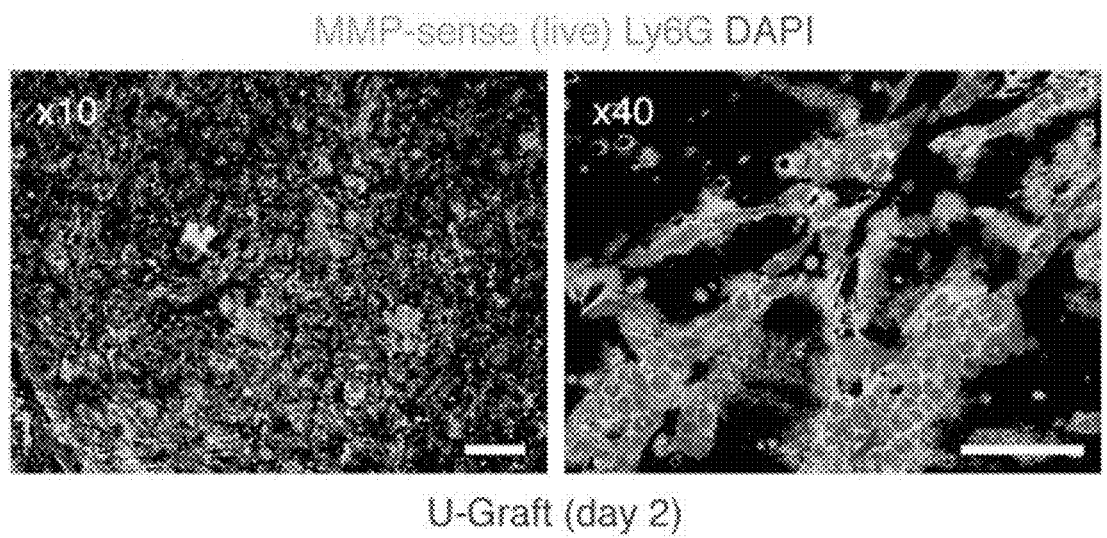
Figure 11F:
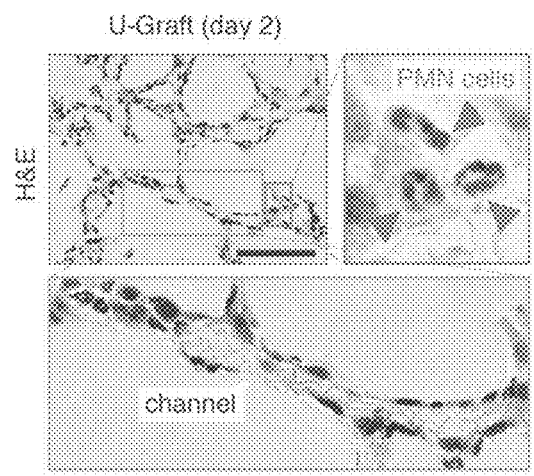

Example 3. Alternatively Polarized Neutrophils Mediate U-Graft Vascularization Recent evidence suggest that neutrophils can acquire an alternative non-inflammatory phenotype (referred to as "N2") that mediates tissue remodeling[20,21]. Here, we compared neutrophils retrieved from explanted U-Grafts to inflammatory neutrophils isolated from lipopolysaccharide (LPS)-containing plugs (FIG. 10A). Neutrophils in U-Grafts did not resemble LPS-activated neutrophils in several respects, including (1) lower mRNA expression of canonical pro-inflammatory genes (namely, Ccl2, Ccl5, F4/80, Tnf Itgam, Csf1, Icam1, Fas, and Il1rn); (2) higher expression of anti-inflammatory (Arg1, Il4) and pro-remodeling (Vegfa, Pmepa1, Tgfbi) genes (FIG. 10B); (3) lower phagocytic activity (FIG. 10C). Previous studies have shown that N2 polarization is mediated via TGFβ signaling[20]. To elucidate the potential role of TGFβ, we adoptively transferred neutrophils lacking TGFβ receptor 2 (tgfbr2$^{-/-}$; from LysM-Cre::tgfbr2/loxP donors) into myeloid-depleted (irradiated) nude mice and examined the ability of U-Grafts to vascularize (FIGS. 11D-F). Tgfbr2$^{-/-}$ neutrophils were not capable of restoring vascularization to the same extent than control neutrophils (34.7±15.9 vessels/mm$^2$ vs. 100.2±11 vessels/mm$^2$ with control LysM-Cre neutrophils) (FIG. 10G), indicating that the pro-vascularization potential of neutrophils was dependent on tgfbr2 expression. To confirm the need for TGF-β signaling, we evaluated the vascularization potential of U-grafts in mice daily treated with SB432542, a potent and selective inhibitor of the TGF-β type I receptor. We found that treatment with SB432542 impaired the formation of perfused vascular networks. Indeed, the number of perfused vessels at day 7 in U-grafts from SB432542-treated mice was insignificant (FIG. 10J); ECFCs appeared organized as cellular cords, but these cords were rarely perfused (FIG. 10H, I). Taken together, our results show that U-Graft's neutrophils distinctively displayed a non-inflammatory phenotype that was consistent with the N2 phenotype; this alternative polarization was dependent on TGFβR/TGFβ signaling, and in turn was essential for neutrophil pro-vascularization function. Moreover, blocking TGF-β signaling via exogenous provision of SB-432542 completely abrogated U-Graft vascularization.

Figure 11G:
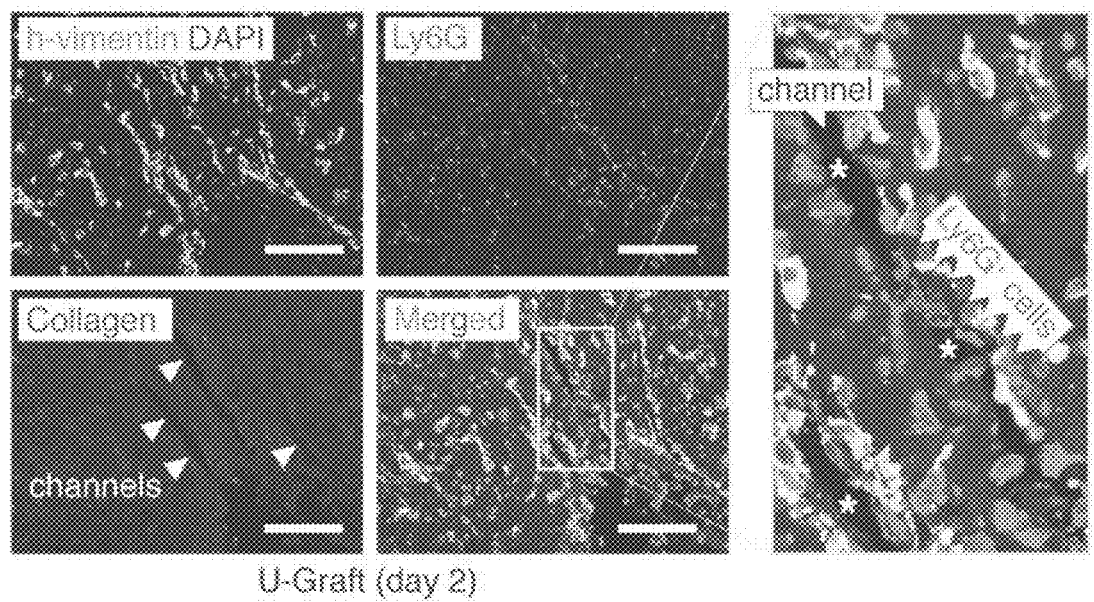
Figure 11H:
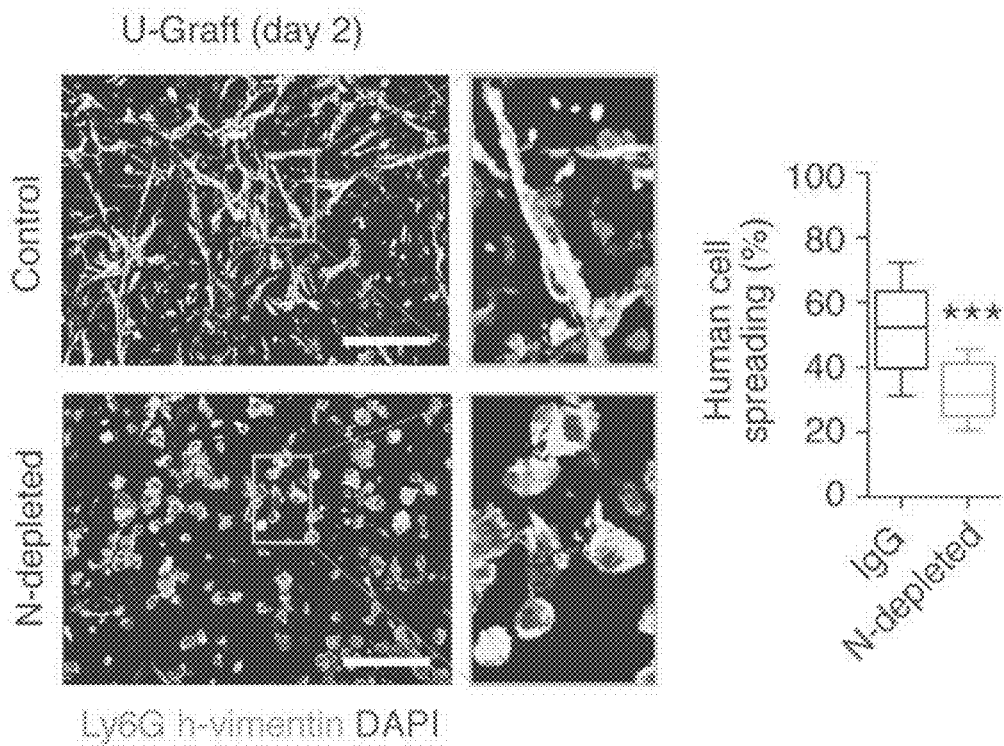
Figure 12A:
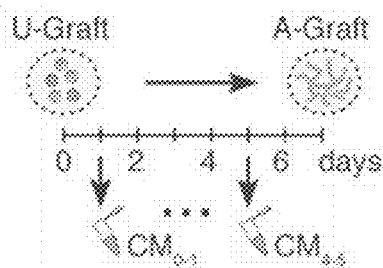
FIGS. 12A-I. Neutrophil activity regulated by secreted factors from the graft vasculature. A. Schematic: daily samples of conditioned media (CM) collected from U-Grafts until they became A-Grafts. B. H&E (left) and immunofluorescent (Ly6G, DAPI) staining revealing infiltration of neutrophils at day 2 into implanted Matrigel plugs containing CM from U-Grafts. Left H&E inset corresponds to plug containing control basal medium (basal-M). C. Flow cytometric quantification of neutrophil infiltration at day 2 into plugs containing CM collected at indicated times. Bars represent mean±s.d.; n=3 plugs per group. ** P<0.01, * P<0.05 compared to $CM_{0-1}$. D. Schematic of A-Grafts impregnated in CM from U-Grafts and implanted into nude mice. E. Flow cytometric quantification of neutrophil infiltration at day 2 into A-Grafts that were impregnated with and without CM(U-Graft). F. H&E staining at day 7 of explanted A-Grafts that were impregnated with either CM(U-Graft) or basal-M. Insets are macroscopic views of the explants. Perfused vessels marked byarrowheads. G. Microvessel density at day 7. Bars represent mean±s.d.; n=4 mice per group.  P<0.01. H. Immunohistochemical staining (h-CD31+ cells) at day 7 in explanted A-Grafts that were impregnated with either CM(U-Graft) or basal-M. Perfused human h-CD31+ vascular structures were identified as lumens containing RBC. I. Density of perfused human microvessels at day 7. Bars represent mean±s.d.; n=4 mice per group. * P<0.001, * P<0.05 between indicated groups. Scale bars: 100 μm (B left, F, II), 50 μm (B right).

Studies have shown that neutrophils exhibit marked metalloproteinase (MMP) activity during angiogenesis and tissue remodeling[22,23]. Thus, we next evaluated expression and activity of MMPs in our grafts. U-Grafts had higher expression of a subset of MMPs (Mmp2, Mmp8, Mmp9, Mmp14, and Mmp19) than other control tissues with known neutrophil presence (i.e., blood, spleen, and BM) (FIGS. 12A, B). Moreover, U-Grafts from neutrophil-depleted mice had a marked reduction in both MMP mRNA expression (qPCR; FIG. 11C) and gelatinase activity (zymography[24]; FIG. 11D). Imaging of explanted U-Grafts using a protease activatable fluorescent MMP-Sense probe confirmed that MMP activity was spatially associated with infiltrated Ly6G+ neutrophils (FIG. 11E). This prominent MMP activity correlated with presence of distinct channels within the hydrogel grafts, which were abundantly populated by polymorphonuclear Ly6G+ neutrophils (FIG. 11F). Moreover, the spatial distribution of these channels coincided with the alignment of h-vimentin+ cells, suggesting utilization by the human cells (FIG. 11G). Also, the presence of neutrophils spatially correlated with well-spread h-vimentin+ cells in U-Graft, whereas human cell spreading in neutrophil-depleted mice was significantly compromised (FIG. 11H). Taken together, graft neutrophils displayed a prominent proteolytic activity that correlated with spatial organization of implanted vascular cells, which reinforces the notion of an alternative non-inflammatory phenotype.

Figure 13A:
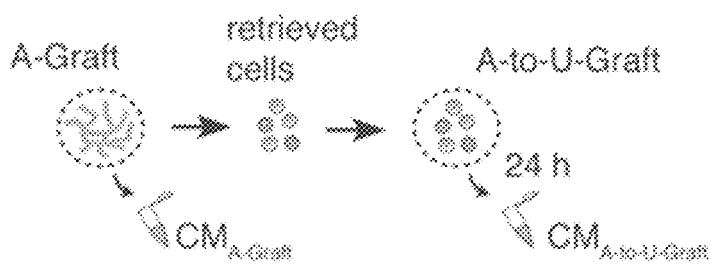
FIGS. 13A-C. Neutrophil recruitment by conditioned media. A. Schematic: cells were enzymatically retrieved from A-Grafts and were then immediately used to construct new U-Grafts (referred to as A-to-U-Grafts). Conditioned media (CM) were collected from both A-Grafts (CMA-Graft) and A-to-U-Grafts (CMA-to-U-Graft). B. Flow cytometric quantification of neutrophil infiltration into plugs containing CM collected from A-Grafts and A-to-U-Grafts. Bars represent mean±s.d.; n=3 plugs per group.  P<0.01. C. Flow cytometric quantification of neutrophil infiltration into plugs containing CM collected from ECFCs+MSCs, ECFCs alone, and MSCs alone. Bars represent mean±s.d.; n=3 plugs per group.  P<0.01; *** P<0.001.
Figure 13B:
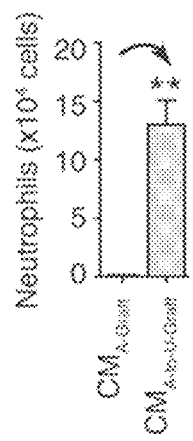
Figure 13C:
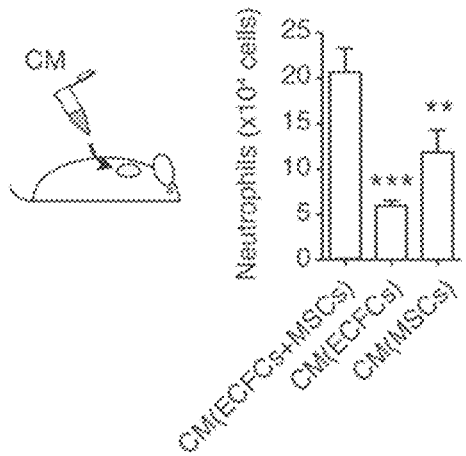

Example 4. Pro-Vascularization Activity of Neutrophils is Regulated by Secreted Factors To gain further insights into how grafts engage host neutrophils, we collected daily samples of conditioned media (CM) from U-Grafts over 8 days in vitro (i.e., until they became A-Grafts) (FIG. 12A). Subcutaneous plugs containing CM from U-Grafts robustly recruited neutrophils in nude mice (FIG. 12B). Neutrophil recruitment by CM(U-Grafts) was significantly higher than by CM(ECFCs) and CM(MSCs) separately (FIG. 13). However, plugs containing CM from A-Grafts had no detectable neutrophils, a decline that occurred progressively and coincided with the assembly of cells into vascular networks (FIG. 12C). Moreover, human cells retrieved from A-Grafts could immediately regain ability to recruit neutrophils when used in new U-Grafts (FIG. 13). Thus, neutrophil recruitment was mediated by secreted factors and was directly related to the state of the vascular cells (assembled vs. unassembled) within the grafts.

Figure 12E:
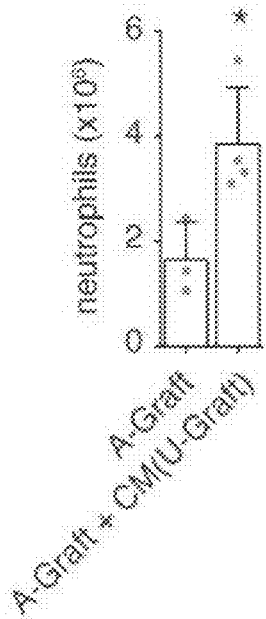
Figure 12F:
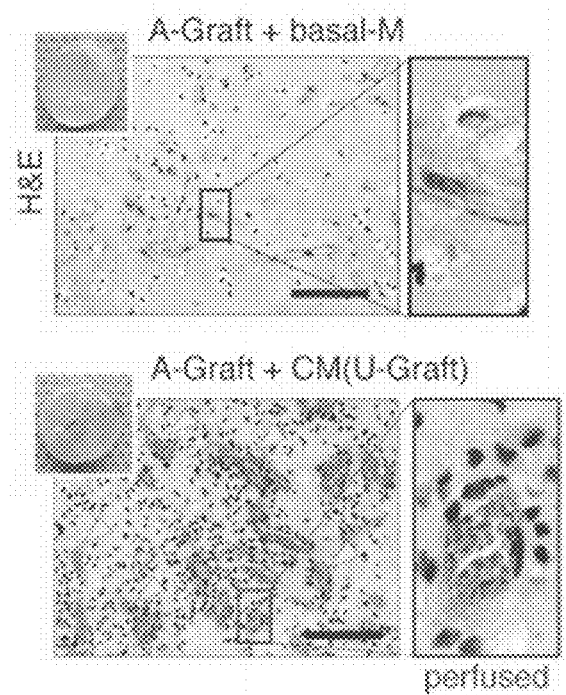
Figure 12G:
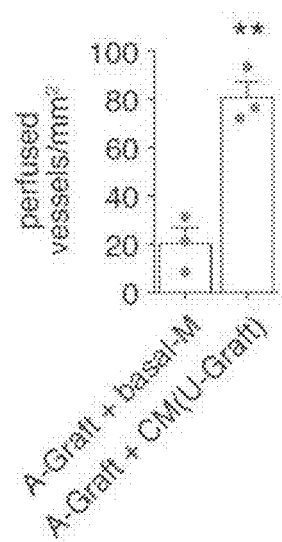
Figure 12H:
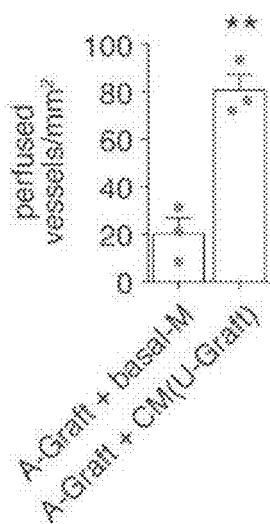
Figure 12I:
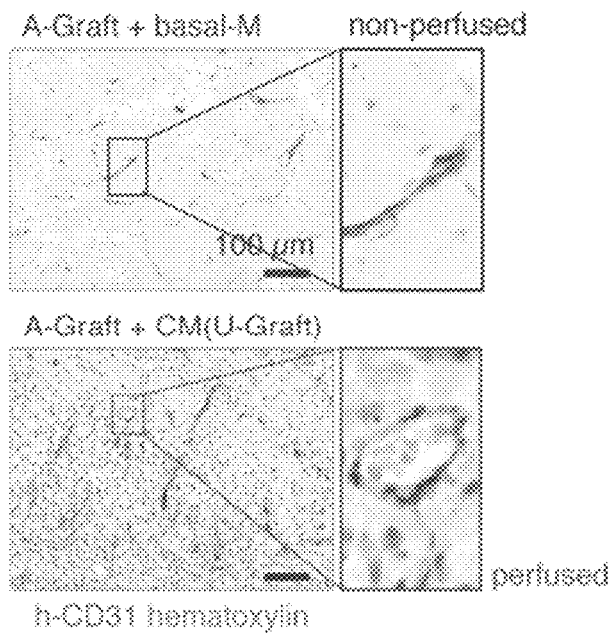
Figure 12J:
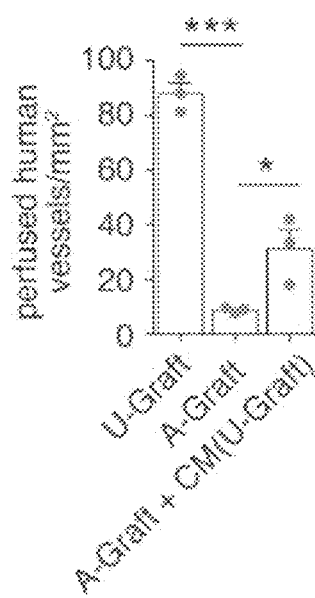
Figure 16A:
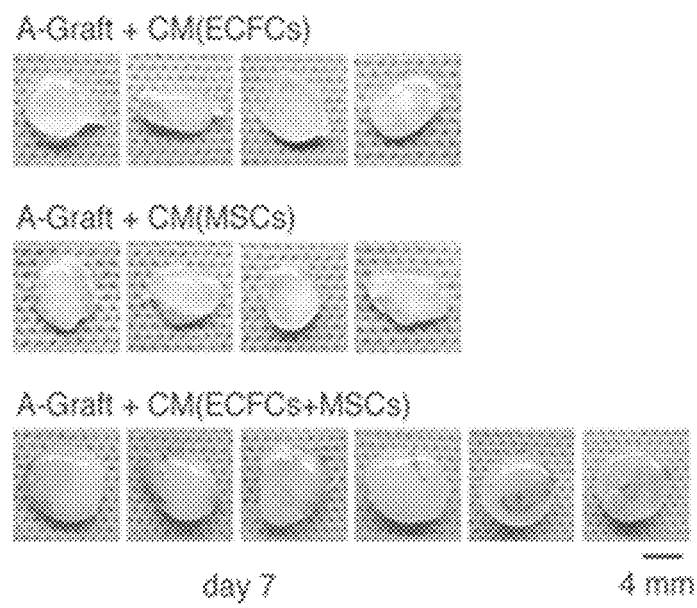
FIGS. 16A-C. Vascularization of A-Grafts by factors secreted from U-Grafts. (A) A-Grafts were impregnated in CM from either ECFCs, MSCs, or from ECFCs+MSCs and were then implanted into nude mice. Macroscopic views of the explants at day 7. (B) H&E staining at day 7 of explanted A-Grafts that were impregnated in CM from either ECFCs, MSCs, or ECFCs+MSCs. Perfused vessels marked by arrowheads. (C) Microvessel density at day 7. Bars represent mean±s.d.; n=4 mice per group. ** P<0.01.
Figure 16B:
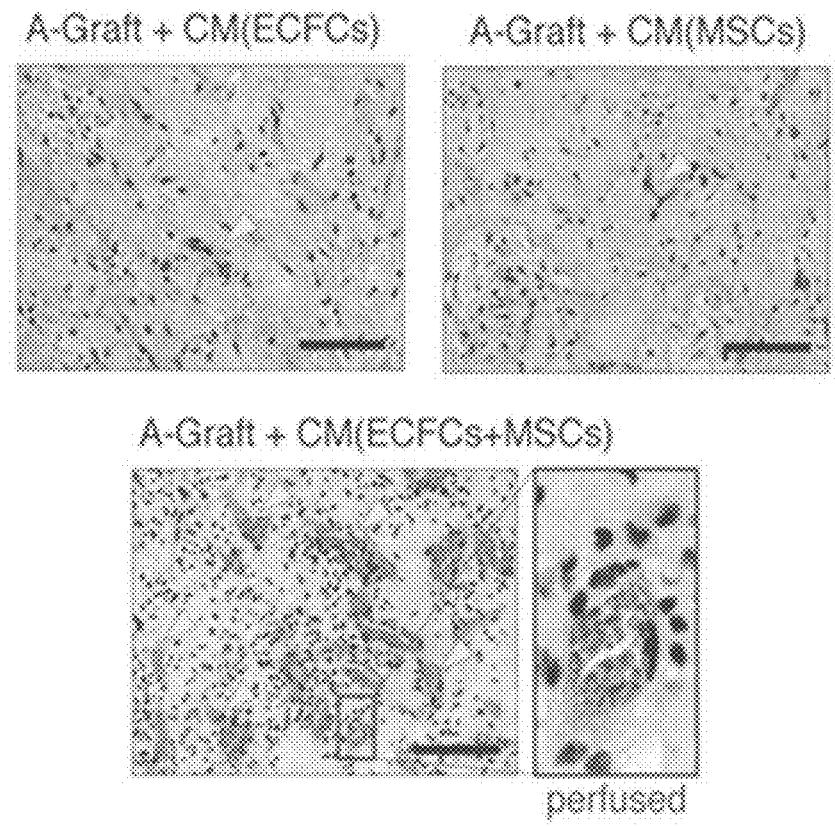
Figure 16C:
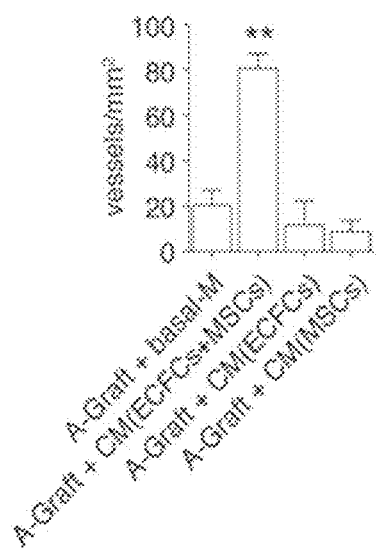

Next, we studied whether exposing A-Grafts to CM from U-Grafts could thus enhance engraftment of assembled bioengineered vessels (FIG. 12D). First, we observed that A-Grafts that were simply impregnated once with CM(U-Graft) at the time of implantation contained significantly more neutrophils at day 2 than the control (FIG. 12E). In addition, A-Grafts+CM(U-Graft) contained an extensive network of perfused microvessels at day 7 (FIG. 12F, G). Moreover, the extent to which CM(U-Grafts_induced revascularization of A-Grafts was significantly higher than that of CM(ECFCs) and CM(MSCs) separately (FIG. 16). Examination of human-specific (h-CD31+) lumens revealed that A-Grafts+CM(U-Graft) comprised perfused human microvessels that carried murine erythrocytes, indicating successful connection of pre-assembled vessels with the host circulatory system (FIG. 12H). In contrast, A-Grafts+basal-M had a significantly lower number of perfused human lumens at day 7 (8.7±0.6 vessels/mm$^2$ vs. 31.2±7.0 vessels/mm$^2$ in A-Grafts+CM(U-Graft)) (FIG. 12I). Instead, human ECFCs remained organized as non-perfused cellular cords (FIGS. 12F, H). Thus, a critical difference between U-Grafts and A-Grafts resides in the presence or absence of secreted factors that recruit and activate host neutrophils, which in turn modulate graft vascularization. Importantly, exogenous provision of factors from U-Grafts could reengage neutrophils and enhance revascularization in A-Grafts.

Example 5. Inhibition of Notch Signaling Promotes Re-Vascularization

Figure 14A:
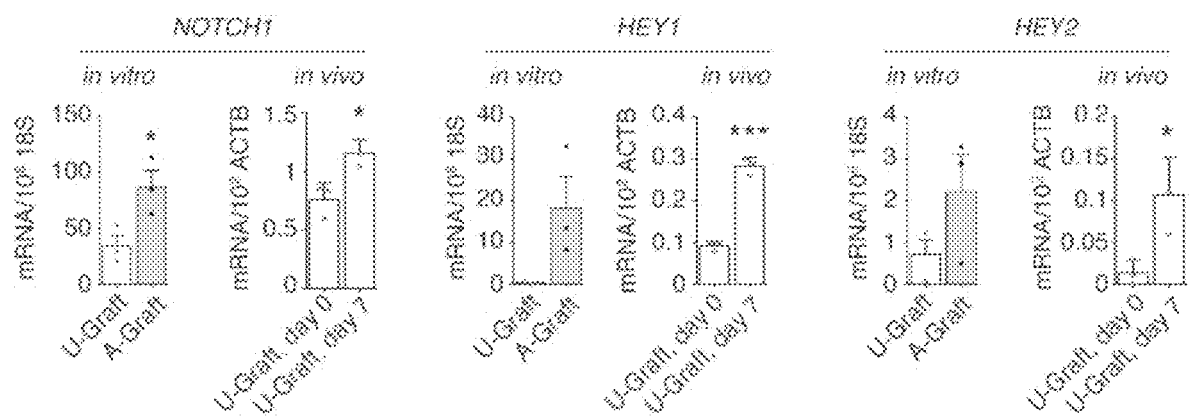
Figure 14A:
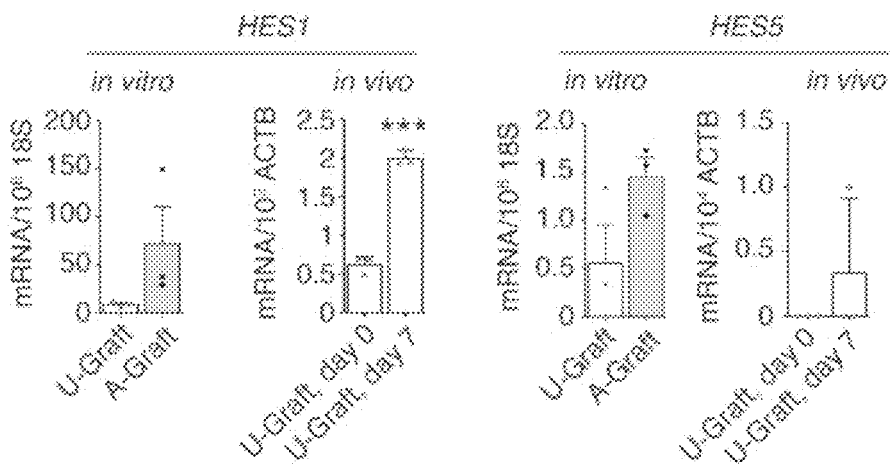
Figure 14B:
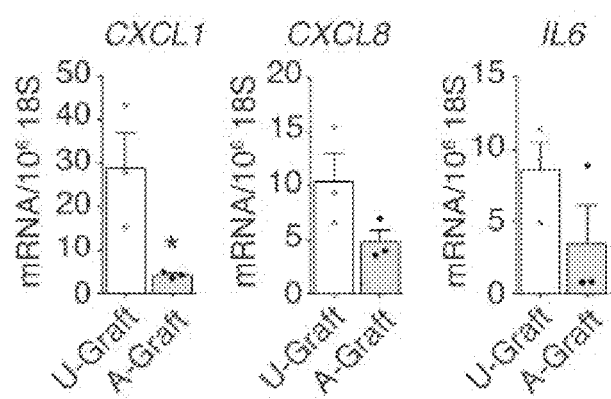
Figure 14C:
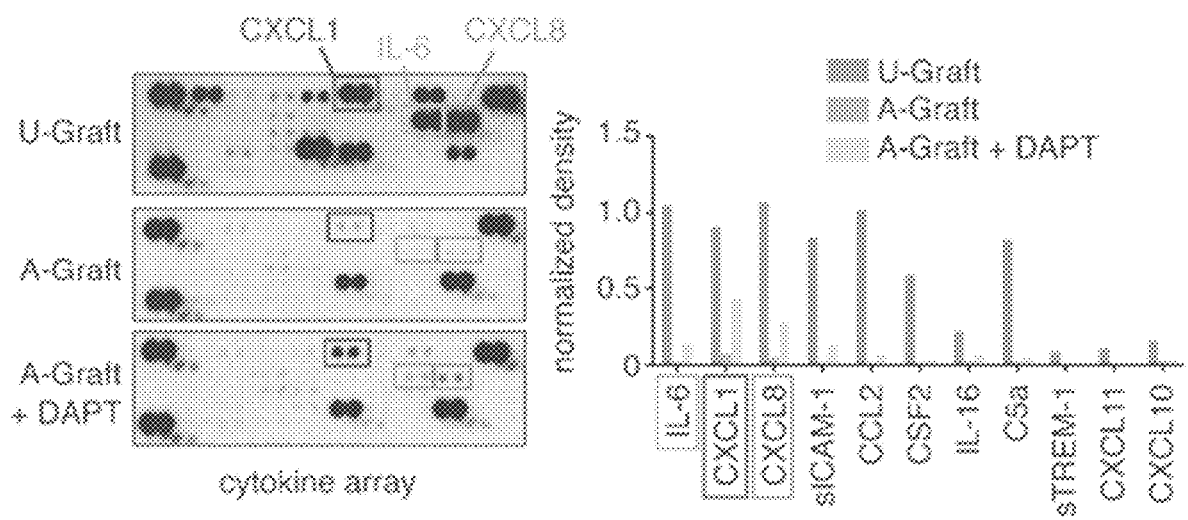

Microvascular stability is associated with activation of Notch in the endothelium[25,26]. However, the relation between endothelial Notch signaling and neutrophil activity in the context of grafting remains unexplored. mRNA expression of NOTCH1, as well as several downstream mediators of Notch signaling (HEY1, HEY2, HES1, and HES5), was upregulated in ECFCs from A-Grafts compared to U-Grafts (FIG. 14A). Moreover, expression of human-specific genes (NOTCH1, HEY1, HEY2, and HES1) were all significantly up-regulated by the human cells in implanted U-Grafts over a 7-day period confirming the association between vascular maturity and Notch. Inversely, expression levels of several cytokines with neutrophil chemoattractant activity (namely, CXCL1, CXCL8, and IL6) were downregulated in ECFCs from A-Grafts (FIG. 14B), which coincided with reduced neutrophil presence. Cytokine analyses of CM confirmed widespread downregulation of numerous neutrophil chemoattractants in A-Grafts vs. U-Grafts (FIG. 14C). Of note, exposing A-Grafts to the Notch inhibitor DAPT (a γ-secretase inhibitor) for 24 h reactivated the expression of several cytokines (most significantly CXCL1, CXCL8, and IL6) (FIG. 14C), suggesting a relationship between Notch activation and the secretion of neutrophil chemoattractants by the vasculature. Moreover, the use of antibodies to specifically block each of the identified cytokines (most significantly IL6 and CXCL8) in CM from U-Grafts interfered with the recruitment of neutrophils into subcutaneous plugs (FIG. 14D), whereas plugs containing CM from DAPT-treated A-Grafts recruited significantly more neutrophils than plugs with CM from untreated A-Grafts (FIG. 14D).

Figure 14H:
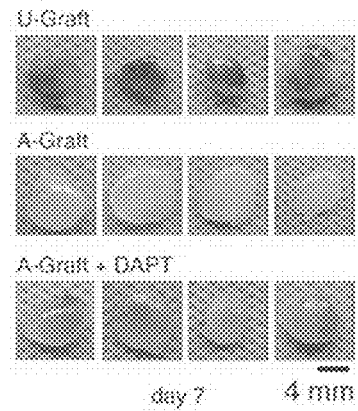
Figure 14I:
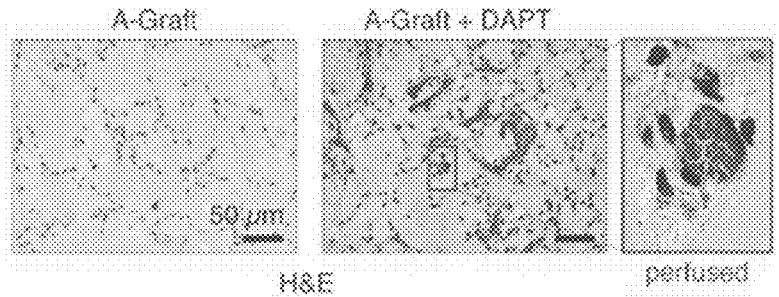
Figure 14J:
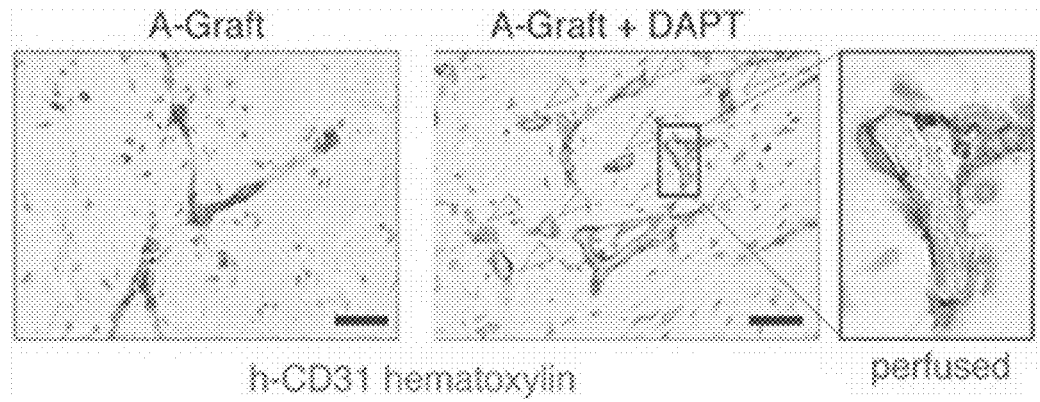
Figure 14K:
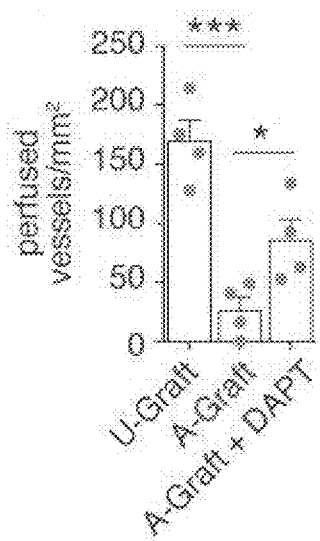
Figure 15:
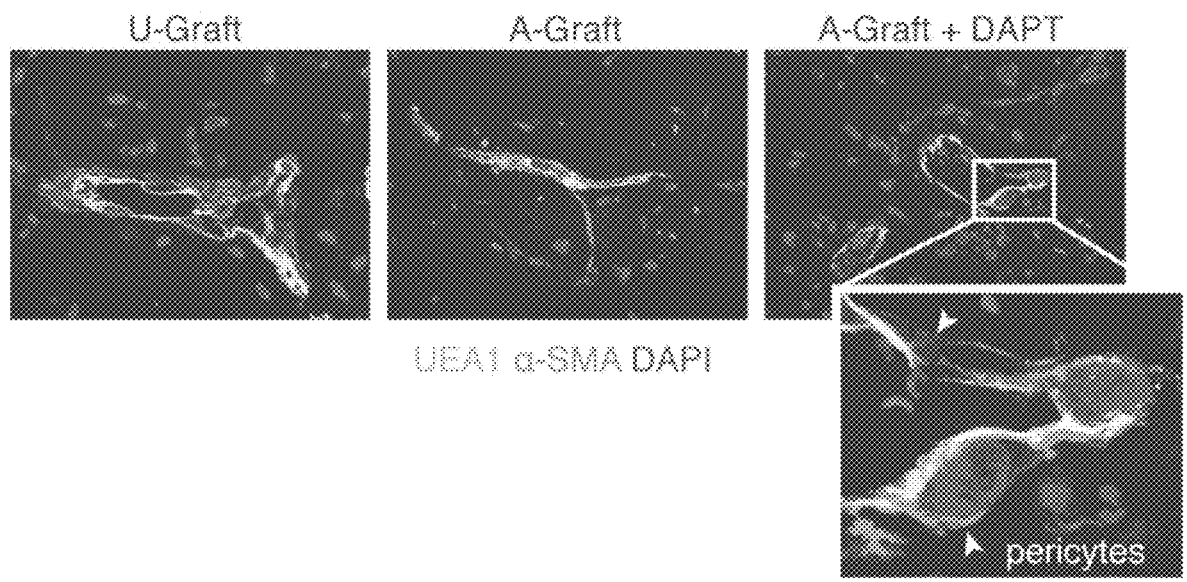
FIG. 15. Perivascular coverage in bioengineered vessels. U-Grafts, A-Grafts, and A-Grafts+DAPT were implanted into nude mice and explanted at day 7. Immunofluorescent staining of section from the explants. Human vessels were visualized as UEA-1+ structures (green). Perivascular cells were stained with α-smooth muscle actin (SMA) antibodies (red). Nuclei stained by DAPI.

To further elucidate the significance of secreted cytokines, we examined the effect of a non-peptide CXCR2 antagonist (SB225002) on the vascularization of U-Grafts. CXCR2 is a receptor for both CXCL8 and CXCL1, and previous studies have shown that SB225002 effectively inhibits neutrophil chemotaxis in response to CXCL8 both in vitro and in vivo[34]. Indeed, SB225002 treatment significantly impaired neutrophil presence in our implanted U-Grafts at day 2 (FIG. 14E). Importantly, U-Grafts that were implanted into SB225002-treated mice had significantly lower microvessel densities than those implanted into control animals (FIG. 14F). To put this result in context, SB225002-treatment produced a reduction in vascularity that was similar to the reduction produced by depletion of host neutrophils with α-Ly6G antibody (FIG. 14F). Moreover, a combination treatment with α-Ly6G+SB225002 further reduced microvessel density in U-Grafts (down to ~8 vessels/mm$^2$), although the differences in reduction between the combination and each individual treatment were not statistically significant. Nevertheless, this additional reduction in microvessel density due to the combination treatment might suggest participation of an additional type of host CXCR2$^+$ cells that, together with neutrophils, mediate graft vascularization. Next, we examined whether deactivation of Notch could rescue the inherent lack of revascularization in A-Grafts. To this end, we incubated A-Grafts with DAPT for 24 h ahead of their implantation into mice. Compared to untreated grafts, DAPT-treated A-Grafts had significantly more neutrophils at day 2 (FIG. 14G). In addition, DAPT-treated A-Grafts contained more extensive networks of perfused microvessels that were unequivocally human after 7 days in vivo (FIG. 14H-J), and the difference in microvascular density between DAPT-treated and untreated grafts was significant (FIG. 14K). Importantly, human vessels in DAPT-treated A-Grafts were surrounded by perivascular α-SMA+ cells (FIG. 15), indicating that the transient inhibition of Notch signaling did not compromise proper perivascular coverage.

Example 6. Unassembled Vascular Cells Recruit Host Neutrophils, which in Turn Mediate Vasculogenesis Using shRNA, the genes encoding each of the candidate factors (i.e., CXCL8, IL-6, and CXCL1) are knocked out in unassembled vascular cells and the effect on neutrophil recruitment (flow cytometry) and graft vascularization (histology and IHC) upon subcutaneous implantation into nude mice is determined. In addition, the effect of over-expressing (via inducible lentiviral vectors) each candidate factor in assembled vascular cells on formation of anastomoses between host and donor vessels is determined. Lastly, whether blocking Notch signaling enhances the expression of our candidate cytokines and the revascularization of assembled vascular cells is determined using three approaches: (i) inhibition of γ-secretase; (ii) Notch inhibition with a decoy Notch-1 Fc peptide; and (iii) inducible genetic ablation of Notch.

Example 7. Ex Vivo Stimulated-Neutrophils Revascularize Assembled Vascular Cells (A-Graft)

First, whether neutrophils can be stimulated ex vivo to acquire the alternative phenotype seen in unassembled cells (U-grafts) is evaluated. To this end, in vitro, normal murine bone marrow (BM)-derived (or blood-derived) neutrophils are incubated with: 1) conditioned medium (CM) collected from unassembled cells (U-grafts) for 0-48 hours; and 2) 1-100 ng/mL of recombinant TGFβ-1, -2, and -3 for 0-48 hours. To determine the significance of TGFβ activation, inhibitors of the TGFβ pathway (SB431542, SIS3, and ITD1) as well as TGFβ-R$^{-/-}$ neutrophils are used. For each treatment, effects of both dose and time on gene expression in the stimulated neutrophils are analyzed. Both LPS-derived and unassembled cells U-graft-derived neutrophils serve as controls for classical and alternative activation, respectively. Whether stimulated neutrophils can mediate revascularization of A-grafts is then evaluated. To this end, ex vivo-stimulated neutrophils are injected at the implantation site of assembled grafts (A-grafts) and the extent of vascularization quantified at day 7. Efficacy is studied using various regimens ranging from one single dose (10 million neutrophils) at day 0 to daily injections of activated neutrophils.

Example 8. Human Tissue Grafts can be Revascularized Using Conditioned Medium (CM) from U-Grafts, Select Cytokines and Notch Inhibitors, and Ex Vivo-Stimulated Neutrophils De-identified samples of 1) normal subcutaneous white adipose tissue and 2) iliac crest corticocancellous bone are obtained. The following strategies to enhance revascularization of these human grafts upon implantation into nude mice are evaluated: 1) pre-treatment with CM from unassembled vascular cells (U-grafts); 2) pre-treatment with cytokines and Notch inhibitors to increase host neutrophil engagement; and 3) provision of alternatively activated (ex vivo-stimulated) neutrophils. The latter strategy is conducted with both murine and human neutrophils obtained from bone marrow aspirates and/or peripheral blood from healthy volunteers. For each of these strategies, revascularization is evaluated after 1 week (histology; IHC; perfusion of UEA-1 lectin; and hypoxia measured by hypoxyprobe-1 (Hofer, et al. British Journal of plastic surgery 2005; 58: 1104-114). Then, overall human cell survival is assessed using human specific antibodies to identify adipocytes (vimentin+/perilipin-A+; fat grafts) and osteoblasts/osteocytes (vimentin+/osterix+; bone grafts), as we previously described (Lin, et al. Proc. Natl. Acad. Sci. USA 2014; 111: 10137-10142). Apoptotic cells are identified by TUNEL assay. Lastly, assays are conducted to validate functionality of the human grafts (adipocyte response to insulin in adipose tissues (Ozcan, et al. Science 2004; 306: 457-461; active mineralization in bone tissues (Lin, et al. Proc. Natl. Acad. Sci. USA 2014; 111: 10137-10142) at 1-4 weeks.

Example 9. Vascularization of U-Grafts in Immune-Competent Mice

Figure 17A:
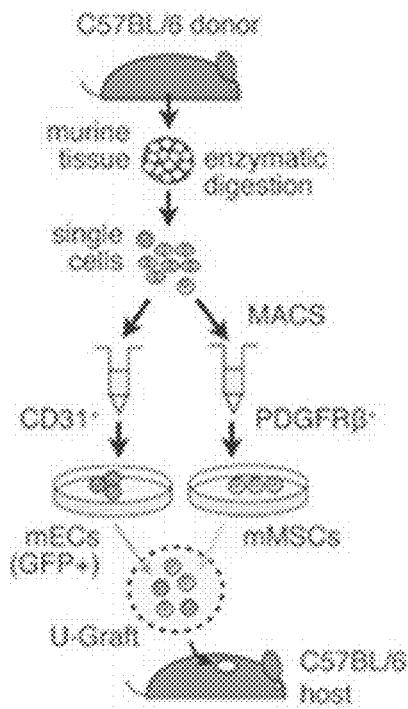
FIGS. 17A-F. Host neutrophils are indispensable for graft vascularization in a syngeneic murine C57BL/6 model. (A) Schematic of syngeneic grafting model on C57BL/6 mice. Subcutaneous tissues from C57BL/6 mice were enzymatically digested into single cell suspension. Magnetic-activated cell sorting (MACS) was performed to purify mouse ECs (mECs; CD31+) and mouse MSCs (mMSCs; PDGFRβ+). mECs were lentivirally transduced to express GFP. GFP-mECs and mMSCs were then implanted as U-Grafts into host C57BL/6 mice. (B) Neutrophils were depleted with α-Ly6G antibodies in C57BL/6 mice. U-Graft containing GFP-mECs and mMSCs were implanted at day 0. Control (IgG antibody) and α-Ly6G treatments were initiated at day −2 and maintained until day 7. Lower panels show macroscopic views of the subcutaneous grafts at day 7. (C) H&E staining of U-Grafts explanted at day 7. Insets are macroscopic views of the explants. Perfused vessels were identified as luminal structures containing RBCs (arrowheads). (D) Density of perfused blood vessels at day 7. Bars represent mean±s.d.; n=3 mice per group. *** P<0.001 compared to control. (E) Vessels lined by donor mECs were identified by GFP and perivascular coverage by α-SMA+ staining. Nuclei stained by DAPI. (F) Flow cytometry analysis of murine U-Grafts implanted in C57BL/6 host. Cytometric analyses included blood samples and cells retrieved from explanted U-Grafts at day 2. B cells were identified as mCD19-positive cells and T cells as mCD3-positive. Scale bars: 4 mm (B) and 100 µm (C, E).
Figure 17B:
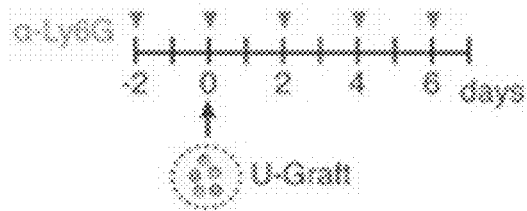
Figure 17B:
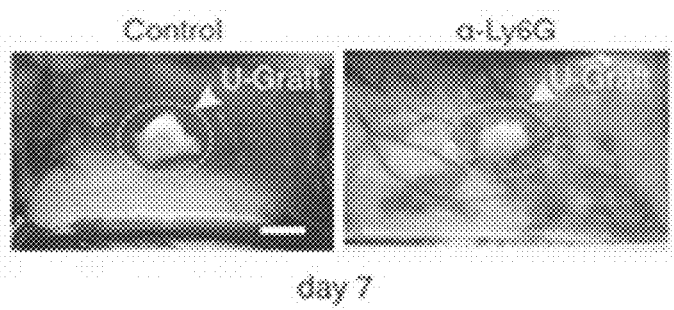
Figure 17C:
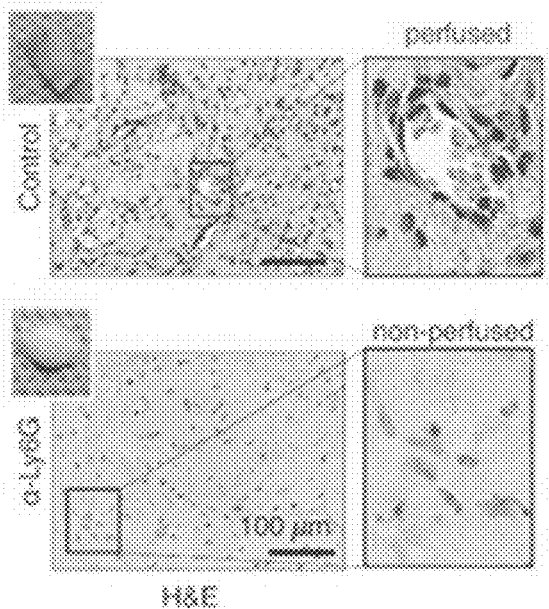
Figure 17D:
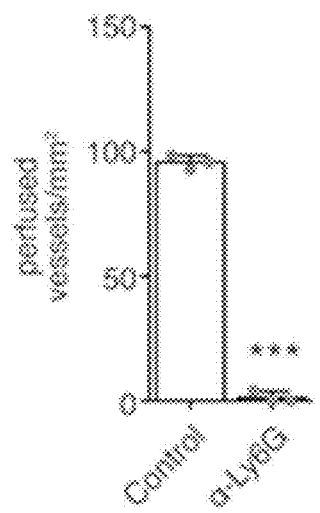
Figure 17E:
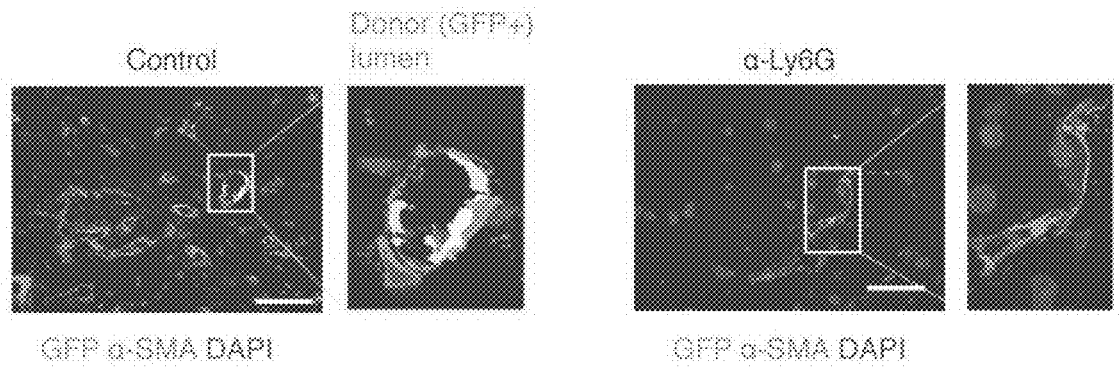

To validate the dependency of graft vascularization on host neutrophils in immune-competent hosts, we generated unassembled U-Grafts using murine autologous endothelial cells (ECs) and MSCs isolated from C57BL/6 mice (cells referred to as mECs and mMSCs) (FIG. 17A). These murine cells were isolated from excised subcutaneous tissues that were enzymatically digested and cells were purified by using magnetic beads with antibodies against murine CD31 (for mECs) and platelet-derived growth factor receptor-beta (PDGFRβ) (for mMSCs) via magnetic-activated cell sorting (MACS). Purified mECs and mMSCs were expanded in culture and their phenotype and purity were confirmed, as we previously described[18]. Murine mECs were transduced to express green fluorescent protein (GFP) (referred to as GFP-mECs) and combined with mMSCs to generate U-Grafts, which were then subcutaneously implanted into immunocompetent C57BL/6 mice. Implants were harvested at day 7 and histological (hematoxylin and eosin, H&E) examination revealed that extensive networks of blood microvessels had formed and contained murine erythrocytes, confirming perfusion (FIG. 17B, C). Microvessels were lined by the implanted GFP-mECs as confirmed by GFP immunostaining (FIG. 17E). In addition, GFP$^+$ microvessels were largely covered by alpha-smooth muscle actin (α-SMA)-expressing perivascular cells, indicating stability (FIG. 17E). Taken together, these data demonstrated that U-Grafts containing murine cells (mECs+mMSCs) can form microvascular networks in fully immune-competent hosts (C57BL/6 mice).

Next, we examined whether neutrophils were also indispensable for vascularization in immune-competent hosts (FIG. 17B). As in the previous xenograft model, depletion of neutrophils was also detrimental on vascularization in syngeneic grafts; murine U-Grafts implanted into α-Ly6G-treated C57BL/6 mice completely lacked perfused vessels (neither donor nor host) at day 7 (FIG. 17C,E) and microvascular density was negligible and significantly lower (1.4±1.3 vessels/mm$^2$) than in the control group (95.6±4 vessels/mm$^2$) (FIG. 17D).

Figure 17F:
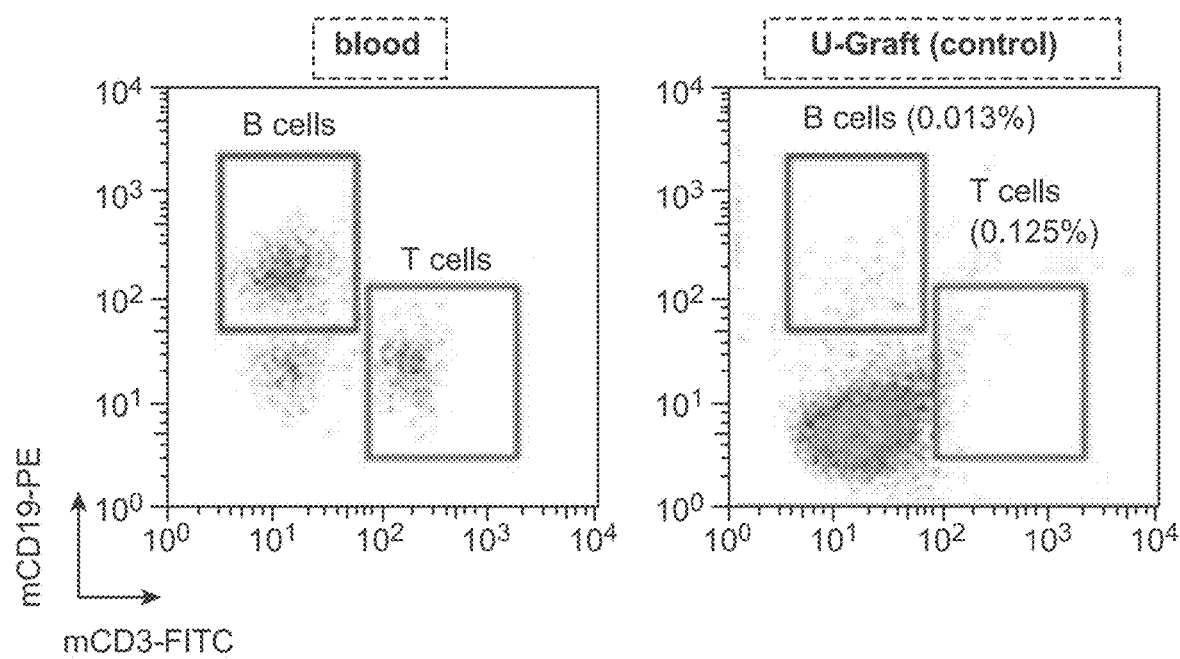

In addition, we examined the presence of lymphocytes in murine U-Grafts implanted into immune-competent C57BL/6 hosts. To this end, grafts were explanted at day 2, enzymatically digested, and the retrieved cells were analyzed by flow cytometry. We examined the presence of mCD45$^+$/mCD19$^+$ B cells and mCD45$^+$/mCD3$^+$ T cells and found that the presence of both B and T cells in the grafts was minimal (<0.2%) and certainly significantly lower than the myeloid contribution (mCD11b+ cells were ~56.7% at day 2 in syngeneic murine U-Grafts implanted into C57BL/6) (FIG. 17F). Indeed, U-Grafts implanted into α-Ly6G-treated mice failed to vascularize despite normal levels of circulating lymphocytes. In summary, we demonstrated that 1) syngeneic murine U-Grafts did vascularize in immune-competent host; 2) neutrophil participation was critical for the vascularization of syngeneic U-Grafts; and 3) lymphocyte presence in the grafts was minimal.

Figure 18A:
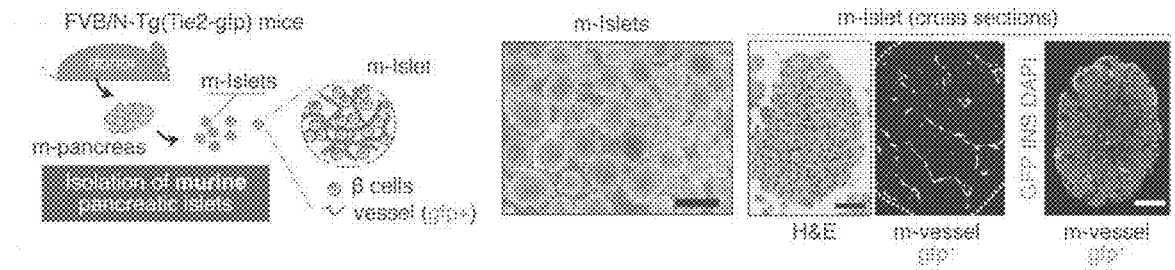
FIGS. 18A-B. Isolation of murine and human pancreatic islets. (A) Mouse pancreatic islets isolated from FVB/N-Tg (Tie2-gfp) mice. Cross sections of isolated m-Islets show structural integrity (H&E) and insulin (INS) expression by β-cells. Microvessels were easily identified by gfp. (B) Human islets were obtained from the Pancreatic Isolation Core at MGH. Cross sections of isolated h-Islets show structural integrity (H&E) and INS expression. Microvessels identified by both UEA-1 and h-CD31 expression.
Figure 18B:
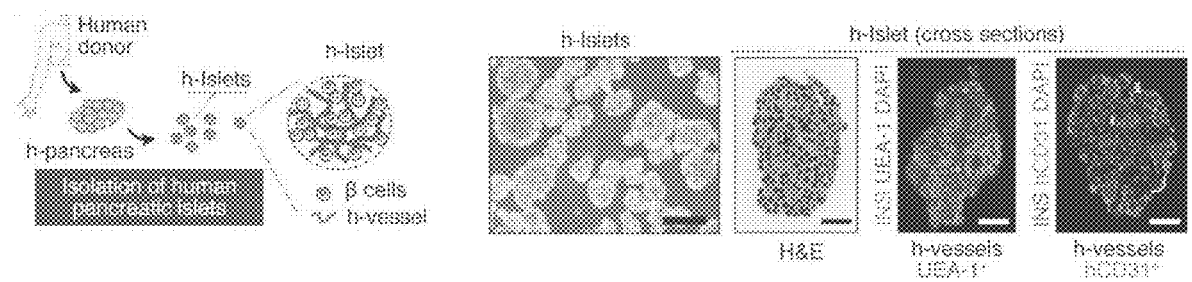

Example 10. Identification of Microvessels in Murine and Human Pancreatic Islets To move from graft models to primary islets grafts, we implemented methods to isolate pancreatic islets and to identify islet vasculature. Pancreatic islets were isolated from FVB/N-Tg(Tie2-gfp) mice (FIG. 18A). These mice bear a gfp transgene expressed under the control of Tie2, and thus are well suited for imaging blood vessels. Briefly, the pancreas was dissected and digested. Murine islets (m-Islets) were then purified by filtration and gradient centrifugation. This method produces ~150 islets per pancreas. Of note, isolated m-Islets were uniformly undamaged (H&E), β-cells displayed normal insulin expression, and microvessels were easily identified by gfp (FIG. 18A). Human pancreatic islets (h-Islets) were of the quality intended for transplantation and were isolated by standard clinical methods (see, e.g., Shapiro et al., *Nat. Rev. Endocrinol.* 13(5): 268-277, 2017). The h-Islets displayed proper structural integrity (H&E) and robust insulin expression (FIG. 18B). Microvessels in h-Islets were easily identified by both UEA-1 lectin binding and by h-CD31 expression (FIG. 18B).

Example 11. Bioengineering an Interface for Pancreatic Islets

Figure 19A:
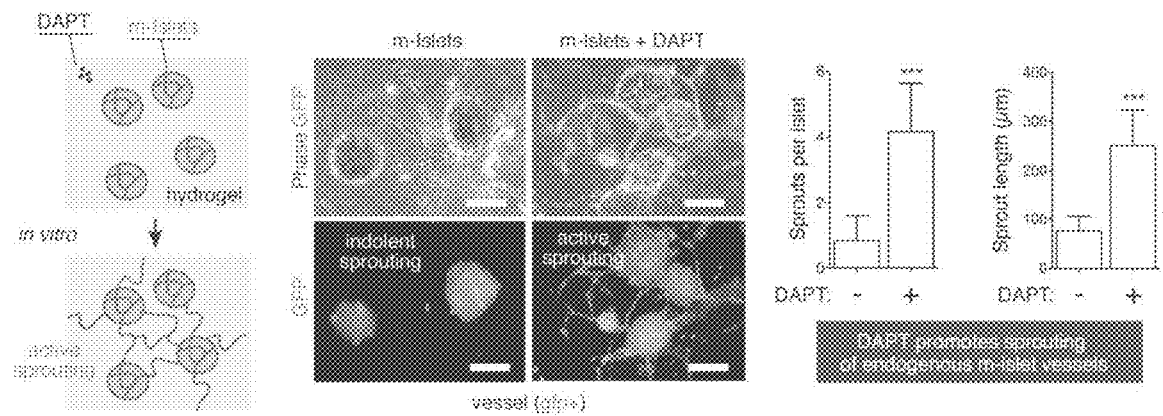
FIGS. 19A-B. Effect of DAPT and unassembled ECFCs on isolated pancreatic islets. (A) Effect of DAPT on vascular sprouting of m-Islet embedded in hydrogel. Vessels identified by gfp. (B) Effect of unassembled DsRed-ECFCs on m-Islet embedded in hydrogel. Interconnectivity between newly formed ECFC-lined vessels (DsRed+) and m-Islets vasculature (gfp+) was enhanced in the presence of DAPT. All experiments were done in vitro for 7 days.
Figure 19B:
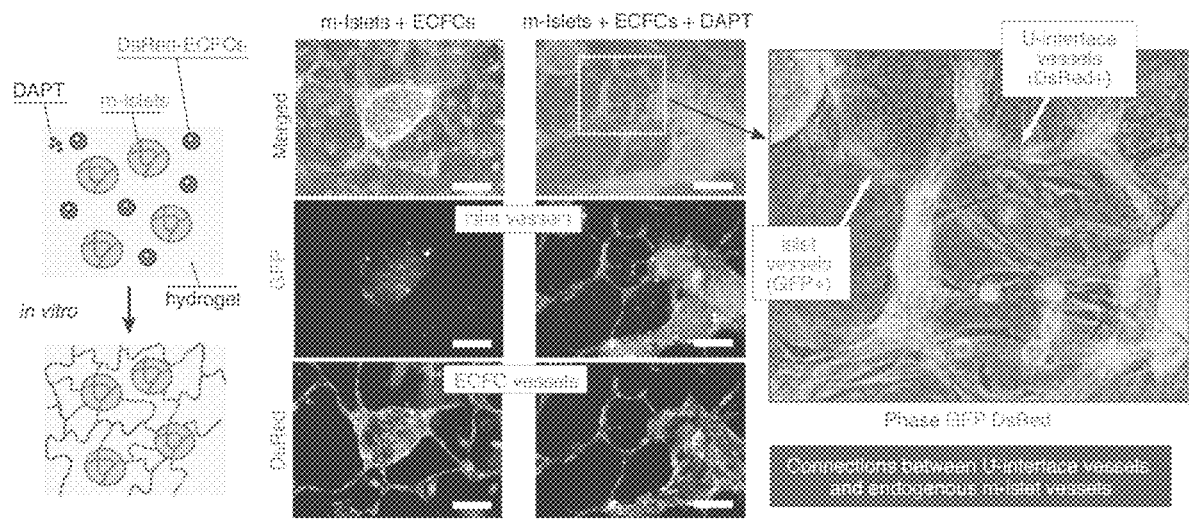

In order to develop an interface for the engraftment of islets, we embedded isolated m-Islets in our hydrogel in the presence or absence of DAPT (a γ-secretase inhibitor) and examined the effect on the vasculature of islets for 7 days. We found that DAPT treatment of m-Islets stimulated sprouting activity of their endogenous gfp+ microvessels (both number and length of sprouts were significantly higher), whereas untreated islets displayed indolent sprouting activity (FIG. 19A). This is consistent with previous data in which transiently blocking Notch enhanced the revascularization potential of A-grafts (FIG. 14) (52). We also examined the effect of unassembled DsRed-ECFCs (FIG. 19B). We found that the presence of m-Islets did not impede ECFC assembly into vascular networks. Moreover, the newly formed ECFC-lined vessels (DsRed+) interacted with the gfp+ vasculature of the m-Islets, and this interconnectivity was enhanced in the presence of DAPT (FIG. 19B). Taking together, this data reinforced the notion of using an interface with unassembled ECFCs and Notch inhibitors as a means to reengage the otherwise indolent vasculature of donor pancreatic islets.

Example 12. Improved In Vivo Vascularization of Interface-Islet Constructs

Figures 20A, 20B:
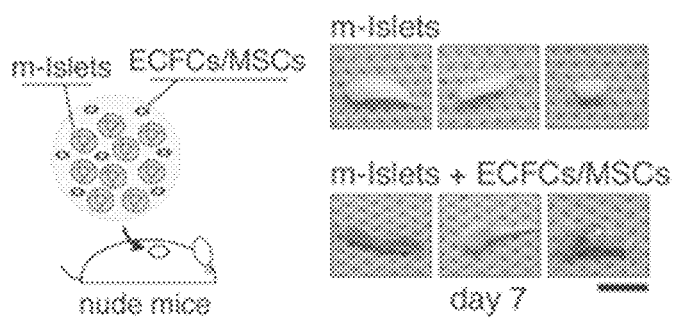
FIGS. 20A-E. In vivo vascularization of interface-islet constructs. (A) Constructs containing 500 m-Islets with and without unassembled human ECFCs/MSCs were transplanted subcutaneously into nude mice for 7 d. (B) Macroscopic views of explanted constructs. (C) H&E staining at day 7. Arrowheads=perfused vessels. (D) Density of perfused microvessels in explanted constructs (n=3). (E) Staining of human vessels (UEA-1+) in constructs with ECFCs/MSCs.
Figure 20C:
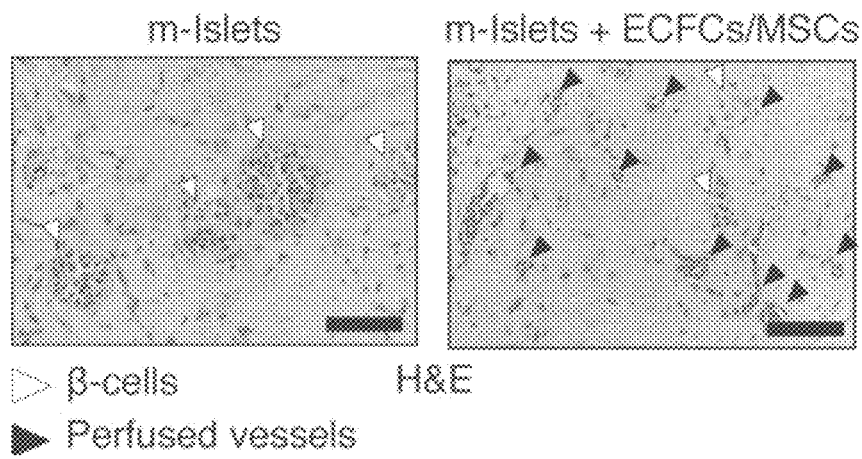
Figure 20D:
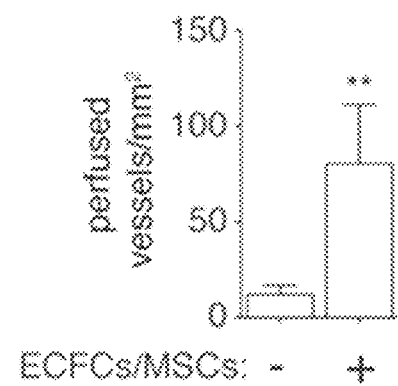
Figure 20E:
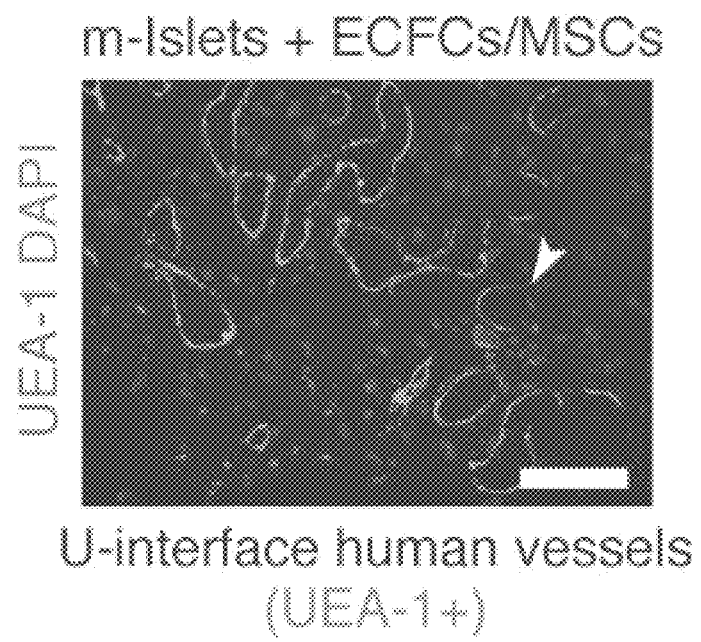

To examine the vascularization potential of the islet interface in vivo, we generated constructs containing 500 m-Islets with and without unassembled human ECFCs/MSCs (4×105 cells; 1:1 ratio). Constructs were then subcutaneously transplanted into nude mice for 7 days (FIG. 20A). Macroscopic views of the explants suggested that constructs containing m-Islets+interface cells (ECFCs/MSCs) were more vascularized than those with only m-Islets (FIG. 20B). Indeed, histological examination confirmed that constructs containing ECFCs/MSCs had considerably more perfused vessels than those containing only m-Isles (FIG. 20C). The difference in vascular density between the two groups was statistically significant (n=3) (FIG. 20D). The increased vascularity was due to the formation of an extensive network of human (UEA-1+) ECFC-lined blood vessels (FIG. 20E). These in vivo data support our notion of using an interface with unassembled ECFCs/MSCs as a means to improve the vascularity of constructs with pancreatic islets.

REFERENCES

1. Griffith, L. G. & Naughton, G. Tissue Engineering—Current Challenges and Expanding Opportunities. Science 295, 1009-1014 (2002).
2. Rouwkema, J., Rivron, N. C. & Van Blitterswijk, C. A. Vascularization in tissue engineering. Trends Biotechnol. 26, 434-441 (2008).
3. Novosel, E. C., Kleinhans, C. & Kluger, P. J. Vascularization is the key challenge in tissue engineering. Adv. Drug Deliv. Rev. 63, 300-311 (2011).
4. Schechner, J. S. et al. In vivo formation of complex microvessels lined by human endothelial cells in an immunodeficient mouse. Proc. Natl. Acad. Sci. USA 97, 9191-9196 (2000).
5. Chen, Y.-C. et al. Functional Human Vascular Network Generated in Photocrosslinkable Gelatin Methacrylate Hydrogels. Adv. Funct. Mater. 22, 2027-2039 (2012).
6. Jain, R. K., Au, P., Tam, J., Duda, D. G. & Fukumura, D. Engineering vascularized tissue. Nat. Biotechnol. 23, 821-823 (2005).
7. Melero-Martin, J. M. et al. Engineering robust and functional vascular networks in vivo with human adult and cord blood-derived progenitor cells. Circ. Res. 103, 194-202 (2008).
8. Traktuev, D. O. et al. Robust functional vascular network formation in vivo by cooperation of adipose progenitor and endothelial cells. Circ. Res. 104, 1410-1420 (2009).
9. Chen, X. et al. Rapid anastomosis of endothelial progenitor cell-derived vessels with host vasculature is promoted by a high density of cotransplanted fibroblasts. Tissue Eng. Part A 16, 585-594 (2010).
10. Moisidis, E., Heath, T., Boorer, C., Ho, K. & Deva, A. K. A Prospective, Blinded, Randomized, Controlled Clinical Trial of Topical Negative Pressure Use in Skin Grafting. Plast. Reconstr. Surg. 114, 917-922 (2004).
11. Larry, M. W. & Eber L. L. S. Considerations in nerve repair. Proceedings (Baylor University. Medical Center) 16, 152-156 (2003).
12. Giannoudis, P. V., Dinopoulos, H. & Tsiridis, E. Bone substitutes: An update. Injury 36, S20-S27 (2005).
13. Kølle, S., Fischer-Nielsen, A., Mathiasen, A. B. & Elberg, J. J. Enrichment of autologous fat grafts with ex-vivo expanded adipose tissue-derived stem cells for graft survival: a randomised placebo-controlled trial. Lancet 13, 1113-1120 (2013).
14. Mohr, F. W. et al. Coronary artery bypass graft surgery versus percutaneous coronary intervention in patients with three-vessel disease and left main coronary disease: 5-year follow-up of the randomised, clinical SYNTAX trial. Lancet 381, 629-638 (2013).
15. Serruys, P. W. et al. Percutaneous Coronary Intervention versus Coronary-Artery Bypass Grafting for Severe Coronary Artery Disease. N. Engl. J. Med. 360, 961-972 (2009).
16. Rogers, G. F. & Greene, A. K. Autogenous bone graft: basic science and clinical implications. J. Craniofac. Surg. 23, 323-327 (2012).
17. Melero-Martin, J. M. et al. In vivo vasculogenic potential of human blood-derived endothelial progenitor cells. Blood 109, 4761-4768 (2007).
18. Lin, R.-Z., Chen, Y.-C., Moreno-Luna, R., Khademhosseini, A. & Melero-Martin, J. M. Transdermal regulation of vascular network bioengineering using a photopolymerizable methacrylated gelatin hydrogel. Biomaterials 34, 6785-6796 (2013).

19. Melero-Martin, J. M. et al. Host myeloid cells are necessary for creating bioengineered human vascular networks in vivo. Tissue Eng. Part A 16, 2457-2466 (2010).
20. Fridlender, Z. G. et al. Polarization of tumor-associated neutrophil phenotype by TGF-beta: "N1" versus 'N2' TAN. Cancer Cell 16, 183-194 (2009).
21. Sagiv, J. Y. et al. Phenotypic diversity and plasticity in circulating neutrophil subpopulations in cancer. Cell Rep. 10, 562-573 (2015).
22. Nozawa, H., Chiu, C. & Hanahan, D. Infiltrating neutrophils mediate the initial angiogenic switch in a mouse model of multistage carcinogenesis. Proc. Natl. Acad. Sci. USA 103, 12493-12498 (2006).
23. Christoffersson, G. et al. VEGF-A recruits a proangiogenic MMP-9-delivering neutrophil subset that induces angiogenesis in transplanted hypoxic tissue. Blood 120, 4653-4662 (2012).
24. Jia, D., Huang, L., Bischoff, J. & Moses, M. A. The endogenous zinc finger transcription factor, ZNF24, modulates the angiogenic potential of human microvascular endothelial cells. FASEB J. 29, 1371-1382 (2015).
25. Suchting, S. et al. The Notch ligand Delta-like 4 negatively regulates endothelial tip cell formation and vessel branching. Proc. Nat.l Acad. Sci. USA 104, 3225-3230 (2007).
26. Roca, C. & Adams, R. H. Regulation of vascular morphogenesis by Notch signaling. Genes & Development 21, 2511-2524 (2007).
27. Nahrendorf, M. et al. The healing myocardium sequentially mobilizes two monocyte subsets with divergent and complementary functions. J. Exp. Med. 204, 3037-3047 (2007).
28. Grunewald, M. et al. VEGF-induced adult neovascularization: recruitment, retention, and role of accessory cells. Cell 124, 175-189 (2006).
29. Shojaei, F., Zhong, C., Wu, X., Yu, L. & Ferrara, N. Role of myeloid cells in tumor angiogenesis and growth. Trends Cell Biol. 18, 372-378 (2008).
30. De Palma, M. et al. Tie2 identifies a hematopoietic lineage of proangiogenic monocytes required for tumor vessel formation and a mesenchymal population of pericyte progenitors. Cancer Cell 8, 211-226 (2005).
31. De Palma, M., Venneri, M. A., Roca, C. & Naldini, L. Targeting exogenous genes to tumor angiogenesis by transplantation of genetically modified hematopoietic stem cells. Nat. Med. 9, 789-795 (2003).
32. Bekes, E. M. et al. Tumor-recruited neutrophils and neutrophil TIMP-free MMP-9 regulate coordinately the levels of tumor angiogenesis and efficiency of malignant cell intravasation. Am. J. Pathol. 179, 1455-1470 (2011).
33. Piccard, H., Muschel, R. J. & Opdenakker, G. On the dual roles and polarized phenotypes of neutrophils in tumor development and progression. Crit. Rev. Oncol. Hematol. 82, 296-309 (2012).
34. Massena, S. et al. Identification and characterization of VEGF-A-responsive neutrophils expressing CD49d, VEGFR1, and CXCR4 in mice and humans. Blood 126, 2016-2026 (2015).
35. Mantovani, A. The yin-yang of tumor-associated neutrophils. Cancer Cell 16, 173-174 (2009).
36. Fridlender, Z. G. & Albelda, S. M. Tumor-associated neutrophils: friend or foe? Carcinogenesis 33, 949-955 (2012).
37. Fridlender, Z. G. et al. Transcriptomic analysis comparing tumor-associated neutrophils with granulocytic myeloid-derived suppressor cells and normal neutrophils. PLoS ONE 7, e31524 (2012).
38. Cuartero, M. I. et al. N2 neutrophils, novel players in brain inflammation after stroke: modulation by the PPARγ agonist rosiglitazone. Stroke 44, 3498-3508 (2013).
39. Ma, Y. et al. Temporal neutrophil polarization following myocardial infarction. Cardiovasc. Res. 110, 51-61 (2016).
40. Fantin, A. et al. Tissue macrophages act as cellular chaperones for vascular anastomosis downstream of VEGF-mediated endothelial tip cell induction. Blood 116, 829-840 (2010).
41. Murdoch, C., Giannoudis, A. & Lewis, C. E. Mechanisms regulating the recruitment of macrophages into hypoxic areas of tumors and other ischemic tissues. Blood 104, 2224-2234 (2004).
42. Murdoch, C., Muthana, M., Coffelt, S. B. & Lewis, C. E. The role of myeloid cells in the promotion of tumour angiogenesis. Nat. Rev. Cancer 8, 618-631 (2008).
43. Benelli, R. et al. Neutrophils as a key cellular target for angiostatin: implications for regulation of angiogenesis and inflammation. FASEB J. 16, 267-269 (2002).
44. Baranski, J. D. et al. Geometric control of vascular networks to enhance engineered tissue integration and function. Proc. Natl. Acad. Sci. USA 110, 7586-7591 (2013).
45. Riemenschneider, S. B. et al. Inosculation and perfusion of pre-vascularized tissue patches containing aligned human microvessels after myocardial infarction. Biomaterials 97, 51-61 (2016).
46. Ausprunk, D. H., Knighton, D. R. & Folkman, M. J. Vascularization of normal and neoplastic tissues grafted to the chick chorioallantois. Role of host and preexisting graft blood vessels. Am. J. Pathol. 79, 597-618 (1975).
47. Nolan, D. J. et al. Molecular signatures of tissue-specific microvascular endothelial cell heterogeneity in organ maintenance and regeneration. Dev. Cell 26, 204-219 (2013).
48. Lee, J.-H. et al. Lung stem cell differentiation in mice directed by endothelial cells via a BMP4-NFATc1-thrombospondin-1 axis. Cell 156, 440-455 (2014).
49. Hu, J. et al. Endothelial cell-derived angiopoietin-2 controls liver regeneration as a spatiotemporal rheostat. Science 343, 416-419 (2014).
50. Kusumbe, A. P., Ramasamy, S. K. & Adams, R. H. Coupling of angiogenesis and osteogenesis by a specific vessel subtype in bone. Nature 507, 323-328 (2014).
51. Shen, Q. et al. Endothelial cells stimulate self-renewal and expand neurogenesis of neural stem cells. Science 304, 1338-1340 (2004).
52. White, J. R. et al. Identification of a potent, selective non-peptide CXCR2 antagonist that inhibits interleukin-8-induced neutrophil migration. J Biol Chem 273, 10095-10098 (1998).
52. Lin, R. Z. et al. Host non-inflammatory neutrophils mediate the engraftment of bioengineered vascular networks. Nat Biomed Eng 1(6): 0081 (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of improving vascularization or engraftment of an implanted tissue graft, the method comprising: contacting a tissue graft with:
   (i) a Notch inhibitor; and
   (ii) unassembled vascular cells, conditioned medium from unassembled vascular cells, ex vivo stimulated-neutrophils, or any combination thereof, for 0 to 48 hours.

2. The method of claim 1, wherein contacting the tissue graft is prior to tissue graft implantation, at the same time as tissue graft implantation, following tissue graft implantation, or any combination thereof.

3. The method of claim 1, wherein the Notch inhibitor is a γ-secretase inhibitor.

4. The method of claim 1, wherein the Notch inhibitor is a small molecule, an antisense molecule, a small interfering RNA, or a small hairpin RNA which is specific for a nucleic acid encoding any one of human NOTCH1, NOTCH2, NOTCH3, Notch ligand 4 (DLL4), hairy and enhancer of split 1 (HES1), hes family bHLH transcription factor 5 (HES5), hes related family bHLH transcription factor with YRPW motif 1 (HEY1), or hes related family bHLH transcription factor with YRPW motif 2 (HEY2).

5. The method of claim 1, wherein the Notch inhibitor is an antibody or antigen binding portion thereof that is specific for and inhibits the activity of a human NOTCH1, NOTCH2, NOTCH3, Notch ligand 4 (DLL4), hairy and enhancer of split 1 (HES1), hes family bHLH transcription factor 5 (HES5), hes related family bHLH transcription factor with YRPW motif 1 (HEY1), or hes related family bHLH transcription factor with YRPW motif 2 (HEY2) polypeptide.

6. The method of claim 1, wherein the unassembled vascular cells comprise a plurality of endothelial cells (EC) and mesenchymal stem cells (MSC), in a ratio of EC:MSC of about 1 to 10.

7. The method of claim 6, wherein the ratio of EC:MSC is about 1:1.

8. The method of claim 1, wherein the unassembled vascular cells comprise a plurality of EC and MSC, in a ratio of EC:MSC of about 10 to 1.

9. The method of claim 1, wherein the conditioned medium is collected daily over about 1 to 10 days.

10. The method of claim 1, wherein the conditioned medium comprises an increased concentration of cytokines with non-inflammatory neutrophil chemoattractant activity.

11. The method of claim 1, wherein the conditioned medium comprises chemokine (C-X-C motif) ligand 1 (CXCL1), chemokine (C-X-C motif) ligand 8 (CXCL8), or interleukin 6 (IL6), or any combination thereof.

12. The method of claim 1, wherein the unassembled vascular cells are embedded in a hydrogel or cultured on top of hydrogel-coated cell culturing plates.

13. The method of claim 12, wherein the hydrogel is a collagen gel, a fibrin gel, a gelatin-based hydrogel, or any combination thereof.

14. The method of claim 12, wherein the hydrogel further comprises fibronectin.

15. The method of claim 12, wherein the hydrogel controls release of factors secreted by the unassembled vascular cells.

16. The method of claim 1, wherein the tissue graft is a pancreatic islet tissue graft.

17. The method of claim 1, wherein the tissue graft is a bioengineered graft or a primary tissue graft.

* * * * *

UNITED STATES PATENT AND TRADEMARK OFFICE
CERTIFICATE OF CORRECTION

| | | |
|---|---|---|
| PATENT NO. | : 11,679,126 B2 | Page 1 of 1 |
| APPLICATION NO. | : 16/461885 | |
| DATED | : June 20, 2023 | |
| INVENTOR(S) | : Juan M. Melero-Martin and Ruei-Zeng Lin | |

It is certified that error appears in the above-identified patent and that said Letters Patent is hereby corrected as shown below:

On the Title Page

Column 1 (Assignee), Line 1, delete "Chldren's" and insert -- Children's --.

In the Claims

Column 78, Line 65, Claim 4, delete "(HESS)," and insert -- (HES5), --;

Column 79, Line 6, Claim 5, delete "(HESS)," and insert -- (HES5), --;

Column 79, Line 12, Claim 6, delete "(MSC)," and insert -- (MSC) --;

Column 79, Line 16, Claim 8, delete "MSC," and insert -- MSC --.

Signed and Sealed this
Twenty-eighth Day of November, 2023

Katherine Kelly Vidal
*Director of the United States Patent and Trademark Office*